United States Patent
Saltzman et al.

(10) Patent No.: US 12,162,953 B2
(45) Date of Patent: Dec. 10, 2024

(54) ENHANCED TARGETING PLATFORM

(71) Applicants: Yale University, New Haven, CT (US); New York University, New York, NY (US)

(72) Inventors: W. Mark Saltzman, New Haven, CT (US); Gregory T. Tietjen, New Haven, CT (US); Shohei Koide, New York, NY (US); Claire Albert, New Haven, CT (US); Jordan Pober, New Haven, CT (US); Akiko Koide, New York, NY (US); Laura Bracaglia, New Haven, CT (US)

(73) Assignees: YALE UNIVERSITY, New Haven, CT (US); NEW YORK UNIVERSITY, New York, NY (US)

( * ) Notice: Subject to any disclaimer, the term of this patent is extended or adjusted under 35 U.S.C. 154(b) by 194 days.

(21) Appl. No.: 17/112,964

(22) Filed: Dec. 4, 2020

(65) Prior Publication Data
US 2021/0206879 A1    Jul. 8, 2021

Related U.S. Application Data

(60) Provisional application No. 62/944,374, filed on Dec. 6, 2019.

(51) Int. Cl.
*C07K 16/44* (2006.01)

(52) U.S. Cl.
CPC .......... *C07K 16/44* (2013.01); *C07K 2317/34* (2013.01); *C07K 2317/569* (2013.01); *C07K 2317/92* (2013.01); *C07K 2319/31* (2013.01)

(58) Field of Classification Search
None
See application file for complete search history.

(56) References Cited

U.S. PATENT DOCUMENTS

| | | | |
|---|---|---|---|
| 6,462,189 B1 | 10/2002 | Koide | |
| 6,673,901 B2 | 1/2004 | Koide | |
| 6,703,199 B1 | 3/2004 | Koide | |
| 7,078,490 B2 | 7/2006 | Koide | |
| 7,153,661 B2 | 12/2006 | Koide | |
| 7,556,925 B2 | 7/2009 | Koide | |
| 7,598,352 B2 | 10/2009 | Koide | |
| 7,858,090 B2 | 12/2010 | Koide | |
| 7,981,620 B2 | 7/2011 | Koide | |
| 8,062,858 B2 | 11/2011 | Koide | |
| 8,106,162 B2 | 1/2012 | Koide | |
| 8,263,741 B2 | 9/2012 | Koide | |
| 9,127,090 B2 | 9/2015 | Koide | |
| 9,272,043 B2 | 3/2016 | Saltzman | |
| 9,512,199 B2 | 12/2016 | Loew | |
| 2010/0022680 A1 | 1/2010 | Karnik | |
| 2013/0315834 A1* | 11/2013 | Praveen | A61K 47/6923 424/9.6 |
| 2015/0073041 A1 | 3/2015 | Saltzman | |
| 2016/0243253 A1* | 8/2016 | Fraser | A61P 1/16 |
| 2016/0251477 A1 | 9/2016 | Cui | |
| 2016/0310608 A1* | 10/2016 | Yang | A61K 47/64 |
| 2017/0000737 A1 | 1/2017 | Deng | |
| 2017/0266119 A1 | 9/2017 | Deng | |
| 2019/0184043 A1 | 6/2019 | Donnelly | |

FOREIGN PATENT DOCUMENTS

| | | | |
|---|---|---|---|
| WO | 2013082529 | 6/2013 | |
| WO | WO-2014041544 A1 * | 3/2014 | ......... A61K 47/6809 |
| WO | 2015172149 | 11/2015 | |
| WO | 2015172153 | 11/2015 | |
| WO | 2016183209 | 11/2016 | |
| WO | 2016183217 | 11/2016 | |

OTHER PUBLICATIONS

Laroui et al., J of Controlled Release 186: 41-53 (Year: 2014).*
Stenzel et al., American Chemical Society Macro Lett 2: 14-18, 2013 (Year: 2013).*
Edwards et al., J Mol Biol. 334(1): 103-118 (Year: 2003).*
Lloyd et al., Protein Engineering, Design & Selection 22:159-168 (Year: 2009).*
Albert et al., Nature communications 13: 5998 (Year: 2022).*

(Continued)

*Primary Examiner* — Phuong Huynh
(74) *Attorney, Agent, or Firm* — PABST PATENT GROUP LLP

(57) ABSTRACT

A platform technology provides particle and nucleic acid conjugates, and compositions thereof, with enhanced targeting to cells, tissues, organs. The particles and nucleic acids and other deliverables contain a synthetic binding protein such as a polypeptide monobody covalently conjugated to the surface of the particle or the nucleic acid, for linking a targeting agent to the particle's surface or the nucleic acid. The particles and nucleic acids and other deliverables optionally contain an antibody non-covalently conjugated to the binding protein, via an Fc domain of the antibody. The particles can include therapeutic agents, diagnostic agents, prophylactic agents, or a combination thereof, to be delivered to desired cells, tissues, and/or organs. The particles and nucleic acids and other deliverables can be used in a wide array of applications including, but not limited to, ex vivo perfusion of mammalian organs and in vivo disease treatment.

16 Claims, 11 Drawing Sheets
Specification includes a Sequence Listing.

(56) References Cited

OTHER PUBLICATIONS

Agarwal, et al., "In vivo generated human CAR T cells eradicate tumor cells", OncoImmunology, 8(12):e1671761 (2019).
Binz, et al., "Designing repeat proteins: well-expressed, soluble and stable proteins from combinatorial libraries of consensus ankyrin repeat proteins", J. Mol. Biol., 332(2):489-503 (2003).
Cheng, et al., "A holistic approach to targeting disease with polymer nanoparticles", Nature Reviews Drug Discovery 14(4):239-247 (2015).
Cui, et al., "Ex vivo pretreatment of human vessels with siRNA nanoparticles provides protein silencing in endothelial cells", Nature Communications, 8(191): 1-11 (2017).
Danielyan, et al., "Delivery of Anti-Platelet-Endothelial Cell Adhesion Molecule Single-Chain Variable Fragment-Urokinase Fusion Protein to the Cerebral Vasculature Lyses Arterial Clots and Attenuates Postischemic Brain Edema", J. Pharmacol. Exp. Ther., 321(3):947-952 (2007).
Diem, et al., "Selection of high-affinity Centyrin FN3 domains from a simple library diversified at a combination of strand and loop positions" Protein Eng. Des. Sel., 27:419-429 (2014).
Dirito, et al., "The future of marginal kidney repair in the context of normothermic machine perfusion", Am. J. Transplant, 18:2400-2408 (2018).
Forrer, et al., "A novel strategy to design binding molecules harnessing the modular nature of repeat proteins", FEBS Lett., 539(1-3):2-6 (2003).
Gilbreth, et al., "A Dominant Conformational Role for Amino Acid Diversity in Minimalist Protein-Protein Interfaces", J Mol Biol., 381(2):407-18 (2008).
Gilbreth, et al., "Isoform-specific monobody inhibitors of small ubiquitin-related modifiers engineered using structure-guided library design", PNAS, 108(19):7751-6 (2011).
Gilbreth, et al., "Stabilization of the third fibronectin type III domain of human tenascin-C through minimal mutation and rational design", Protein Eng. Des. Sel., 27(10):411-418 (2014).
Gupta, et al., "Facile target validation in an animal model with intracellularly expressed monobodies", Nat Chem Biol., 14(9):895-900 (2018).
Huang, et al., "Vascular normalization as an emerging strategy to enhance cancer immunotherapy", Cancer Res., 73(10):2943-8 (2013).
Juliano, et al., "The delivery of therapeutic oligonucleotides", Nucleic Acids Research, 44(14):6518-6548 (2016).
Juliano, et al., "The chemistry and biology of oligonucleotide conjugates", Chem. Res., 45(7):10671-76 (2012).
Kauffman, et al., "Tunability of Biodegradable Poly(amine- co-ester) Polymers for Customized Nucleic Acid Delivery and Other Biomedical Applications", Biomacromolecules, 19(9): 3861-3873 (2018).
Kohl, et al., "Designed to be stable: Crystal structure of a consensus ankyrin repeat protein", PNAS, 100(4):1700-1705 (2003).
Koide, et al., "Teaching an old scaffold new trick: monobodies constructed using alternative surfaces of the FN3 scaffold", J Mol Biol., 415:393-405 (2012).
Koide, et al., "The fibronectin type III domain as a scaffold for novel binding proteins", J. Mol. Biol., 284(4):1141-1151 (1998).
Koide, et al., "High-affinity single-domain binding proteins with a binary-code interface", PNAS, 104(16):6632-7 (2007).
Koide, et al., "Probing protein conformational changes in living cells by using designer binding proteins: Application to the estrogen receptor", PNAS, 99(3):1253-1258 (2002).
Lonnberg, et al., "Solid-phase synthesis of oligonucleotide conjugates useful for delivery and targeting of potential nucleic acid therapeutics", Bioconjug. Chem., 20(6):1065-94 (2009).
McMahon, et al., "Yeast surface display platform for rapid discovery of conformationally selective nanobodies", Nat Struct Mol Biol., 25(3): 289-296 (2018).
Nady, et al., "ETO family protein Mtgr1 mediates Prdm14 functions in stem cell maintenance and primordial germ cell formation", Elife, 4:e10150 (2015).
National Cancer Institute website: "CAR T Cells: Engineering Patients' Immune Cells to Treat Their Cancers", < https://www.cancer.gov/about-cancer/treatment/research/car-t-cells>, accessed Apr. 19, 2022.
Nord, et al., "Binding proteins selected from combinatorial libraries of an alpha-helical bacterial receptor domain", Nat. Biotechnol., 15: 772-777 (1997).
Nord, et al., "A combinatorial library of an alpha-helical bacterial receptor domain", Prot. Eng., 8(6):601-608 (1995).
Phelps, et al., "Novel modifications in RNA", ACS Chem. Biol., 7(1): 100-9 (2012).
Ravasco, et al., "Bioconjugation with Maleimides: A Useful Tool for Chemical Biology", Chem. Eur. J., 25:43-59 (2019).
Salzman, et al., "Stachel-independent modulation of GPR56/ADGRG1 signaling by synthetic ligands directed to its extracellular region", PNAS 114(38):10095-10100 (2017).
Salzman, et al., "Structural Basis for Regulation of GPR56/ADGRG1 by Its Alternatively Spliced Extracellular Domains", Neuron., 91(6):1292-304 (2016).
Sandstrom, et al., "Inhibition of the CD28-CD80 co-stimulation signal by a CD28-binding affibody ligand developed by combinatorial protein engineering", Protein Eng., 16(9): 691-697 (2003).
Scherpereel, "Platelet-endothelial cell adhesion molecule-1-directed immunotargeting to cardiopulmonary vasculature", J. Pharmacol. Exp. Ther.. 300(3):777-786 (2002).
Schlatter, et al., "Generation, characterization and structural data of chymase binding proteins based on the human Fyn kinase SH3 domain", MAbs, 4(4):497-508 (2012).
Sha, et al., "Monobodies and other synthetic binding proteins for expanding protein science", Protein Sci., 26(5): 910-924 (2017).
Sha, et al., "Dissection of the BCR-ABL signaling network using highly specific monobody inhibitors to the SHP2 SH2 domains", PNAS, 110:14924-14929 (2013).
Shabanpoor, et al., "Bi-specific splice-switching PMO oligonucleotides conjugated via a single peptide active in a mouse model of Duchenne muscular dystrophy", Nucleic Acids Res., 43(1):29-39 (2015).
Silacci, et al., "Linker length matters, fynomer-Fc fusion with an optimized linker displaying picomolar IL-17A inhibition potency", The Journal Of Biological Chemistry, 289(20):14392-14398 (2014).
Spencer-Smith, et al., "Inhibition of RAS function through targeting an allosteric regulatory site", Nat Chem Biol., 13(1):62-8 (2017).
Stockridge, et al., "Proof of dual-topology architecture of Fluc F-channels with monobody blockers", Nat Commun., 5:5120 (2014).
Szoka, et al., "Comparative properties and methods of preparation of lipid vesicles (liposomes)", Annual review of biophysics and bioengineering, 9:467-508 (1980).
Tanaka, et al., "Monobody-mediated alteration of enzyme specificity", Nat Chem Biol., 11(10):762-4 (2015).
Tietjen, et al., "Focus on Fundamentals: Achieving Effective Nanoparticle Targeting", Trends in Molecular Medicine, 24(7):598-606 (2018).
Tietjen, et al., "Nanoparticle targeting to the endothelium during normothermic machine perfusion of human kidneys", Sci. Transl. Med., 9:eaam6764, 14 pages (2017).
Tsuzuki, "Commercial scale production of inorganic nanoparticles", Int. J. Nanotechnol,. 6(5/6), 567-578 (2009).
Wikman, et al., "Selection and characterization of HER2/neu-binding affibody ligands", Protein Eng. Des. Sel., 17(5):455-462 (2004).
Willibald, et al., "Click-modified anandamide siRNA enables delivery and gene silencing in neuronal and immune cells", J. Am. Chem. Soc., 134(30):12330-12333 (2012).
Winkler, et al., "Oligonucleotide conjugates for therapeutic applications", Ther. Deliv., 4(7):791-809 (2013).
Wojcik, et al., "A potent and highly specific FN3 monobody inhibitor of the Abl SH2 domain", Nat Struct Mol Biol., 17(4):519-27 (2010).
Wojcik, et al., "Allosteric Inhibition of Bcr-Abl Kinase by High Affinity Monobody Inhibitors Directed to the Src Homology 2 (SH2)-Kinase Interface", J Biol Chem., 291(16):8836-47 (2016).
Yale Lifesciences PitchFest, 2nd Annual Pirchfest, Yale Office of Cooperative Research, 21 pages, Dec. 6, 2019.

(56) References Cited

OTHER PUBLICATIONS

Yamada, et al., "Versatile Site-Specific Conjugation of Small Molecules to siRNA Using Click Chemistry", J. Org. Chem., 76:1198-1211 (2011).
Zorba, et al., "Allosteric modulation of a human protein kinase with monobodies", PNAS, 116(28):13937-42 (2019).
Zhou, et al., Biodegradable poly(amine-co-ester) terpolymers for targeted gene delivery Nat Mater., 11(1): 82-90 (2012).
Agarwal, et al., "In vivo generated human CAR T cells eradicate tumor cells", *OncoImmunology*, 8(12):e1671761 (2019).

\* cited by examiner

SEQUENCE LISTING

<160> NUMBER OF SEQ ID NOS: 27

<210> SEQ ID NO 1
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 1

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 2
<211> LENGTH: 123
<212> TYPE: PRT
<213> ORGANISM: Artificial Sequence
<220> FEATURE:
<223> OTHER INFORMATION: synthetic polypeptide

<400> SEQUENCE: 2

Met Lys His His His His His His Ser Ser Asp Tyr Lys Asp Asp Asp
1               5                   10                  15

Asp Lys Gly Glu Asn Leu Tyr Phe Gln Gly Ser Val Ser Ser Val Pro
                20                  25                  30

Thr Lys Leu Glu Val Val Ala Ala Thr Pro Thr Ser Leu Leu Ile Ser
            35                  40                  45

Trp Asp Ala Pro Ala Val Thr Val Tyr Tyr Val Ile Thr Tyr Gly
    50                  55                  60

Glu Thr Gly Gly Asn Ser Pro Val Gln Glu Phe Thr Val Pro Gly Ser
65                  70                  75                  80

Lys Ser Thr Ala Thr Ile Ser Gly Leu Lys Pro Gly Val Asp Tyr Thr
                85                  90                  95

Ile Thr Val Tyr Ala Gly Tyr Gly Ser Gly Gly Tyr Tyr Ser Pro Ile
            100                 105                 110

Ser Ile Asn Tyr Arg Thr Glu Ile Asp Lys Cys
            115                 120

<210> SEQ ID NO 3
<211> LENGTH: 123
<212> TYPE: PRT
<213> ORGANISM: Artificial Sequence
<220> FEATURE:
<223> OTHER INFORMATION: synthetic polypeptide

<400> SEQUENCE: 3

Met Lys His His His His His His Ser Ser Asp Tyr Lys Asp Asp Asp
1               5                   10                  15

Asp Lys Gly Glu Asn Leu Tyr Phe Gln Gly Ser Val Ser Ser Val Pro
                20                  25                  30

```
Thr Lys Leu Glu Val Val Ala Ala Thr Pro Thr Ser Leu Leu Ile Ser
        35                  40                  45

Trp Asp Ala Tyr Pro Val Tyr Val Ser Tyr Tyr Arg Ile Thr Tyr Gly
    50                  55                  60

Glu Thr Gly Gly Asn Ser Pro Val Gln Glu Phe Thr Val Pro Gly Ser
65                  70                  75                  80

Ser Ser Thr Ala Thr Ile Ser Gly Leu Ser Pro Gly Val Asp Tyr Thr
                85                  90                  95

Ile Thr Val Tyr Ala Tyr Tyr Lys Tyr Gly His Tyr Trp Ser Pro Ile
                100                 105                 110

Ser Ile Asn Tyr Arg Thr Glu Ile Asp Lys Cys
            115                 120

<210> SEQ ID NO 4
<211> LENGTH: 123
<212> TYPE: PRT
<213> ORGANISM: Artificial Sequence
<220> FEATURE:
<223> OTHER INFORMATION: synthetic polypeptide

<400> SEQUENCE: 4

Met Lys His His His His His His Ser Ser Asp Tyr Lys Asp Asp Asp
1               5                   10                  15

Asp Lys Gly Glu Asn Leu Tyr Phe Gln Gly Ser Val Ser Ser Val Pro
            20                  25                  30

Thr Lys Leu Glu Val Val Ala Ala Thr Pro Thr Ser Leu Leu Ile Ser
        35                  40                  45

Trp Asp Ala Ser Gly Ile Ser Val Ser Tyr Tyr Arg Ile Thr Tyr Gly
    50                  55                  60

Glu Thr Gly Gly Asn Ser Pro Val Gln Glu Phe Thr Val Pro Gly Ser
65                  70                  75                  80

Ser Ser Thr Ala Thr Ile Ser Gly Leu Lys Pro Gly Val Asp Tyr Thr
                85                  90                  95

Ile Thr Val Tyr Ala Tyr Tyr Lys Tyr Gly Gln Tyr Tyr Ser Pro Ile
                100                 105                 110

Ser Ile Asn Tyr Arg Thr Glu Ile Asp Lys Cys
            115                 120

<210> SEQ ID NO 5
<211> LENGTH: 4
<212> TYPE: PRT
<213> ORGANISM: Artificial Sequence
<220> FEATURE:
<223> OTHER INFORMATION: synthetic polypeptide

<400> SEQUENCE: 5

Glu Ile Asp Lys
1

<210> SEQ ID NO 6
<211> LENGTH: 93
<212> TYPE: PRT
<213> ORGANISM: Artificial Sequence
<220> FEATURE:
<223> OTHER INFORMATION: synthetic polypeptide

<400> SEQUENCE: 6

Val Ser Ser Val Pro Thr Lys Leu Glu Val Val Ala Ala Thr Pro Thr
1               5                   10                  15
```

```
Ser Leu Leu Ile Ser Trp Asp Ala Pro Ala Val Thr Val Asp Phe Tyr
            20                  25                  30

Val Ile Thr Tyr Gly Glu Thr Gly Gly Trp Tyr Ala Ala Gln Glu
        35                  40                  45

Phe Thr Val Pro Gly Ser Lys Ser Thr Ala Thr Ile Ser Gly Leu Lys
50                  55                  60

Pro Gly Val Asp Tyr Thr Ile Thr Val Tyr Ala Tyr Pro Asp His His
65                  70                  75                  80

Tyr Gln Gly Arg Ser Pro Ile Ser Ile Asn Tyr Arg Thr
                85                  90
```

<210> SEQ ID NO 7
<211> LENGTH: 92
<212> TYPE: PRT
<213> ORGANISM: Artificial Sequence
<220> FEATURE:
<223> OTHER INFORMATION: synthetic polypeptide

<400> SEQUENCE: 7

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Ile Ile Thr Tyr Gly Glu Thr Gly Gly Ser Trp Tyr Ser Ser Gln Glu
        35                  40                  45

Phe Ala Val Pro Gly Ser Lys Ser Thr Ala Thr Ile Ser Gly Leu Lys
50                  55                  60

Pro Gly Val Asp Tyr Thr Ile Thr Val Tyr Ala Ser Met Pro Gly Ser
65                  70                  75                  80

Trp Tyr Tyr Ser Pro Ile Ser Ile Asn Tyr Arg Thr
                85                  90
```

<210> SEQ ID NO 8
<211> LENGTH: 93
<212> TYPE: PRT
<213> ORGANISM: Artificial Sequence
<220> FEATURE:
<223> OTHER INFORMATION: synthetic polypeptide

<400> SEQUENCE: 8

```
Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Val Ile Thr Tyr Gly Glu Thr Gly Ser Gly Trp Phe Pro Gly Gln Thr
        35                  40                  45

Phe Glu Val Pro Gly Ser Lys Ser Thr Ala Thr Ile Ser Gly Leu Lys
50                  55                  60

Pro Gly Val Asp Tyr Thr Ile Thr Val Tyr Thr Tyr Gly Tyr Ser Ser
65                  70                  75                  80

Leu Gly Pro Gly Ser Pro Ile Ser Ile Asn Tyr Arg Thr
                85                  90
```

<210> SEQ ID NO 9
<211> LENGTH: 92
<212> TYPE: PRT
<213> ORGANISM: Artificial Sequence
<220> FEATURE:
<223> OTHER INFORMATION: synthetic polypeptide

<400> SEQUENCE: 9

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
                20                  25                  30

Val Ile Thr Tyr Gly Glu Thr Gly His Gly Trp Phe Pro Gly Gln Thr
            35                  40                  45

Phe Glu Val Pro Gly Ser Lys Ser Thr Ala Thr Ile Ser Gly Leu Lys
        50                  55                  60

Pro Gly Val Asp Tyr Thr Ile Thr Val Tyr Ala Phe Tyr Pro Arg Ser
65                  70                  75                  80

Ser Arg Pro Ser Pro Ile Ser Ile Asn Tyr Arg Thr
                85                  90

<210> SEQ ID NO 10
<211> LENGTH: 92
<212> TYPE: PRT
<213> ORGANISM: Artificial Sequence
<220> FEATURE:
<223> OTHER INFORMATION: synthetic polypeptide

<400> SEQUENCE: 10

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

Val Ile Thr Tyr Gly Glu Thr Gly Val Gly Trp Val Pro Gly Gln Thr
            35                  40                  45

Phe Thr Val Pro Gly Ser Lys Ser Thr Ala Thr Ile Ser Gly Leu Lys
        50                  55                  60

Pro Gly Val Asp Tyr Thr Ile Thr Val Tyr Ala Trp Asn Ala Ser Ile
65                  70                  75                  80

Phe Ser Tyr Ser Pro Ile Ser Ile Asn Tyr Arg Thr
                85                  90

<210> SEQ ID NO 11
<211> LENGTH: 93
<212> TYPE: PRT
<213> ORGANISM: Artificial Sequence
<220> FEATURE:
<223> OTHER INFORMATION: synthetic polypeptide

<400> SEQUENCE: 11

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp His Tyr
                20                  25                  30

Val Ile Thr Tyr Gly Glu Thr Gly Val Gly Trp Val Pro Gly Gln Thr
            35                  40                  45

Phe Thr Val Pro Gly Ser Lys Ser Thr Ala Thr Ile Ser Gly Leu Lys
        50                  55                  60

Pro Gly Val Asp Tyr Thr Ile Thr Val Tyr Ala Tyr Ser Glu Trp Ser
65                  70                  75                  80

Tyr Phe Val Ile Asn Pro Ile Ser Ile Asn Tyr Arg Thr
                85                  90

<210> SEQ ID NO 12
<211> LENGTH: 91

```
<212> TYPE: PRT
<213> ORGANISM: Artificial Sequence
<220> FEATURE:
<223> OTHER INFORMATION: synthetic polypeptide

<400> SEQUENCE: 12

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Tyr Tyr
            20                  25                  30

Val Ile Thr Tyr Gly Glu Thr Gly His Gly Gly Tyr Tyr Tyr Gln Glu
        35                  40                  45

Phe Lys Val Pro Gly Ser Lys Ser Thr Ala Thr Ile Ser Gly Leu Lys
    50                  55                  60

Pro Gly Val Asp Tyr Thr Ile Thr Val Tyr Ala Tyr Asp Asp Glu Tyr
65                  70                  75                  80

Ser Ser Ser Pro Ile Ser Ile Asn Tyr Arg Thr
                85                  90

<210> SEQ ID NO 13
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 13

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Leu Tyr
            20                  25                  30

Tyr Ile Thr Tyr Gly Glu Thr Gly Trp Trp Tyr Pro Ser Ser Tyr Gln
        35                  40                  45

Glu Phe Ala Val Pro Gly Ser Lys Ser Thr Ala Thr Ile Ser Gly Leu
    50                  55                  60

Lys Pro Gly Val Asp Tyr Thr Ile Thr Val Tyr Ala Glu Ser Gly Trp
65                  70                  75                  80

Gly Tyr Asp Val Ser Ser Pro Ile Ser Ile Asn Tyr Arg Thr
                85                  90

<210> SEQ ID NO 14
<211> LENGTH: 93
<212> TYPE: PRT
<213> ORGANISM: Artificial Sequence
<220> FEATURE:
<223> OTHER INFORMATION: synthetic polypeptide

<400> SEQUENCE: 14

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Gly Ser Trp Tyr Gly Trp Gln Glu
        35                  40                  45

Phe Ala Val Pro Gly Ser Lys Ser Thr Ala Thr Ile Ser Gly Leu Lys
    50                  55                  60

Pro Gly Val Asp Tyr Thr Ile Thr Val Tyr Ala Tyr Pro Asp His His
65                  70                  75                  80

Tyr Gln Gly Arg Ser Pro Ile Ser Ile Asn Tyr Arg Thr
```

```
                    85                  90

<210> SEQ ID NO 15
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 15

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Phe Phe Tyr
            20                  25                  30

Phe Ile Thr Tyr Gly Glu Thr Gly Gly Asn Ser Pro Val Gln Lys Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Leu Tyr Arg Ser Gln Lys
65                  70                  75                  80

Ser Gly Gln Tyr Asp Tyr Ser Ser Pro Ile Ser Ile Asn Tyr Arg Thr
                85                  90                  95

<210> SEQ ID NO 16
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 16

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Val Leu Tyr
            20                  25                  30

Val Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Gln Tyr Glu Ser Gly Thr
65                  70                  75                  80

Trp Leu Tyr Arg Gly Ser Pro Ile Ser Ile Asn Tyr Arg Thr
                85                  90

<210> SEQ ID NO 17
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 17

Val Ser Ser Val Pro Thr Lys Leu Glu Val Val Ala Ala Thr Pro Thr
1               5                   10                  15

Ser Leu Leu Ile Ser Trp Asp Ala Pro Ala Val Thr Val Asp Phe Tyr
            20                  25                  30

Phe Ile Thr Tyr Gly Glu Thr Gly Trp Gly Tyr Gly Ser Tyr Gln Ala
        35                  40                  45

Phe Glu Val Pro Gly Ser Lys Ser Thr Ala Thr Ile Ser Gly Leu Lys
    50                  55                  60
```

Pro Gly Val Asp Tyr Thr Ile Thr Val Tyr Ala Tyr Tyr Asp Ser
65                  70                  75                  80

Gln Arg Phe Leu His Ser Gly Ser Pro Ile Ser Ile Asn Tyr Arg Thr
            85                  90                  95

<210> SEQ ID NO 18
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 18

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Ser Thr Ala Thr Ile Ser Gly Leu Lys Pro
    50                  55                  60

Gly Val Asp Tyr Thr Ile Thr Val Tyr Ala Gln Ser Gly Pro Tyr Tyr
65                  70                  75                  80

Trp Tyr Trp Gly Asp Ser Pro Ile Ser Ile Asn Tyr Arg Thr
            85                  90

<210> SEQ ID NO 19
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 19

Val Ser Ser Val Pro Thr Lys Leu Glu Val Val Ala Ala Thr Pro Thr
1               5                   10                  15

Ser Leu Leu Ile Ser Trp Asp Ala Thr Gly Tyr Tyr Val Arg Tyr Tyr
            20                  25                  30

Arg Ile Thr Tyr Gly Glu Thr Gly Gly Asn Ser Pro Val Gln Glu Phe
            35                  40                  45

Thr Val Pro Gly Ser Ser Thr Ala Thr Ile Ser Gly Leu Lys Pro
    50                  55                  60

Gly Val Asp Tyr Thr Ile Thr Val Tyr Ala Gln Ser Gly Pro Tyr Tyr
65                  70                  75                  80

Trp Tyr Trp Gly Asp Ser Pro Ile Ser Ile Asn Tyr Arg Thr
            85                  90

<210> SEQ ID NO 20
<211> LENGTH: 94
<212> TYPE: PRT
<213> ORGANISM: Artificial Sequence
<220> FEATURE:
<223> OTHER INFORMATION: synthetic polypeptide

<400> SEQUENCE: 20

Val Ser Ser Val Pro Thr Lys Leu Glu Val Val Ala Ala Thr Pro Thr
1               5                   10                  15

Ser Leu Leu Ile Ser Trp Asp Ala Ser Ser Ser Val Ser Tyr Tyr
            20                  25                  30

```
Arg Ile Thr Tyr Gly Glu Gly Gly Asn Ser Pro Val Gln Glu Phe
         35                  40                  45

Thr Val Pro Gly Ser Ser Ser Thr Ala Thr Ile Ser Gly Leu Lys Pro
 50                  55                  60

Gly Val Asp Tyr Thr Ile Thr Val Tyr Ala Gly Val Gly Asn Tyr Lys
 65                  70                  75                  80

Tyr Trp Trp Gly Ser Ser Pro Ile Ser Ile Asn Tyr Arg Thr
                 85                  90
```

<210> SEQ ID NO 21
<211> LENGTH: 97
<212> TYPE: PRT
<213> ORGANISM: Artificial Sequence
<220> FEATURE:
<223> OTHER INFORMATION: synthetic polypeptide

<400> SEQUENCE: 21

```
Val Ser Ser Val Pro Thr Lys Leu Glu Val Val Ala Ala Thr Pro Thr
 1               5                  10                  15

Ser Leu Leu Ile Ser Trp Asp Ala Asn Tyr Tyr Ser Tyr Gly Asp
                 20                  25                  30

Val Ile Tyr Tyr Arg Ile Thr Tyr Gly Glu Thr Gly Gly Asn Ser Pro
                 35                  40                  45

Val Gln Glu Phe Thr Val Pro Tyr Tyr Ser Thr Ala Thr Ile Ser
 50                  55                  60

Gly Leu Lys Pro Gly Val Asp Tyr Thr Ile Thr Val Tyr Ala Tyr Asp
 65                  70                  75                  80

Glu Tyr Tyr Thr Tyr Gly Trp Ser Ser Pro Ile Ser Ile Asn Tyr Arg
                 85                  90                  95

Thr
```

<210> SEQ ID NO 22
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 22

```
Val Ser Ser Val Pro Thr Lys Leu Glu Val Val Ala Ala Thr Pro Thr
 1               5                  10                  15

Ser Leu Leu Ile Ser Trp Asp Ala Met Lys Asn Asp Glu Asp Val Gln
                 20                  25                  30

Tyr Tyr Arg Ile Thr Tyr Gly Glu Thr Gly Gly Asn Ser Pro Val Gln
                 35                  40                  45

Glu Phe Thr Val Pro Gly Ser Ser Ser Thr Ala Thr Ile Ser Gly Leu
 50                  55                  60

Lys Pro Gly Val Asp Tyr Thr Ile Thr Val Tyr Ala Gly Val Ser Ser
 65                  70                  75                  80

Tyr Tyr Tyr Tyr Trp Gly Ser Ser Pro Ile Ser Ile Asn Tyr Arg Thr
                 85                  90                  95
```

<210> SEQ ID NO 23
<211> LENGTH: 91
<212> TYPE: PRT
<213> ORGANISM: Artificial Sequence
<220> FEATURE:
<223> OTHER INFORMATION: synthetic polypeptide

<400> SEQUENCE: 23

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Asp Tyr Tyr
            20                  25                  30

Val Ile Thr Tyr Gly Glu Thr Gly Val Gly Trp Val Pro Gly Gln Thr
            35                  40                  45

Phe Glu Val Pro Gly Ser Lys Ser Thr Ala Thr Ile Ser Gly Leu Lys
        50                  55                  60

Pro Gly Val Asp Tyr Thr Ile Thr Val Tyr Ala Tyr His Glu Tyr Tyr
65                  70                  75                  80

Phe Ile Ser Pro Ile Ser Ile Asn Tyr Arg Thr
            85                  90

<210> SEQ ID NO 24
<211> LENGTH: 96
<212> TYPE: PRT
<213> ORGANISM: Artificial Sequence
<220> FEATURE:
<223> OTHER INFORMATION: synthetic polypeptide

<400> SEQUENCE: 24

Val Ser Ser Val Pro Thr Lys Leu Glu Val Ala Ala Thr Pro Thr
1               5                   10                  15

Ser Leu Leu Ile Ser Trp Asp Ala Pro Ala Val Thr Val Asp Phe Tyr
            20                  25                  30

Tyr Ile Thr Tyr Gly Glu Thr Gly Ser Ser Tyr Trp Ser Tyr Gln Glu
            35                  40                  45

Phe Thr Val Pro Gly Ser Lys Ser Thr Ala Thr Ile Ser Gly Leu Lys
        50                  55                  60

Pro Gly Val Asp Tyr Thr Ile Thr Val Tyr Ala Ile Asp Gln Trp Gln
65                  70                  75                  80

Tyr Tyr Tyr Tyr Glu Met Gly Ser Pro Ile Ser Ile Asn Tyr Arg Thr
                85                  90                  95

<210> SEQ ID NO 25
<211> LENGTH: 114
<212> TYPE: PRT
<213> ORGANISM: Artificial Sequence
<220> FEATURE:
<223> OTHER INFORMATION: synthetic polypeptide

<400> SEQUENCE: 25

Met Gly Val Ser Asp Val Pro Arg Asp Leu Glu Val Val Ala Ala Thr
1               5                   10                  15

Pro Thr Ser Leu Leu Ile Ser Trp Asp Ser Gly Arg Gly Ser Tyr Gln
            20                  25                  30

Tyr Tyr Arg Ile Thr Tyr Gly Glu Thr Gly Gly Asn Ser Pro Val Gln
            35                  40                  45

Glu Phe Thr Val Pro Gly Pro Val His Thr Ala Thr Ile Ser Gly Leu
        50                  55                  60

Lys Pro Gly Val Asp Tyr Thr Ile Thr Val Tyr Ala Val Thr Asp His
65                  70                  75                  80

Lys Pro His Ala Asp Gly Pro His Thr Tyr His Glu Ser Pro Ile Ser
                85                  90                  95

Ile Asn Tyr Arg Thr Glu Ile Asp Lys Pro Ser Gln His His His His
            100                 105                 110

His His

```
<210> SEQ ID NO 26
<211> LENGTH: 109
<212> TYPE: PRT
<213> ORGANISM: Artificial Sequence
<220> FEATURE:
<223> OTHER INFORMATION: synthetic polypeptide

<400> SEQUENCE: 26

Met Gly Val Ser Asp Val Pro Arg Asp Leu Glu Val Val Ala Ala Thr
1               5                   10                  15

Pro Thr Ser Leu Leu Ile Ser Trp Glu His Asp Tyr Pro Tyr Arg Arg
                20                  25                  30

Tyr Tyr Arg Ile Thr Tyr Gly Glu Thr Gly Gly Asn Ser Pro Val Gln
            35                  40                  45

Glu Phe Thr Val Pro Lys Asp Val Asp Thr Ala Thr Ile Ser Gly Leu
    50                  55                  60

Lys Pro Gly Val Asp Tyr Thr Ile Thr Val Tyr Ala Val Thr Ser Ser
65                  70                  75                  80

Tyr Lys Tyr Asp Met Gln Tyr Ser Pro Ile Ser Ile Asn Tyr Arg Thr
                85                  90                  95

Glu Ile Asp Lys Pro Ser Gln His His His His His His
            100                 105

<210> SEQ ID NO 27
<211> LENGTH: 88
<212> TYPE: PRT
<213> ORGANISM: Artificial Sequence
<220> FEATURE:
<223> OTHER INFORMATION: synthetic polypeptide

<400> SEQUENCE: 27

Glu Val Val Ala Ala Thr Pro Thr Ser Leu Leu Ile Ser Trp Ser Tyr
1               5                   10                  15

Asp Gly Pro Ile Asp Arg Tyr Tyr Arg Ile Thr Tyr Gly Glu Thr Gly
                20                  25                  30

Gly Asn Ser Pro Val Gln Glu Phe Thr Val Pro Pro Asp Gln Lys Thr
            35                  40                  45

Ala Thr Ile Ser Gly Leu Lys Pro Gly Val Asp Tyr Thr Ile Thr Val
    50                  55                  60

Tyr Ala Val Arg Leu Glu Gly Ala His Tyr Asn Arg Glu Phe Pro Ile
65                  70                  75                  80

Ser Ile Asn Tyr Arg Thr Pro Cys
                85
```

ENHANCED TARGETING PLATFORM

CROSS-REFERENCE TO RELATED APPLICATIONS

This application claims the benefit of and priority to U.S. Provisional Application No. 62/944,374, entitled "Enhanced Targeting Platform", filed in the United States Patent and Trademark Office on Dec. 6, 2019, which is specifically incorporated by reference herein in its entirety.

STATEMENT REGARDING FEDERALLY SPONSORED RESEARCH

This invention was made with government support under AI132895 awarded by NIH National Institute of Allergy and Infectious Diseases. The government has certain rights in the invention.

REFERENCE TO THE SEQUENCE LISTING

The Sequence Listing submitted as a text file named "YU_7832_ST25" created on Dec. 4, 2020, and having a size of 25,318 bytes is hereby incorporated by reference pursuant to 37 C.F.R. § 1.52(e)(5).

FIELD OF THE INVENTION

The disclosed invention is generally in the field of targeted delivery, including sustained and/or controlled delivery, of therapeutic agents, diagnostic agents, and/or prophylactic agents, particularly targeted delivery of these agents employing particles that contain a synthetic binding protein conjugated to the surface of the particles.

BACKGROUND OF THE INVENTION

Enormous preclinical and clinical effort/resources have been expended to produce targeted particles capable of site-specific delivery of therapeutic agents, diagnostic agents, and/or prophylactic agents with limited and/or reduced off-target toxicity. However, current approaches have yet to produce a clinically viable formulation. A key shortcoming of standard, direct chemical conjugation approaches to introducing targeting agents (such as antibodies) to the surface of particles is the use of amine-coupling chemistries. This method has two major limitations: 1) random targeting agent orientation, and 2) lack of adaptability, which severely stunts rapid design of effective targeted particles.

Random orientation of the targeting on the surface of the particle, gives rise to poor display of target recognition surface(s) of the targeting agent, which compromises targeting efficacy. In the case of coupling targeting agents via amine-coupling chemistries group, reactive groups on the surfaces of the particles must first be activated, such as via 1-ethyl-3-(-3-dimethylaminopropyl) carbodiimide hydrochloride/N-hydroxysuccinimide coupling techniques. Further, these methods require a large excess of targeting agent, multiple centrifugation, multiple tube exchange steps, vigorous shaking, and multiple pH modifications which give rise to a lack of adaptability. As a result of these limitations, translating the robust binding of targeted particles observed in a Petri dish into a complex mammalian organ remains an unmet need.

Others have used engineered proteins to couple directly to particles through different chemistries that might yield more specific orientations. But this is very costly and time consuming to do for every potential target.

Accordingly, it is an object of the invention to provide particles with improved targeting properties, and compositions and methods of use thereof.

SUMMARY OF THE INVENTION

A platform technology provides particles and nucleic acids and other deliverables with enhanced targeting to cells, tissues, organs. Also provided are compositions containing these particles and nucleic acids and other deliverables. The particles and nucleic acids and other deliverables contain a synthetic binding protein such as a polypeptide monobody. The synthetic binding protein typically has structural features that enhance the spatial orientation of the binding site of a targeting agent when conjugated to the synthetic binding protein. This system allows bypassing of re-engineering every targeting molecule and use already existing targeting molecules by simply adding the synthetic binding protein binding site.

The synthetic binding protein can contain a first surface containing a targeting agent binding site and a second surface containing a cysteine, through which the synthetic binding protein is conjugated to the particle's surface or the nucleic acid. The first surface and the second surface are non-overlapping and separated by a portion of the synthetic binding protein. The first and second surfaces can be adjacent or at opposing end so the synthetic binding protein. The cysteine is typically added in a place where it will not adversely effect binding of the synthetic binding protein to its target. For example, the cysteine can be introduced at a terminus (e.g., the N- or C-terminus) or an internal site of the synthetic binding protein. In some embodiments, there is a spacer (e.g., one or more amino acids) added to the C-terminus of the synthetic binding protein, and the cysteine is added thereto. A cysteine at the C-terminus ensures that the synthetic binding protein can be conjugated to drug delivery vehicles without impinging on the functional binding site of the synthetic binding protein.

In some embodiments, the synthetic binding protein is covalently conjugated to the surface of the particle or nucleic acid, by reacting the thiol functional group of the cysteine with a maleimide moiety on the surface of the particle or nucleic acid, to form a 3-thiopyrrolidine-2,5-dione moiety in the covalent linkage. Although introduced with respect to monobodies, a similar strategy can be applied to other synthetic binding proteins including those discussed in more detail below.

In some forms, the particle is a polymeric particle that contains a blend of (i) a first amphiphilic polymer containing a poly(lactic acid)-block-poly(ethylene glycol) copolymer, and a synthetic binding protein conjugated to the poly (ethylene glycol) via a covalent bond that contains a 3-thiopyrrolidine-2,5-dione moiety, and (ii) a second amphiphilic polymer a poly(lactic acid)-block-poly(ethylene glycol) copolymer. The second amphiphilic polymer does not contain a synthetic binding protein.

In some forms the polymeric particles if a poly(amine-co-ester)-based particle such as PACE-PVA-VS.

In some embodiments the particle is an inorganic particle such as gold nanoparticle.

In some forms, a targeting agent such as an antibody, nanobody, monobody, Fc fusion of a natural receptor and its variants, etc. is non-covalently bound to the synthetic binding protein such as synthetic binding protein. In such embodiments, the synthetic binding protein is typically specific for a region of the antibody, preferably a constant region of the antibody, for example an Fc domain. The synthetic binding protein conjugates non-covalently to the antibody (e.g., the Fc domain) via a surface of the synthetic binding protein, which is distinct from (e.g., non-overlapping with) the surface through which the synthetic binding protein is conjugated to the poly(ethylene glycol).

In some embodiments, the synthetic binding protein such as a monobody binds directly to the target and thus serves as the targeting agent without an additional molecule such as an antibody serving as a bridge between the synthetic binding protein and the target cells or tissue.

The particles can include therapeutic agents, diagnostic agents, prophylactic agents, or a combination thereof, to be delivered to desired cells, tissues, and/or organs. Alternatively, the synthetic binding protein can be conjugated directed to the therapeutic agent, diagnostic agent, or prophylactic agent.

Also described are methods of using this platform technology including, but not limited to, cell, tissue, and/or organ transplant settings, such as ex vivo perfusion of mammalian organs. The particles and compositions containing these particles are useful in the controlled release of therapeutic agents, diagnostic agents, and/or prophylactic agents in a targeted manner. The nucleic acid conjugate can themselves be therapeutic agents, diagnostic agents, and/or prophylactic agents deliverable in a targeted manner. The particles and nucleic acids and other deliverables can be administered to cells, tissues, and/or organs with or without the presence of an antibody conjugated to the synthetic binding protein. Accordingly, in some forms, an effective amount of the particles or nucleic acids or other deliverable containing the synthetic binding protein conjugated thereto, is administered after the administration of an antibody targeting agent to cells, tissues, and/or organs. The deliverable can bind to target cells, tissues, and/or organs via the synthetic binding protein (e.g., monobody) which binds specifically to the antibody of the antibody-bound target cells, tissues, and/or organs. In some forms, an effective amount of the particles or nucleic acids or other deliverable containing the synthetic binding protein conjugated thereto and an antibody conjugated to the synthetic binding protein is administered to cells, tissues, and/or organs.

DETAILED DESCRIPTION OF THE INVENTION

I. Definitions

Figure 1A:
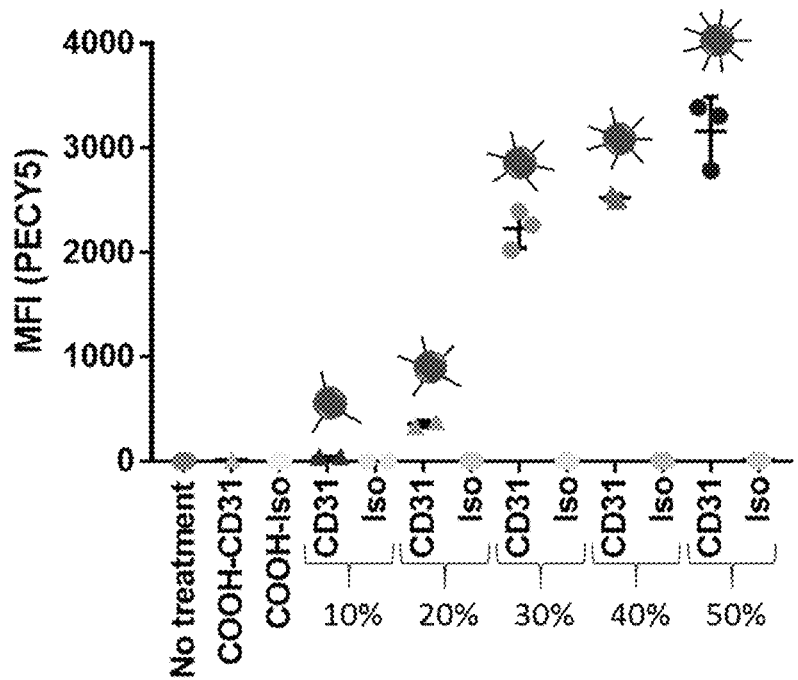
FIG. 1A is a graph showing quantification of the Mean Fluorescence Intensity (MFI, y-axis) measured by flow cytometry on human umbilical vein endothelial cells (HUVEC) exposed to Monobody (Mb) conjugated nanoparticles prepared with varying amounts of PLA-PEG-maleimide (10%-50%; x-axis). Before exposure to NPs, the cells were first treated with anti-CD31 antibody (CD31) or IgG1 isotype control antibody (Iso). MFI was assayed by flow cytometry.

The term "amino acid" refers to a molecule containing both an amino group and a carboxyl group. Amino acids include alpha-amino acids and beta-amino acids. In certain forms, an amino acid is an alpha-amino acid. Amino acids can be natural or synthetic. Amino acids include, but are not limited to, the twenty standard or canonical amino acids: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V). Common non-standard or non-canonical amino acids include, but are not limited to, selenocysteine, ornithine, pyrrolysine, and N-formylmethionine.

The term "natural amino acid" refers to both the D- and L-isomers of the 20 common naturally occurring amino acids found in peptides (e.g., A, R, N, C, D, Q, E, G, H, I, L, K, M, F, P, S, T, W, Y, V (as known by the one letter abbreviations)).

The terms "synthetic amino acid", "non-natural amino acid" and "unnatural amino acid," are used interchangeably, and refer to an organic compound that has an amino group and a carboxyl group, and is not one of the D- and L-isomers of the 20 common naturally occurring amino acids found in peptides. Generally, it mimics the reactivity of a natural amino acid due to the presence of the amino and carboxyl groups. "Synthetic amino acid," "non-natural amino acid," or "unnatural amino acid" also refers to an amino acid that is not produced by an organism without genetic engineering. The synthetic amino acid as defined herein generally increases or enhances the properties of a peptide (e.g., reactivity towards a desired molecule) when the synthetic amino acid is either substituted for a natural amino acid or incorporated into a peptide. "Synthetic amino acid," "non-natural amino acid," or "unnatural amino acid" can also refer to a natural amino acid whose side chain has been chemically modified to include a reactive group (e.g. alkyne; azide; alkene; triarylphosphine; aminooxy; carbonyl; hydrazide; sulfonyl chloride; maleimide; aziridine; —CN; acryloyl; acrylamide; sulfone; vinyl sulfone; cyanate; thiocyanate; isocyanate; isothiocyanate; alkoxysilane; dialkyl dialkoxysilane; diaryl dialkoxysilane; trialkyl monoalkoxysilane; vinyl silane; acetohydrazide; acyl azide; acyl halides; epoxide; glycidyl; carbodiimides; thiol; amine; phosphoramidate; vinyl ether; substituted hydrazine; an alkylene glycol bis(diester), e.g. ethylene glycol bis(succinate); thioester, e.g., alkyl thioester, α-thiophenylester, allyl thioester (e.g., allyl thioacetate, allyl thioprionate); allyl ester (e.g., allyl acetate, allyl propionate); aryl acetate (e.g. phenacyl ester); orthoester; sulfonamide, e.g. 2-N-acyl nitrobenzenesulfonamide; vinyl sulfide; or a combination thereof) such that the resulting amino acid is structurally different from any of the 20 canonical naturally occurring amino acids.

The term "biodegradable," generally refers to a material that will degrade or erode under physiologic conditions to smaller units or chemical species that are capable of being metabolized, eliminated, or excreted by the subject. The degradation time is a function of composition and morphology. Degradation times can be from hours to weeks.

"Chemical moiety" refers to a part of a molecule, such as an organic molecule.

"Conjugate," "conjugation," and related terms, refer to the covalent or non-covalent linkage of a molecule to another molecule, or one part of a molecule to a different part of the same molecule. The linkage can involve covalent or non-covalent linkage. Covalent linkages can be direct or indirect (i.e., mediated via a linker). "Covalent linkage", refers to a bond or organic moiety that covalently links molecules or different parts of the same molecule. Non-covalent linkage includes electrostatic interactions, hydrogen bonding interactions, metal coordination, physical adsorption, host-guest interactions, hydrophobic interactions, π-stacking interactions, van der Waals interactions, magnetic interactions, and dipole-dipole interactions. Non-covalent conjugation can be binding or "specific binding."

As used herein, the term "specifically binds" and "specific binding" refers to the binding of an antibody or synthetic binding protein to its cognate antigen or target while not significantly binding to other antigens or targets. Specific binding of an antibody or synthetic binding protein to a target under such conditions requires the antibody or synthetic binding protein be selected for its specificity to the target.

"Effective amount" or "therapeutically effective amount" means a dosage sufficient to reduce or inhibit one or more symptoms of a disorder, disease, or condition being treated, or to otherwise provide a desired pharmacologic and/or physiologic effect. The precise dosage will vary according to a variety of factors such as subject-dependent variables (such as, age, immune system health, etc.), the severity of the disease or disorder being treated, as well as the route of administration and the pharmacokinetics of the agent being administered.

"Fc domain" refers to the tail portion of an immunoglobulin that is formed from the heavy chains of the immunoglobulin. The Fc region includes polypeptides containing the constant region of an immunoglobulin excluding the first constant region immunoglobulin domain. Thus, Fc refers to the last two constant region immunoglobulin domains of IgA, IgD, and IgG, and the last three constant region immunoglobulin domains of IgE and IgM.

"Immunoglobulin fold" refers to a peptide structural architecture containing a barrel-like core whose "staves" are formed from anti-parallel β-sheets, with pairs of β-sheets connected by peptide segments that form loop structures.

"Monobody," "monobodies," or related terms, are antibody mimics that can be formed using a small j-sheet protein scaffold, such as the tenth fibronectin type 3 (FN3) domain from human fibronectin (FNfn10) (Koide, et al., 1998), consensus FN3 domains (PMID 24786107), FN3 domains of human tenascin C (PMID 23989160). Unlike conventional Ig domains, FNfn10 does not contain disulfide bonds or metal binding sites, is highly stable and undergoes reversible unfolding (Koide, et al., 1998; Main, et al., 1992; Plaxco, et al., 1996). See also, e.g., U.S. Pat. Nos. 6,673,901 and 9,512,199.

"Non-solvent," "polymer non-solvent," or "non-solvent of the polymer" are art-recognized terms, and are used interchangeably to refer to a "poor" solvent for a polymer, i.e., a solvent in which a polymer dissolves poorly.

"Particle" refers to any entity having a diameter of less than 1000 μm. These include nanoparticles and microparticles. "Nanoparticle" refers to any particle having a diameter greater than 1 nm and less than 1000 nm. "Microparticle" refers to any particle having a diameter of at least 1 μm and less than 1000 μm. Nanoparticles and microparticles having a spherical shape are generally referred to as "nanospheres" and "microspheres," respectively.

"Pharmaceutically acceptable," refers to compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio, in accordance with the guidelines of agencies such as the Food and Drug Administration. A "pharmaceutically acceptable carrier," refers to all components of a pharmaceutical formulation which facilitate the delivery of the composition in vivo. Pharmaceutically acceptable carriers include, but are not limited to, diluents, preservatives, binders, lubricants, disintegrators, swelling agents, fillers, stabilizers, and combinations thereof.

"Small molecule" generally refers to an organic molecule that is less than about 2000 g/mol in molecular weight, less than about 1500 g/mol, less than about 1000 g/mol, less than about 800 g/mol, or less than about 500 g/mol. In some forms, small molecules are non-polymeric and/or non-oligomeric.

"Synthetic binding protein" are human-made proteins that have been engineered to bind to a target molecule of interest (Sha, et al., Protein Sci. 2017, 26(5), 910-924).

"Targeting agent binding site," as relates to a synthetic binding protein, refers to a portion of the synthetic binding protein that can bind to a targeting agent.

"Targeting agent" refers to a chemical compound that can direct a particle to a receptor site on a selected cell or tissue type, can serve as an attachment molecule, or serve to couple or attach another molecule. The term "direct," as relates to chemical compounds, refers to causing a particle to preferentially attach to a selected cell or tissue type. This targeting agent, generally binds to its receptor with high affinity and specificity.

"Treating" refers to preventing or alleviating one or more symptoms of a disease, disorder, or condition. Treating the disease or condition includes ameliorating at least one symptom of the particular disease or condition, even if the underlying pathophysiology is not affected, such as treating the pain of a subject by administration of an analgesic agent even though such agent does not treat the cause of the pain.

II. Compositions

Particles and nucleic acids and other deliverables with enhanced targeting to cells, tissues, and organs, as well as compositions containing these particles and nucleic acids and other deliverables are provided. The particles can include therapeutic agents, diagnostic agents, prophylactic agents, or a combination thereof. The nucleic acids can themselves be therapeutic agents, diagnostic agents, prophylactic agents, or a combination thereof. The particles, nucleic acids or other deliverables contain one or more synthetic binding proteins. The synthetic binding proteins are designed such that they contain a first surface containing a targeting agent binding site, and a second distinct (e.g., non-overlapping) surface containing a chemical moiety through which the synthetic binding protein is conjugated to the particle's surface or the nucleic acid. Further, the first surface and the second surface are typically separated by a portion of the synthetic binding protein to ensure the binding activity of the synthetic binding protein is preserved.

In some embodiments, the targeting agent binding site of the synthetic binding protein itself serves as a targeting agent directing the particle or nucleic acid or other deliverable to a selected cell or tissue type.

In some forms, the particle or nucleic acid further contains a targeting agent conjugated to the targeting agent binding site of the synthetic binding protein. An exemplary targeting agent is an antibody. In such embodiments, the antibody typically serves as a targeting agent to ensure specific retention of the particle or nucleic acid or other deliverable to a site on a selected cell or tissue type, while the synthetic binding protein links the targeting agent to the particle or nucleic acid or other deliverable. In some forms, the targeting agent is an antibody that is conjugated to the targeting agent binding site via an Fc domain of the antibody. By targeting the Fc portion of an antibody, the particles and nucleic acids and other deliverables can use existing antibodies and do not require re-engineering every targeting antibody as is necessary with other existing conjugation chemistries (such as 'Click' chemistry). Other non-antibody targeting agents can be engineered to include an Fc sequences, and thus bind to the synthetic binding protein-deliverable platform the Fc binding monobody and the Fc binding region. Such other targeting agents may be other monobodies, nanobodies, etc.

In some forms, at least one of the synthetic binding proteins, such as monobodies, have a molecular weight between 5 kDa and 50 kDa inclusive, between 5 kDa and 21 kDa inclusive, 5 kDa and 17.5 kDa, inclusive, between 7.5 kDa and 20 kDa, inclusive, between 7.5 kDa and 17.5 kDa, inclusive, or between 10 kDa and 15 kDa, inclusive. Exemplary synthetic binding proteins such as DARPins are typically 14-21 kDa, and Anticalins are about 20 kDa.

In some embodiments, the synthetic binding protein is a concatenated version that contain multiple units of a binding protein within a single polypeptide (e.g., in this range) and thus have greater MW than this range. The molecules of synthetic binding protein can be separated by a spacer (e.g., a spacer composed of amino acids). In some forms, at least one of the synthetic binding proteins is based on a fibronectin type III domain.

In some forms, at least one of the synthetic binding proteins contains an immunoglobulin fold and no disulfide bonds. Preferably, in some forms, at least one of the synthetic binding proteins is a polypeptide monobody.

Preferably, the synthetic binding protein is conjugated to the particle's or nucleic acid's surface via a covalent linkage that contains a 3-thiopyrrolidine-2,5-dione moiety. In some forms, the synthetic binding protein is conjugated to the surface of the particle or nucleic acid via a cysteine. The cysteine can be introduce at any surface exposed position within the synthetic binding protein (e.g., monobody) The cysteine is typically added in a place where it will not adversely affect binding of the binding protein to its target. A cysteine at the C-terminus ensures that the monobody can be conjugated to drug delivery vehicles without impinging on the functional binding surface of the monobody. Thus, in some forms, the cysteine is located at the C-terminus of the synthetic binding protein. In some embodiments, the cysteine is added to a side opposing the binding surface of the binding protein.

In some forms, the particle is a polymeric particle containing one or more amphiphilic polymers containing a hydrophobic polymer portion and a hydrophilic polymer portion. In some forms the synthetic binding protein is conjugated, preferably covalently, to the hydrophilic polymer portion of one or more amphiphilic polymers. In some forms, the targeting agent is further conjugated, preferably non-covalently, to the targeting agent binding site of the synthetic binding protein. In some forms, the hydrophobic polymer portion contains a polyester. In some forms, the hydrophilic polymer section contains a polyethylene glycol. Preferably, the polyesters are selected from polyhydroxy acids, such as poly(lactic acid)s, poly(lactic acid-co-glycolic acid)s, poly(glycolic acid)s, and combinations thereof. In some forms, the amphiphilic polymer is selected from poly(lactic acid)-block-poly(ethylene glycol)s, poly(glycolic acid)-block-poly(ethylene glycol)s, poly(lactide-co-glycolic)-block-poly(ethylene glycol), or a combination thereof.

The nucleic acid can be composed of DNA, RNA, modified nucleic acids, or a combination thereof.

A. Synthetic Binding Proteins

1. Structure of Synthetic Binding Proteins

Preferably, the synthetic binding proteins described herein contain a first surface containing a targeting agent binding site, and a second surface modified to contain a chemical moiety through which the synthetic binding protein can be conjugated to a particle's surface or to a nucleic acid. The conjugation occurs, preferably non-covalently, to a component of the particle, such as a polymer, lipid, or metal. Examples of synthetic binding proteins, also known as "antibody mimics," include, but are not limited to, monobodies, nanobodies, AFFIBODY(TM) anticalins, DARPins, and ubiquitin mutants (Sha, et al., Protein Sci. 2017, 26(5), 910-924, McMahon, et al., *Nat Struct Mol Biol.* 2018 Mar.; 25(3): 289-296).

Monobodies are based on the fibronectin type III domain that has an immunoglobulin fold, but no disulfide bonds (Koide, et al., J. Mol. Biol. 1998, 284, 1141-1151). Polypeptide monobodies and other synthetic binding proteins are described in Sha, et al., Protein Sci. 2017, 26(5), 910-924 and in U.S. Pat. Nos. 9,127,090, 8,263,741, 8,106,162, 8,062,858, 7,981,620, 7,858,090, 7,598,352, 7,556,925, 7,153,661, 7,078,490, 6,703,199, 6,673,901, 6,462,189, the contents of each of which are specifically incorporated by reference herein.

For example, in some embodiments, the monobody is a fibronectin type III (Fn3) polypeptide monobody having at least two Fn3-strand domain sequences with a loop region sequence linked between each Fn3-strand domain sequence. Typically at least one monobody loop region sequence varies as compared to the wild-type (e.g.,

```
                                                   (SEQ ID NO: 1))
VSDVPRDLEVVAATPTSLLISWDAPAVTVRYYRITYGETGGNSPVQEFT
VPGSKSTATISGLKPGVDYTITVYAVTGRGDSPASSKPISINYRT
``` loop region sequence by deletion of two to twelve amino acids in the loop region sequence, insertion of at least two to 25 amino acids, or replacement of at least two amino acids in the loop region sequence. Typically, the polypeptide monobody loop region includes at least two amino acids and can bind to a specific binding partner (SBP) to form a polypeptide:SBP complex.

In some embodiments, at least one loop region binds to a specific binding partner (SBP) to form a polypeptide:SBP complex having a dissociation constant of less than $10^{-6}$ moles/liter.

A loop region can include, for example, amino acid residues: i) from 15 to 16 inclusive in an AB loop; ii) from 22 to 30 inclusive in a BC loop; iii) from 39 to 45 inclusive in a CD loop; iv) from 51 to 55 inclusive in a DE loop; v) from 60 to 66 inclusive in an EF loop; or vi) from 76 to 87 inclusive in an FG loop. In some embodiments, the monobody loop region sequence varies from the wild-type Fn3 loop region sequence by the replacement of at least two amino acids in the loop region or the deletion of two to twelve amino acids in the loop region. In some embodiments, the monobody loop region sequence varies from the wild-type Fn3 loop region sequence by the insertion of from 3 to 25 amino acids. In some embodiments, the Fn3-strand domain sequences are Fn3fn10β-strand domain sequences.

In some embodiments, a fibronectin polypeptide monobody includes a plurality of Fn beta-strand domain sequences that are linked to a plurality of loop region sequences in the wild-type Fn arrangement. The loop region sequences can correspond to wild-type Fn loop region sequences AB, BC, CD, DE, EF or FG. Typically, at least one of the AB, BC, CD, DE, or FG loop region sequences is replaced by at least one CDR sequence, the monobody includes Fn beta-strands A-G, and the monobody binds to a specific binding partner.

In alternative to fibronectin type III (Fn3) polypeptide, the fibronectin polypeptide can be a fibronectin type II (Fn2) polypeptide, or a fibronectin type I (Fn1) polypeptide.

In some embodiments, a loop region being replaced by a CDR sequence is an AB loop, a CD loop, or a DE loop. In some embodiments, a loop region being replaced by a CDR sequence is a BC loop region. In some embodiments, a loop region being replaced by a CDR sequence is a FG loop region. In some embodiments, the BC, or FG loop region sequences is replaced by one CDR sequence.

In particular embodiments, the CDR sequence replaces amino acid positions 74-81 of the FG loop region, amino acid positions 75-81 of the FG loop region, amino acid positions 75-78 of the FG loop region, amino acid positions 76-80 of the FG loop region amino acid positions 76-81 of the FG loop region, amino acid positions 75-84 of the FG loop region, or amino acid positions 76-81 of the FG loop region.

The CDR sequence can be a CDR1 sequence, a CDR2 sequence, or a CDR3 sequence. The CDR sequence can be a heavy chain CDR3 sequence or a light chain CDR3 sequence.

In some embodiments, the monobody includes modifications to a beta sheet of a FnIII polypeptide in addition to modifications to at least one loop region of the FnIII based polypeptide. Such modifications can result in an FnIII based binding molecule with improved binding ability for a target molecule. The improved binding is a result of increased surface area available for binding to a target molecule by using amino acid residues in the beta sheet to form part of the binding surface and to bind to a target molecule. Modifications to the beta sheets can also be used to distinguish targets.

In some embodiments, the synthetic binding protein includes amino acid substitutions in both the beta strands in conjunction with substitutions in the AB loop, the BC loop, the CD loop, the DE loop, and/or the FG loop of FnIII. In some embodiments the synthetic binding protein includes amino acid substitution in beta strand C, beta strand D, beta strand F and/or beta strand G. In some embodiments the synthetic binding protein includes one or more amino acid substitutions in two loop regions and/or two non-loop regions, wherein the non-loop regions may be the beta strands C and F, and the loop regions may be the CD and FG loops. In some embodiments the one or more amino acid substitutions may be introduced to the cradle residues in the beta strands. In some embodiments the synthetic binding protein includes an insertion and/or deletion of at least one amino acid in at least one loop and/or non-loop region. In some embodiments the synthetic binding protein includes an insertion and/or deletion of at least one amino acid in two loop regions and/or two non-loop regions, wherein the non-loop regions may be the beta strands C and F, and the loop regions may be the CD and FG loops. In some embodiments the FnIII domain may be the 1st, 2nd, 3rd, 4th, 5th, 6th, 7th, 8th, 9th, 10th, 11th, 12th, 13th, 14th, 15th or 16th FnIII domain of human fibronectin. In some embodiments, the one or more amino acid substitutions in the non-loop region may not change the structure of the FnIII domain scaffold and/or the shape of the loop regions. In some embodiments, the one or more amino acid substitutions in the non-loop region may exclude the non-cradle residues.

In some embodiments, loop CD may be about 3-11, about 4-9, or 5 residues in length, wherein loop FG may be about 1-10, 5 or 6 residues in length. Position 1 of the FG loop may be a Gly residue, position 2 may be a Leu, Val, or Ile residue, position 3 may be a charged or polar residue, position 4 may be a Pro residue, position 5 may be a Gly residue, and position 6 may be a polar residue. In some embodiments, positions 3 and/or 5 of the loop may be a Gly residue.

In some embodiments, the beta strand lengths may be about 6-14, about 8-11, or 9 residues for beta strand C and for beta strand F about 8-13, about 9-11, or 10 residues. In some embodiments, the residue at positions 2, 4, and 6 of the C beta strand may be a hydrophobic residue, and positions 1, 3, 5, and 7-9 of the C beta strand may be altered relative to the wild type sequence, wherein the residue at position 1 of the C beta strand may be selected from the group consisting of Ala, Gly, Pro, Ser, Thr, Asp, Glu, Asn, Gln, His, Lys, and Arg. The residue at position 3 of the C beta strand may be a hydrophobic residue, or may be selected from the group consisting of Ile, Val, Arg, Leu, Thr, Glu, Lys, Ser, Gln, and His. Position 5, 7, 8, and 9 of the C beta strand may be selected from the group consisting of Ala, Gly, Pro, Ser, Thr, Asp, Glu, Asn, Gln, His, Lys, and Arg.

In some embodiments, the residue at positions 1, 3, 5, and 10 of the F beta strand may be altered relative to the wild type sequence, wherein the residues at positions 1, 3, 5, and 10 of the F beta strand may be individually selected from the group consisting of Ala, Gly, Pro, Ser, Thr, Asp, Glu, Asn, Gln, His, Lys, and Arg. The residue at positions 2, 4, and 6 of the F beta strand may be a hydrophobic residue. The residue at position 7 of the F beta strand may be a hydrophobic residue, or may be selected from the group consisting of Arg, Tyr, Ala, Thr, and Val. The residue at position 8 of the F beta strand may be selected from the group consisting of Ala, Gly, Ser, Val, and Pro. The residue at position 9 of the F beta strand may be selected from the group consisting of Val, Leu, Glu, Arg, and Ile. See also U.S. Pat. No. 9,512,199, which is specifically incorporated by reference in its entirety.

Exemplary synthetic murine Fc binding proteins include the monobodies exemplified in the experiments below:

```
pHFT1-Mb(FC-S5)-EIDKC
                                             (SEQ ID NO: 2)
MKHHHHHHSSDYKDDDDKGENLYFQGSVSSVPTKLEVVAATPTSLLISW
DAPAVTVYYYVITYGETGGNSPVQEFTVPGSKSTATISGLKPGVDYTIT
VYAGYGSGGYYSPISINYRTEIDKC pHFT1-Mb(FC-LN2)-EIDKC
                                             (SEQ ID NO: 3)
MKHHHHHHSSDYKDDDDKGENLYFQGSVSSVPTKLEVVAATPTSLLISW
DAYPVYVSYYRITYGETGGNSPVQEFTVPGSSSTATISGLSPGVDYTIT
VYAYYKYGHYWSPISINYRTEIDKC pHFT1-Mb(FC-L9)-EIDKC
                                             (SEQ ID NO: 4)
MKHHHHHHSSDYKDDDDKGENLYFQGSVSSVPTKLEVVAATPTSLLISW
DASGISVSYYRITYGETGGNSPVQEFTVPGSSSTATISGLKPGVDYTIT
VYAYYKYGQYYSPISINYRTEIDKC
```

The EIDK (SEQ ID NO:5) sequence is present in natural human fibronectin, although this segment is considered to be outside the 10th FN3 domain. These sequences include a His$_6$, FLAG epitope and a TEV cleavage site and a C-terminal tag containing a Cys residue (underlined). In some embodiments, one or more of these elements is absent or replaced with an alternative tag or cleavage site.

In some embodiments, the synthetic Fc binding protein is a variant or functional fragment of SEQ ID NO:2, 3, or 4 cleavage with at least 75%, 80%, 85%, 90%, 95%, or more sequence identity to SEQ ID NO:2, 3, or 4 with or without the His$_6$, FLAG epitope, a TEV, C-terminal tag or any combination thereof.

In some embodiments, the synthetic binding protein is a concatemer of SEQ ID NO:2, 3, or 4, or variant or functional fragment thereof with 75%, 80%, 85%, 90%, 95%, or more sequence identity to SEQ ID NO:2, 3, or 4 with or without the His$_6$, FLAG epitope, a TEV, C-terminal tag or any combination thereof.

In some embodiments, the C-terminal cysteine is in a different location, preferably where it does not affect the ability of the monobody to bind its target.

Other exemplary monobodies include those that bind to human and mouse GPR56, a cell surface receptor that could be used a potential surface marker for delivery. See, e.g., Salzman et al. 2017, PNAS 114:11095-11100.

```
Mb(hGPR56_β1)
                                             (SEQ ID NO: 6)
VSSVPTKLEVVAATPTSLLISWDAPAVTVDFYVITYGETGGWWYAAQEF
TVPGSKSTATISGLKPGVDYTITVYAYPDHHYQGRSPISINYRT

Mb(hGPR56_β2)
                                             (SEQ ID NO: 7)
VSSVPIKLEVVAATPTSLLISWDAPAVTVDFYIITYGETGGSWYSSQEF
AVPGSKSTATISGLKPGVDYTITVYASMPGSWYYSPISINYRT
```

Mb(hGPR56_β3)
(SEQ ID NO: 8)
VSSVPTKLEVVAATPTSLLISWDAPAVTVDFYVITYGETGSGWFPGQTF
EVPGSKSTATISGLKPGVDYTITVYTYGYSSLGPGSPISINYRT

Mb(hGPR56_β4)
(SEQ ID NO: 9)
VSSVPIKLEVVAATPTSLLISWDAPAVTVDFYVITYGETGHGWFPGQTF
EVPGSKSTATISGLKPGVDYTITVYAFYPRSSRPSPISINYRT

Mb(hGPR56_β5)
(SEQ ID NO: 10)
VSSVPTKLEVVAATPTSLLISWDAPAVTVDHYVITYGETGVGWVPGQTF
TVPGSKSTATISGLKPGVDYTITVYAWNASIFSYSPISINYRT

Mb(hGPR56_β6)
(SEQ ID NO: 11)
VSSVPTKLEVVAATPTSLLISWDAPAVTVDHYVITYGETGVGWVPGQTF
TVPGSKSTATISGLKPGVDYTITVYAYSEWSYFVINPISINYRT

Mb(hGPR56_β7)
(SEQ ID NO: 12)
VSSVPTKLEVVAATPTSLLISWDAPAVTVVYYVITYGETGHGGYYYQEF
KVPGSKSTATISGLKPGVDYTITVYAYDDEYSSSPISINYRT

Mb(hGPR56_β8)
(SEQ ID NO: 13)
VSSVPTKLEVVAATPTSLLISWDAPAVTVDLYYITYGETGWWYPSSYQE
FAVPGSKSTATISGLKPGVDYTITVYAESGWGYDVSSPISINYRT

Mb(hGPR56_β9)
(SEQ ID NO: 14)
VSSVPTKLEVVAATPTSLLISWDAPAVTVDYYVITYGETGGSWYGWQEF
AVPGSKSTATISGLKPGVDYTITVYAYPDHHYQGRSPISINYRT

Mb(mGPR56_β10)
(SEQ ID NO: 15)
VSSVPTKLEVVAATPTSLLISWDAPAVTVFFYFITYGETGGNSPVQKFT
VPGSKSTATISGLKPGVDYTITVYALYRSQKSGQYDYSSPISINYRT

Mb(mGPR56_β11)
(SEQ ID NO: 16)
VSSVPTKLEVVAATPTSLLISWDAPAVTVVLYVITYGETGGNSPVQEFT
VPGSKSTATISGLKPGVDYTITVYAQYESGTWLYRGSPISINYRT

Mb(mGPR56_β12)
(SEQ ID NO: 17)
VSSVPTKLEVVAATPTSLLISWDAPAVTVDFYFITYGETGWGYGSYQAF
EVPGSKSTATISGLKPGVDYTITVYAYYYDSQRFLHSGSPISINYRT

Mb(mGPR56_β13)
(SEQ ID NO: 18)
VSSVPTKLEVVAATPTSLLISWDASSSSVSYYRITYGETGGNSPVQEFT
VPGSSSTATISGLKPGVDYTITVYAQSGPYYWYWGDSPISINYRT

Mb(hGPR56_β14)
(SEQ ID NO: 19)
VSSVPTKLEVVAATPTSLLISWDATGYYVRYYRITYGETGGNSPVQEFT
VPGSSSTATISGLKPGVDYTITVYAQSGPYYWYWGDSPISINYRT

Mb(mGPR56_β15)
(SEQ ID NO: 20)
VSSVPTKLEVVAATPTSLLISWDASSSSVSYYRITYGETGGNSPVQEFT
VPGSSSTATISGLKPGVDYTITVYAGVGNYKYWWGSSPISINYRT

Mb(hGPR56_β16)
(SEQ ID NO: 21)
VSSVPTKLEVVAATPTSLLISWDANYYYSYGDVIYYRITYGETGGNSPV
QEFTVPYYYSTATISGLKPGVDYTITVYAYDEYYTYGWSSPISINYRT

Mb(mGPR56_β17)
(SEQ ID NO: 22)
VSSVPTKLEVVAATPTSLLISWDAMKNDEDVQYYRITYGETGGNSPVQE
FTVPGSSSTATISGLKPGVDYTITVYAGVSSYYYYWGSSPISINYRT

Mb(hGPR56_β18)
(SEQ ID NO: 23)
VSSVPTKLEVVAATPTSLLISWDAPAVTVDYYVITYGETGVGWVPGQTF
EVPGSKSTATISGLKPGVDYTITVYAYHEYYFISPISINYRT

Mb(hGPR56_β19)
(SEQ ID NO: 24)
VSSVPTKLEVVAATPTSLLISWDAPAVTVDFYYITYGETGSSYWSYQEF
TVPGSKSTATISGLKPGVDYTITVYAIDQWQYYYYEMGSPISINYRT

Adnectin sequences bind EGF-R.

>pdb13QWQ1B Crystal structure of the extracellular
domain of the epidermal growth factor receptor in
complex with an adnectin
(SEQ ID NO: 25)
MGVSDVPRDLEVVAATPTSLLISWDSGRGSYQYYRITYGETGGNSPVQE
FTVPGPVHTATISGLKPGVDYTITVYAVTDHKPHADGPHTYHESPISIN
YRTEIDKPSQHHHHHH >pdb13QWR1D Crystal structure of IL-23 in complex
with an adnectin
(SEQ ID NO: 26)
MGVSDVPRDLEVVAATPTSLLISWEHDYPYRRYYRITYGETGGNSPVQE
FTVPKDVDTATISGLKPGVDYTITVYAVISSYKYDMQYSPISINYRTEI
DKPSQHHHHHH The following molecule binds PDL-1 (BMS-986192 (US Published Application No. 20190184043A1).

(SEQ ID NO: 27)
EVVAATPTSLLISWSYDGPIDRYYRITYGETGGNSPVQEFTVPPDQKTA
TISGLKPGVDYTITVYAVRLEEAHYNREFPISINYRTPC

In some embodiments, the synthetic binding protein, which can also be the targeting agent, includes an amino acid sequence at least 70, 75, 80, 85, 90, 95, or 100% identical to any one of SEQ ID NOS:6-27.

Affibodies or "antibody mimics" can be generated from the Z domain of protein A from *Staphylococcus aureus* (Sha, et al., Protein Sci. 2017, 26(5), 910-924). Affibodies contain three α-helices, no disulfides, and make up one of the smallest well-characterized synthetic binders (~6 kDa) (Nord, et al., Prot. Eng. 1995, 8, 601-608; Wikman, et al., Protein Eng. Des. Sel. 2004, 17, 455-462; Sandstrom, et al., Protein Eng. 2003, 16, 691-697; Nord, et al., Nat. Biotechnol. 1997, 15, 772-777).

Anticalins are based on lipocalins, and have a β-barrel architecture with an attached α-helix (Sha, et al., Protein Sci. 2017, 26(5), 910-924).

Adnectins are similar to monobodies. Other FN3-based binding proteins, or "monobody mimics" include Centyrins and TN3-based binding proteins (Gilbreth, et al., Protein Eng. Des. Sel. 2014, 27, 411-418; Diem, et al., Protein Eng. Des. Sel. 2014, 27, 419-429).

Designed ankyrin-repeat proteins (DARPins) make use of repetitive structural units to form an extended binding surface (Forrer, et al., FEBS Lett. 2003, 539, 2-6). Although DARPins lack disulfide bonds, they exhibit high thermodynamic stability (Binz, et al., J. Mol. Biol. 2003, 332, 489-503; Kohl, et al., Proc. Natl. Acad. Sci. USA 2003, 100, 1700-1705).

Fynomers are small binding proteins (7 kDa) derived from the human Fyn SH3 domain which can be engineered to bind to essentially any target of interest with high affinity and specificity (Schlatter, et al. MAbs. 2012 Jul.-Aug.;4(4): 497-508. doi: 10.4161/mabs.20452; Silacci, et al., The Journal Of Biological Chemistry 289(20):14392-14398 (2014)).

2. Chemical Moiety Linking Binding Protein

The chemical moiety through which the synthetic binding protein can be connected to the surface of the particles or to nucleic acids or other deliverable can be a natural amino acid, synthetic amino acid, or other small molecule that has been covalently incorporated into the synthetic binding protein. A natural amino acid, synthetic amino acid, or other small molecule can be introduced into the synthetic binding protein via site directed mutagenesis. Exemplary amino acids include, but are not limited to, cysteines, lysines, ornithines, arginines, serines, threonines, and tyrosines. In some forms, the amino acid is a cysteine.

Preferably, the chemical moiety contains a reactive group that is capable of reacting with another chemical moiety located on the surface of the particle or a component of the particle. Suitable reactive chemical groups include, but are not limited to, a thiol; alkyne; azide; maleimide; alkene; triarylphosphine; aminooxy; carbonyl; hydrazide; sulfonyl chloride; maleimide; aziridine; —CN; acryloyl; acrylamide; sulfone; vinyl sulfone; cyanate; thiocyanate; isocyanate; isothiocyanate; alkoxysilane; dialkyl dialkoxysilane; diaryl dialkoxysilane; trialkyl monoalkoxysilane; vinyl silane; acetohydrazide; acyl azide; acyl halides; epoxide; glycidyl; carbodiimides; amine; hydroxyl, phosphoramidate; vinyl ether; substituted hydrazine; an alkylene glycol bis(diester), such as ethylene glycol bis(succinate); thioester, such as alkyl thioester, α-thiophenylester, allyl thioester (such as allyl thioacetae, allyl thioproprionate); allyl ester (such as allyl acetate, allyl propionate); aryl acetate (such as phenacyl ester); orthoester; sulfonamide, such as 2-N-acyl nitrobenzenesulfonamide; vinyl sulfide; or a combination thereof. In some forms, the reactive group is a thiol.

Preferably, the synthetic binding protein (e.g. monobody) is covalently linked to the surface of the particle via a component (such as polymer, lipid, metal, etc.) of the particle.

In some forms, the covalent linkage contains the structure:

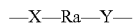    Formula I wherein,
(i) X and Y, independently, contain between 3 and 90 atoms, inclusive, between 3 and 85 atoms, inclusive, between 3 and 80 atoms, inclusive, between 3 and 70 atoms, inclusive, between 3 and 60 atoms, inclusive, between 3 and 50 atoms, inclusive, between 3 and 40 atoms, inclusive, between 3 and 30 atoms, inclusive, or between 3 and 20 atoms, inclusive. Preferably, X and Y, can be independently an organic group such as substituted alkyl; substituted alkylene; unsubstituted alkylene; a polyether, such as poly(ethylene glycol); substituted alkenyl; substituted alkynyl; substituted aryl; substituted heteroaryl; substituted C3-C20 cycloalkyl, substituted C3-$C_{20}$ heterocycyl, or a combination thereof; and
(ii) Ra contains a 3-thiopyrrolidine-2,5-dione moiety (preferably formed from a reaction between a maleimide and a thiol), 3-aminopyrrolidine-2,5-dione moiety (preferably formed from a reaction between a maleimide and a thiol), 3-aminopyrrolidine-2,5-dione moiety (preferably formed from a reaction between a maleimide and an amine), 3-thiomaleimide moiety (preferably formed from a reaction between a 3-halomaleimide and thiol), 3-aminomaleimide moiety (preferably formed from a reaction between a 3-halomaleimide and an amine), a triazole moiety (preferably formed from a reaction between an alkyne and an azide), a carbamate (preferably formed from a reaction between an amine and a hydroxy using diimidazole carbonyl; or a reaction between an isocyanate and a hydroxy), oxime ether (preferably formed from a reaction between a carbonyl and an aminooxy), hydrazone (preferably formed from a reaction between a carbonyl and a hydrazide), a carbonyl (such as a ketone), imine (preferably formed from a reaction between a carbonyl and an amine), sulfonamide (preferably formed from a reaction between a sulfonyl chloride and an amine), azo (preferably formed from a reaction between an aromatic diazonium and anilines or phenols), dialkyl dialkoxysilane, diaryl dialkoxysilane, orthoester, acetal, aconityl, β-thiopropionate, phosphoramidate, trityl, vinyl ether, polyketal, or a combination thereof.

In some forms, the thiol is the sulf-hydryl moiety of a cysteine.

In some forms of Formula I, X contains between 3 and 20 atoms, inclusive. In some forms of Formula I, Y contains between 3 and 10 atoms.

In some forms of Formula I, X and Y independently contain a substituted alkyl, substituted alkylene, unsubstituted alkylene, or substituted aryl.

In some forms of Formula I, Ra contains a 3-thiopyrrolidine-2,5-dione moiety.

In some forms of Formula I, X contains ethylene and Y contains methylene.

In some forms of Formula I, X contains ethylene, Ra contains a 3-thiopyrrolidine-2,5-dione moiety, and Y contains methylene.

In the most preferred embodiments, the linkage is through a unique or singular moiety that ensures proper targeting agent orientation and display. For example, lysines and arginines would be amine linkages that are less specific for use with monobodies, because they may already be present in the sequence of the monobody. However, monobodies have no other cysteines so a single internal or terminal cysteine can provide the only possible site for linkage. Other chemistries that would be similarly specific (e.g. click chemistry) could be introduced, but preferably, lysines or other amino acids that are already present in the synthetic binding protein (e.g., monobody) itself are not utilized because then conjugation may not occur only at the intended site.

In other embodiments, the monobody is re-engineered to include only a single Lys residue and the unique Lys is used for site-specific conjugation.

B. Targeting Agents

The deliverables such as particles and nucleic acids and other deliverables can also include a targeting agent. Preferably, the targeting agent is conjugated to the deliverable via a synthetic binding protein described herein. Alternatively, the synthetic binding protein itself serves the function of the targeting agent. Thus, in some embodiments, the synthetic binding protein binds to a target agent that directs the deliverable such as particles or nucleic acids to the cells or tissue of interest. In some embodiments, the synthetic binding protein is the target agent and no further targeting agent is needed or used.

Synthetic binding proteins with a desired binding function can be engineered by screening phage-display libraries of proteins, preferably those proteins with a globular fold, containing loop regions that can be diversified. Further, a synthetic binding protein can be engineered that binds a specific targeting agent that can target the particles to a desired receptor, cell, or sub-cellular local. Accordingly, the particles can include a wide range of targeting agents. For example, methods of making and/or screening for monobodies with desired binding specificity and activity are discussed in U.S. Pat. Nos. 9,127,090, 8,263,741, 8,106,162, 8,062,858, 7,981,620, 7,858,090, 7,598,352, 7,556,925, 7,153,661, 7,078,490, 6,703,199, 6,673,901, and 6,462,189.

Thus, the binding specificity of the synthetic binding protein, such as a monobody, can be customized by the practitioner.

Monobodies are described in, for example, Gilbreth, et al., *J Mol Biol.* 2008; 381:407-18; Gilbreth, et al., *Proc Nat Acad Sci USA.* 2011; 108:7751-6. Epub 2011/04/27. doi: 10.1073/pnas.1102294108. PubMed PMID: 21518904; PMCID: PMC3093456; Gupta, et al., *Nat Chem Biol.* 2018; 14(9):895-900. Epub 2018/07/18. doi: 10.1038/s41589-018-0099-z. PubMed PMID: 30013062; PMCID: PMC6103845; Koide, et al., *Proc Natl Acad Sci USA.* 2007; 104(16):6632-7. PubMed PMID: 17420456; Koide, et al., *J Mol Biol.* 2012; 415:393-405. Epub 2011/12/27. doi: 10.1016/j.jmb.2011.12.019. PubMed PMID: 22198408; PMCID: 3260337; Nady, et al., *Elife.* 2015; 4:e10150. doi: 10.7554/eLife.10150. PubMed PMID: 26523391; PMCID: 4749557; Salzman, et al., *Neuron.* 2016; 91(6):1292-304. doi: 10.1016/j.neuron.2016.08.022. PubMed PMID: 27657451; Salzman, et al., *Proc Nat Acad Sci USA.* 2017; 114(38): 10095-100. doi: 10.1073/pnas.1708810114. PubMed PMID: 28874577; PMCID: 5617296; Sha, et al., *Proc Natl Acad Sci USA.* 2013; 110(37):14924-9. doi: 10.1073/pnas.1303640110. PubMed PMID: 23980151; PMCID: 3773763; Spencer-Smith, et al., *Nat Chem Biol.* 2017; 13(1):62-8. doi: 10.1038/nchembio.2231. PubMed PMID: 27820802; PMCID: 5193369; Stockridge; *Nat Commun.* 2014; 5:5120; Tanaka, et al., *Nat Chem Biol.* 2015; 11(10): 762-4. doi: 10.1038/nchembio.1896. PubMed PMID: 26322825; Wojcik, et al., *Nat Struct Mol Biol.* 2010; 17(4): 519-27. Epub 2010/04/02. doi: 10.1038/nsmb.1793. PubMed PMID: 20357770; PMCID: 2926940; Wojcik, et al., *J Biol Chem.* 2016; 291(16):8836-47. doi: 10.1074/jbc.M115.707901. PubMed PMID: 26912659; PMCID: 4861451; Zorba, et al., *Proc Natl Acad Sci USA.* 2019; 116(28):13937-42. Epub 2019/06/27. doi: 10.1073/pnas.1906024116. PubMed PMID: 31239342; PMCID: PMC6628680, each of which is specifically incorporated by reference in its entirety.

In some forms, a targeting agent contains a first surface to which the synthetic binding protein has been engineered to bind, preferably with high affinity. Preferably, the targeting agents also contain a second surface that targets an organ, tissue, cell, subcellular locale, or extracellular matrix. Preferably, the second surface is positioned distinct from and non-overlapping with the first surface and separated from the first surface by a portion of the targeting agent. Preferably the binding to the synthetic binding protein to the target agent does prevent the targeting agent from binding its target.

Targeting agents can be peptides such as antibodies, antigen binding fragments, or fusion proteins of an antibody; nucleic acids; glycoproteins; carbohydrates; lipids; or small molecules that bind to one or more targets associated with an organ, tissue, cell, subcellular locale, or extracellular matrix. In some forms, one or more targeting agents can be conjugated to the particles or nucleic acids or other deliverables, preferably non-covalently. In some forms, the targeting agents are peptides. Preferred targeting agents are non-enzymatic molecules, such as antibodies. In the case of an antibody, the Fc region contains the first surface.

Antibodies and fragments that can be used include monoclonal and polyclonal antibodies, single chain antibodies, single chain variable fragments (scFv), di-scFv, tri-scFv, diabody, triabody, teratbody, disulfide-linked Fvs (sdFv), Fab', F(ab')$_2$, Fv, and single domain antibody fragments (sdAb).

In some embodiments, the antibody or antigen binding fragment or fusion or other targeting agent does not initially contain an Fc domain. Such agents can be adapted for use with an Fc-binding monobody by grafting or fusing or conjugating an Fc region thereto. Additionally or alternatively, any targeting agent can become adapted to be a binding partner for a synthetic binding protein such as a monobody, by grafting or fusing or conjugating the targeting agent binding site of the binding protein to the targeting agent.

Non-limiting examples of antibodies include, but are not limited to, those that specifically bind a surface protein receptor, optionally those accessible to the particle or nucleic acid. Examples include, but are not limited to, ICAM1, ICAM2, CD62E, CD34, CD3, CD4, CD8, MHCI, MHCII, and CD31. In some embodiments, the antibodies specifically bind surface receptors basally expressed all the time or upregulated in damage or inflammation.

In the case of antibodies and fragments and fusions thereof, the synthetic binding protein may bind to a feature of the antibody or fragment or fusion that does not impact its binding specificity as a targeting agent. Preferably, the synthetic binding protein binds to a conserved region of the antibody or fragment or fusion. In this way, the same synthetic binding protein (e.g., monobody) may be used to conjugate a plurality of different targeting agents to the same or different particles or nucleic acids or other deliverables. The synthetic binding protein can be designed to bind to any existing antibody species or isotype. When designed to bind a constant or conserved region, the synthetic binding protein can then serve as a linker for all antibodies having the same constant or conserved region, regardless of the antibody's specificity.

In some examples, the synthetic binding protein binds to the Fc region of an antibody. Fc can refer to the last two constant region immunoglobulin domains of IgA, IgD, and IgG, and the last three constant region immunoglobulin domains of IgE and IgM. In a preferred embodiment, the Fc domain is derived from a human or murine immunoglobulin. In a more preferred embodiment, the Fc domain is derived from human IgG1 or murine IgG2a including the $C_H2$ and $C_H3$ regions.

In some embodiments, the antibody is an anti-CD31 antibody (e.g., clone WN59), or an anti-CD3 antibody (e.g., OKT3 ab).

C. Deliverables

The disclosed synthetic binding protein is conjugated to a deliverable. Although preferred deliverables are particles and nucleic acids, direct conjugation to therapeutic, prophylactic, and diagnostic agents including small molecule drugs is also contemplated and can be used in place of the particles or nucleic acid as otherwise disclosed herein with respect to the particles or nucleic acids.

1. Particles

In some forms, the particles can be a matrix of polymers, liposomes, micelles, or inorganic particles.

i. Polymeric Particles

The particles can be formed of one or more biocompatible polymers, preferably biodegradable polymers. The polymers can be hydrophobic, hydrophilic, or amphiphilic polymers that can be broken down hydrolytically or enzymatically in vitro or in vivo. The polymers can be soluble polymers crosslinked by hydrolysable cross-linking groups to render the crosslinked polymer insoluble or sparingly soluble in water. Exemplary polymers are discussed below. Copolymers such as random, block, or graft copolymers, or blends of the polymers listed below can also be used.

The weight average molecular weight can vary for a given polymer but is generally between about 1000 Daltons and 1,000,000 Daltons, between about 1000 Daltons and about 500,000 Dalton, between about 1000 Daltons and about 250,000 Daltons, between about 1000 Daltons and about 100,000 Daltons, between about 5,000 Daltons and about 100,000 Daltons, between about 5,000 Daltons and about 75,000 Daltons, between about 5,000 Daltons and about 50,000 Daltons, or between about 5,000 Daltons and about 25,000 Daltons.

In some forms, the particle contains an amphiphilic polymer containing a hydrophobic polymer portion, a hydrophilic polymer portion, and a synthetic binding protein (such as a monobody) conjugated, preferably covalently, to the hydrophilic polymer portion. In some forms, a targeting agent (such as an antibody) is further conjugated, preferably non-covalently, to the synthetic binding protein. Preferably, the targeting agent is conjugated to the synthetic binding protein via a surface of the synthetic binding protein, which is distinct from (e.g., non-overlapping with) the surface through which the synthetic binding protein is conjugated to the hydrophilic polymer portion.

In some forms, the particle contains a blend of (i) a first amphiphilic polymer containing a hydrophobic polymer portion, a hydrophilic polymer portion, and a synthetic binding protein (such as a monobody) conjugated, preferably covalently, to the hydrophilic polymer portion, and (ii) a second amphiphilic polymer containing a hydrophobic polymer portion, a hydrophilic polymer portion. Preferably, the second amphiphilic polymer does not contain a synthetic binding protein. In some forms, a targeting agent (such as an antibody) is further conjugated, preferably non-covalently, to the synthetic binding protein. Preferably, the targeting agent is conjugated to the synthetic binding protein via a surface of the synthetic binding protein, which is distinct from the surface through which the synthetic binding protein is conjugated to the hydrophilic polymer portion. The hydrophobic polymer portion of the first amphiphilic polymer may or may not be the same as the hydrophobic polymer portion of the second amphiphilic polymer. The hydrophilic polymer portion of the first amphiphilic polymer may or may not be the same as the hydrophilic polymer portion of the second amphiphilic polymer.

In some forms, the particle contains a blend of (i) an amphiphilic polymer containing a hydrophobic polymer portion, a hydrophilic polymer portion, and a synthetic binding protein (such as a monobody) conjugated, preferably covalently, to the hydrophilic polymer portion, and (ii) a hydrophobic polymer. Preferably, the hydrophobic polymer does not contain a synthetic binding protein. In some forms, a targeting agent (such as an antibody) is conjugated, preferably non-covalently, to the synthetic binding protein. Preferably, the targeting agent is conjugated to the synthetic binding protein via a surface of the synthetic binding protein, which is distinct from the surface through which the synthetic binding protein is conjugated to the hydrophilic polymer portion. The hydrophobic polymer portion of the amphiphilic polymer may or may not be the same as the hydrophobic polymer.

In some forms, the particle contains a blend of (i) an amphiphilic polymer containing a hydrophobic polymer portion, a hydrophilic polymer portion, and a synthetic binding protein (such as a monobody) conjugated, preferably covalently, to the hydrophilic polymer portion, and (ii) a hydrophilic polymer. Preferably, the hydrophilic polymer does not contain the synthetic binding protein. In some forms, a targeting agent (such as an antibody) is conjugated, preferably non-covalently, to the synthetic binding protein. Preferably, the targeting agent is conjugated to the synthetic binding protein via a surface of the synthetic binding protein, which is distinct from to the surface through which the synthetic binding protein is conjugated to the hydrophilic polymer portion. The hydrophilic polymer portion of the amphiphilic polymer may or may not be the same as the hydrophilic polymer.

In some forms, the particle contains a blend of (i) an amphiphilic polymer containing a hydrophobic polymer portion, a hydrophilic polymer portion, and (ii) a hydrophilic polymer with a synthetic binding protein (such as a monobody) conjugated, preferably covalently, to the hydrophilic polymer. Preferably, the amphiphilic polymer does not contain the synthetic binding protein. In some forms, a targeting agent (such as an antibody) is conjugated, preferably non-covalently, to the synthetic binding protein. Preferably, the targeting agent is conjugated to the synthetic binding protein via a surface of the synthetic binding protein, which is distinct from the surface through which the synthetic binding protein is conjugated to the hydrophilic polymer. The hydrophilic polymer portion of the amphiphilic polymer may or may not be the same as the hydrophilic polymer.

In some forms, the particle contains a blend of (i) an amphiphilic polymer containing a hydrophobic polymer portion, a hydrophilic polymer portion, and (ii) a hydrophobic polymer with a synthetic binding protein (such as a monobody) conjugated, preferably covalently, to the hydrophobic polymer. Preferably, the amphiphilic polymer does not contain the synthetic binding protein. In some forms, a targeting agent (such as an antibody) is conjugated, preferably non-covalently, to the synthetic binding protein. Preferably, the targeting agent is conjugated to the synthetic binding protein via a surface of the synthetic binding protein, which is distinct from the surface through which the synthetic binding protein is conjugated to the hydrophobic polymer. The hydrophobic polymer portion of the amphiphilic polymer may or may not be the same as the hydrophobic polymer.

In some forms, the particle contains a blend of (i) a hydrophilic polymer with a synthetic binding protein (such as a monobody) conjugated, preferably covalently, to the hydrophilic polymer, and (ii) a hydrophobic polymer. Preferably, the hydrophobic polymer does not contain the synthetic binding protein. In some forms, a targeting agent (such as an antibody) is conjugated, preferably non-covalently, to the synthetic binding protein. Preferably, the targeting agent is conjugated to the synthetic binding protein via a surface of the synthetic binding protein, which is distinct from the surface through which the synthetic binding protein is conjugated to the hydrophobic polymer.

In terms of the differences described above, (i) two hydrophobic polymer portions, (ii) two hydrophilic polymer portions, (iii) a hydrophobic polymer portion and a hydrophobic polymer, or (iv) a hydrophilic polymer portion and a hydrophilic polymer, may have different molecular structures, or the same molecular structures but the same or different molecular weights.

a. Hydrophobic Polymers

The particles can be formed of one or more hydrophobic polymers. In some forms, the hydrophobic polymers are biodegradable.

In some forms, the hydrophobic polymers include polyesters such as polyhydroxy acids (such as poly(lactic acid-co-glycolic acid)s, poly(lactic acid)s, poly(glycolic acid)s), polycaprolactones, polyhydroxyalkanoates (such as poly-3-hydroxybutyrate, poly4-hydroxybutyrate, polyhydroxyvalerates), poly(lactide-co-caprolactones); poly(anhydride)s; poly(orthoester)s; poly(beta-amino ester)s; poly(amine-co-ester)s; poly(amine-co-ester-co-ortho ester)s, and copolymers thereof.

Poly(amine-co-ester) and poly(amine-co-ester-co-ortho ester)particles and polyplexes formed therefrom are disclosed in WO 2013/082529, WO 2016/183217, U.S. Published Application No. 2016/0251477, U.S. Published Application No. 2015/0073041, and U.S. Pat. No. 9,272,043, each of which is specifically incorporated by reference in entirety.

In some forms, the hydrophobic polymers are polyesters, preferably polyhydroxy acids such as poly(lactic acid-co-glycolic acid)s, poly(lactic acid)s, or poly(glycolic acid)s.

b. Hydrophilic Polymers

The particles can contain one or more hydrophilic polymers. Preferably, the hydrophilic polymers are biodegradable. Hydrophilic polymers include polyalkylene glycol such as polyethylene glycol (PEG); polysaccharides such as cellulose and starch and derivatives thereof; hydrophilic polypeptides such as poly-L-glutamic acids, gamma-polyglutamic acids, poly-L-aspartic acids, poly-L-serines, or poly-L-lysines; poly(oxyethylated polyol)s; poly(olefinic alcohol)s such as poly(vinyl alcohol)s; poly(vinylpyrrolidone)s; poly(N-hydroxyalkyl methacrylamide)s such as poly (N-hydroxyethyl methacrylamide)s; poly(N-hydroxyalkyl methacrylate)s such as poly(N-hydroxyethyl methacrylate)s; hydrophilic poly(hydroxy acids); and copolymers thereof. In some forms, the hydrophilic polymer is a polyalkylene glycol such as PEG or a poloxamer.

c. Amphiphilic Polymers

The particles can contain one or more amphiphilic polymers, preferably biodegradable amphiphilic polymers. The amphiphilic polymers contain a hydrophobic polymer portion and a hydrophilic polymer portion. The hydrophobic polymer portion and hydrophilic polymer portion can include any of the hydrophobic polymers and hydrophilic polymers, respectively, described above.

In a non-limiting example, the hydrophobic polymer portion is a polymer formed from polyesters such as poly-hydroxy acids (such as poly(lactic acid)s, poly(glycolic acid)s, and poly(lactic acid-co-glycolic acid)s), polycaprolactones, polyhydroxyalkanoates (such as poly-3-hydroxybutyrate, poly4-hydroxybutyrate, polyhydroxyvalerates), poly(lactide-co-caprolactones); poly(anhydride); poly(or-thoester)s; and hydrophobic polyethers (such as polypropylene glycol); as well as copolymers thereof. The hydrophilic polymer portion can contain a polymer such as a polyalkylene oxide such as polyethylene glycol (PEG); polysaccharides such as cellulose and starch; hydrophilic polypeptides such as poly-L-glutamic acids, gamma-polyglutamic acids, poly-L-aspartic acids, poly-L-serines, or poly-L-lysines; poly(oxyethylated polyol)s; poly(olefinic alcohol)s such as poly(vinyl alcohol)s; poly(vinylpyrrolidone)s; polyacrylamides or polymethaacrylamides including poly(N-hydroxyalkyl methacrylamides) such as poly(N-hydroxyethyl methacrylamide)s; poly(N-hydroxyalkyl methacrylates) such as poly(N-hydroxyethyl methacrylate)s; hydrophilic poly(hydroxy acids); and copolymers thereof.

In some forms, hydrophobic polymer portion contains polyesters (such as poly(lactic acid)s, poly(glycolic acid)s, and poly(lactic acid-co-glycolic acid)s), and the hydrophilic polymer portion contains polyethylene glycols.

Examples of amphiphilic polymers that can be generated from this group include polyester-PEG copolymers such as poly(lactic acid-co-glycolic acid)-PEG (PLGA-PEG), poly(lactic acid)-PEG (PLA-PEG), poly(glycolic acid)-PEG (PGA-PEG), and polycaprolactone-PEG (PCL-PEG); and hydrophobic polyethers-PEG, such as polypropylene glycol-PEG (PPG-PEG), PEG-PPG-PEG, PPG-PEG-PPG. In some forms, the amphiphilic polymer is PLA-PEG.

A shell can also be formed of or contain a hyperbranched polymer (HP) with hydroxyl groups, such as a hyperbranched polyglycerol (HPG), hyperbranched peptides (HPP), hyperbranched oligonucleotides (HON), hyperbranched polysaccharides (HPS), and hyperbranched polyunsaturated or saturated fatty acids (HPF). The HP can be covalently bound to the one or more materials that form the core such that the hydrophilic HP is oriented towards the outside of the particles and the hydrophobic material oriented to form the core.

The HP coating can be modified to adjust the properties of the particles. For example, unmodified HP coatings impart stealth properties to the particles which resist non-specific protein absorption and are referred to as nonbioadhesive nanoparticles (NNPs). Alternatively, the hydroxyl groups on the HP coating can be chemically modified to form functional groups that react with functional groups on tissue or otherwise interact with tissue to adhere the particles to the tissue, cells, or extracellular materials, such as proteins. Such functional groups include, but are not limited to, aldehydes, amines, and 0-substituted oximes. Particles with an HP coating chemically modified to form functional groups are referred to as bioadhesive nanoparticles (BNPs). The chemically modified HP coating of BNPs forms a bioadhesive corona of the particle surrounding the hydrophobic material forming the core. See, for example, WO 2015/172149, WO 2015/172153, WO 2016/183209, and U.S. Published Applications 2017/0000737 and 2017/0266119.

ii. Liposomes and Micelles

In some forms, the particles can be liposomal vesicles, lipid micelles, or solid lipid particles, or a combination thereof. The particles can contain one or more lipids or amphiphilic compounds. The particles are preferably made from one or more biocompatible lipids. The particles can be made from one or a mixture of different lipids that can be neutral, anionic, or cationic at physiologic pH (such as pH 7.4). As a non-limiting example, a charged lipid may be combined with a lipid that is non-ionic or uncharged at physiological pH.

In some forms, the particle can be a lipid micelle. Lipid micelles for delivery of therapeutic, diagnostic, and/or prophylactic agents are known in the art. Lipid micelles can be formed, for instance, as a water-in-oil emulsion with a lipid surfactant. An emulsion is a blend of two immiscible phases wherein a surfactant is added to stabilize the dispersed droplets. The lipid micelle can be a microemulsion. A microemulsion is a thermodynamically stable system composed of at least water, oil, and a lipid surfactant producing a transparent and thermodynamically stable system whose droplet size is less than 1 micron, from about 10 nm to about 500 nm, or from about 10 nm to about 250 nm. Lipid micelles are generally useful for encapsulating hydrophobic active agents, including hydrophobic therapeutic agents, hydrophobic prophylactic agents, or hydrophobic diagnostic agents.

In some forms, the particle can be a liposome, such as a liposomal vesicle. Liposomal vesicles typically contain an aqueous medium surrounded by lipids arranged in spherical bilayers. Liposomal vesicles can be classified as small unilamellar vesicles, large unilamellar vesicles, or multi-lamellar vesicles. Multi-lamellar liposomes contain multiple concentric lipid bilayers. Liposomes can be used to encapsulate therapeutic, diagnostic, and or prophylactic agents, by trapping hydrophilic agents in the aqueous interior or between bilayers, or by trapping hydrophobic agents within the bilayer.

The lipid micelles and liposomes typically have an aqueous center. The aqueous center can contain water or a mixture of water and alcohol. Suitable alcohols include, but are not limited to, methanol, ethanol, propanol, (such as isopropanol), butanol (such as n-butanol, isobutanol, sec-butanol, tert-butanol, pentanol (such as amyl alcohol, isobutyl carbinol), hexanol (such as 1-hexanol, 2-hexanol, 3-hexanol), heptanol (such as 1-heptanol, 2-heptanol, 3-heptanol and 4-heptanol) or octanol (such as 1-octanol) or a combination thereof.

In some forms, the particle can be a solid lipid particle. Solid lipid particles present an alternative to the colloidal micelles and liposomal vesicles. Solid lipid particles are typically submicron in size, i.e. from about 10 nm to about 1 micron, from 10 nm to about 500 nm, or from 10 nm to about 250 nm. Solid lipid particles can be formed of lipids that are solids at room temperature. They are derived from oil-in-water emulsions, by replacing the liquid oil by a solid lipid.

Suitable neutral and anionic lipids include, but are not limited to, sterols and lipids such as cholesterol, phospholipids, lysolipids, lysophospholipids, sphingolipids or pegylated lipids. Neutral and anionic lipids include, but are not limited to, phosphatidylcholine (PC) (such as egg PC, soy PC), including 1,2-diacyl-glycero-3-phosphocholines; phosphatidylserine (PS), phosphatidylglycerol, phosphatidylinositol (PI); glycolipids; sphingophospholipids such as sphingomyelin and sphingoglycolipids (also known as 1-ceramidyl glucosides) such as ceramide galactopyranoside, gangliosides and cerebrosides; fatty acids, sterols, containing a carboxylic acid group for example, cholesterol; 1,2-diacyl-sn-glycero-3-phosphoethanolamine, including, but not limited to, 1,2-dioleylphosphoethanolamine (DOPE), 1,2-dihexadecylphosphoethanolamine (DHPE), 1,2-distearoylphosphatidylcholine (DSPC), 1,2-dipalmitoyl phosphatidylcholine (DPPC), and 1,2-dimyristoylphosphatidylcholine (DMPC). The lipids can also include various natural (e.g., tissue derived L-.alpha.-phosphatidyl: egg yolk, heart, brain, liver, soybean) and/or synthetic (e.g., saturated and unsaturated 1,2-diacyl-sn-glycero-3-phosphocholines, 1-acyl-2-acyl-sn-glycero-3-phosphocholines, 1,2-diheptanoyl-SN-glycero-3-phosphocholine) derivatives of the lipids.

Suitable cationic lipids include, but are not limited to, N-[1-(2,3-dioleoyloxy)propyl]-N,N,N-trimethyl ammonium salts, also references as TAP lipids, for example methylsulfate salt. Suitable TAP lipids include, but are not limited to, DOTAP (dioleoyl-), DMTAP (dimyristoyl-), DPTAP (dipalmitoyl-), and DSTAP (distearoyl-). Suitable cationic lipids in the liposomes include, but are not limited to, dimethyldioctadecyl ammonium bromide (DDAB), 1,2-diacyloxy-3-trimethylammonium propanes, N-[1-(2,3-diololyoxy) propyl]-N,N-dimethyl amine (DODAP), 1,2-diacyloxy-3-dimethylammonium propanes, N-[1-(2,3-dioleyloxy) propyl]-N,N,N-trimethylammonium chloride (DOTMA), 1,2-dialkyloxy-3-dimethylammonium propanes, dioctadecylamidoglycylspermine (DOGS), 3-[N-(N',N'-dimethylamino-ethane)carbamoyl]cholesterol (DC-Chol); 2,3-dioleoyloxy-N-(2-(sperminecarboxamido)-ethyl)-N,N-dimethyl-1-propanam-inium trifluoro-acetate (DOSPA), .beta.-alanyl cholesterol, cetyl trimethyl ammonium bromide (CTAB), diC.sub.14-amidine, N-ferf-butyl-N'-tetradecyl-3-tetradecylamino-propionamidine, N-(alpha-trimethylammonioacetyl)didodecyl-D-glutamate chloride (TMAG), ditetradecanoyl-N-(trimethylammonio-acetyl)diethanolamine chloride, 1,3-dioleoyloxy-2-(6-carboxy-spermyl)-propylamide (DOSPER), and N,N,N',N'-tetramethyl-, N'-bis(2-hydroxylethyl)-2,3-dioleoyloxy-1,4-butanediammonium iodide. In one embodiment, the cationic lipids can be 1-[2-(acyloxy)ethyl]2-alkyl(alkenyl)-3-(2-hydroxyethyl)-imidazolinium chloride derivatives, for example, 1-[2-(9(Z)-octadecenoyloxy)ethyl]-2-(8(Z)-heptadecenyl-3-(2-hydroxyethyl)-imidazolinium chloride (DOTIM), and 1-[2-(hexadecanoyloxy)ethyl]-2-pentadecyl-3-(2-hydroxyethyl)imidazolinium chloride (DPTIM). In one embodiment, the cationic lipids can be 2,3-dialkyloxypropyl quaternary ammonium compound derivatives containing a hydroxyalkyl moiety on the quaternary amine, for example, 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dioleyloxypropyl-3-dimetyl-hydroxypropyl ammonium bromide (DORIE-HP), 1,2-dioleyl-oxy-propyl-3-dimethyl-hydroxybutyl ammonium bromide (DORIE-HB), 1,2-dioleyloxypropyl-3-dimethyl-hydroxypentyl ammonium bromide (DORIE-Hpe), 1,2-dimyristyloxypropyl-3-dimethyl-hydroxylethyl ammonium bromide (DMRIE), 1,2-dipalmityloxypropyl-3-dimethyl-hydroxyethyl ammonium bromide (DPRIE), and 1,2-disteryloxypropyl-3-dimethyl-hydroxyethyl ammonium bromide (DSRIE).

Suitable solid lipids include, but are not limited to, higher saturated alcohols, higher fatty acids, sphingolipids, synthetic esters, and mono-, di-, and triglycerides of higher saturated fatty acids. Solid lipids can include aliphatic alcohols having 10-40, preferably 12-30 carbon atoms, such as cetostearyl alcohol. Solid lipids can include higher fatty acids of 10-40, preferably 12-30 carbon atoms, such as stearic acid, palmitic acid, decanoic acid, and behenic acid. Solid lipids can include glycerides, including monoglycerides, diglycerides, and triglycerides, of higher saturated fatty acids having 10-40, preferably 12-30 carbon atoms, such as glyceryl monostearate, glycerol behenate, glycerol palmitostearate, glycerol trilaurate, tricaprin, trilaurin, trimyristin, tripalmitin, tristearin, and hydrogenated castor oil. Suitable solid lipids can include cetyl palmitate, beeswax, or cyclodextrin.

Amphiphilic compounds include, but are not limited to, phospholipids, such as 1,2 distearoyl-sn-glycero-3-phosphoethanolamine (DSPE), dipalmitoylphosphatidylcholine (DPPC), distearoylphosphatidylcholine (DSPC), diarachidoylphosphatidylcholine (DAPC), dibehenoylphosphatidylcholine (DBPC), ditricosanoylphosphatidylcholine (DTPC), and dilignoceroylphatidylcholine (DLPC), incorporated at a ratio of between 0.01-60 (weight lipid/w polymer), most preferably between 0.1-30 (weight lipid/w polymer). Phospholipids which may be used include, but are not limited to, phosphatidic acids, phosphatidyl cholines with both saturated and unsaturated lipids, phosphatidyl ethanolamines, phosphatidylglycerols, phosphatidylserines, phosphatidylinositols, lysophosphatidyl derivatives, cardiolipin, and .beta.-acyl-y-alkyl phospholipids. Examples of phospholipids include, but are not limited to, phosphatidylcholines such as dioleoylphosphatidylcholine, dimyristoylphosphatidylcholine, dipentadecanoylphosphatidylcholine dilauroylphosphatidylcholine, dipalmitoylphosphatidylcholine (DPPC), distearoylphosphatidylcholine (DSPC), diarachidoylphosphatidylcholine (DAPC), dibehenoylphosphatidylcho-line (DBPC), ditricosanoylphosphatidylcholine (DTPC), dilignoceroylphatidylcholine (DLPC); and phosphatidylethanolamines such as dioleoylphosphatidylethanolamine or 1-hexadecyl-2-palmitoylglycerophos-phoethanolamine. Synthetic phospholipids with asymmetric acyl chains (e.g., with one acyl chain of 6 carbons and another acyl chain of 12 carbons) may also be used.

In some forms, the liposomes can be coated with a water-soluble, biocompatible polymer. Suitable polymers include, but are not limited to polyalkylene oxides such as polyethylene glycol (PEG), polyethylene glycol-polypropylene block copolymer such as a PLURONIC®, poly(N-isopropylacrylamide) (PNIPAM), polyacrylamide (PAM), poly(carboxybetaine)s (pCB), poly(sulfobetaine)s (pSB), poly(phosphobetaine)s, and polyethyleneimine (PEI). In some forms, the polymer can be polyethylene glycol forming coated liposomes collectively known as PEGylated liposomes.

iii. Inorganic Particles

In some forms, the particles can be of an inorganic composition including, but not limited to, quantum dots; minerals, including silica, silicates, oxides, halides, carbonates, sulfates, phosphates; and iron(II) oxide, iron(III) oxide. In some forms, the particles can also be made of one or more metals, such as gold, silver, copper, platinum, palladium, ruthenium, or a combination thereof.

iv. Particle Size

The size of the particles can vary. In some forms the particles can be microparticles having a diameter of at least 1 μm and less than 1000 μm. In some forms, the particles are nanoparticles having a diameter greater than 1 nm and less than 1000 nm.

In some embodiments, the particles are 1 nm to 500 nm, 1 nm to 250 nm, 5 nm to 100 nm, or 10 nm to 50 nm, each inclusive.

In some embodiments, particle size is measured by dynamic light scattering (DLS) or transmission electron microscopy (TEM).

In the experiments below PLA-PEG-MAL:PLA-PEG-M had a size of ~170 nm, ~0.15 pdi, and −5 mV zeta potential. The change in hydrodynamic radius due to addition of monobody and antibody is believed to be not more than about 10-15 nm.

In other examples, the particles are PACE: size 340 nm PdI: 0.17 Zeta: 20 mV, and Gold: commercially available at 30 nm 2. Nucleic Acids In some embodiments, the synthetic binding protein is conjugated directly to a nucleic acid. In some embodiments, particles do not form part of the composition. The nucleic acid conjugates can be single stranded or double stranded and include DNA, RNA, nucleic acid analogs, or a combination thereof. Nucleic acid analogs can be modified at the base moiety, sugar moiety, or phosphate backbone. Such modification can improve, for example, stability, hybridization, or solubility of the nucleic acid. Exemplary nucleic acids, include, but are not limited to mRNA or DNA encoding polypeptides of interest including, for example expression constructs and vectors, inhibitory nucleic acids such as antisense molecules, siRNA, miRNA, aptamers, ribozymes, RNAi, and external guide sequences, and nucleic acids encoding the inhibitory nucleic acid including, for example expression constructs and vectors. Exemplary modifications include, but are not limited to, phosphorothioates, neutral backbones, 2' modifications, and bridged rings (Juliano, et al., *Nucleic Acids Research*, 44(14):6518-6548 (2016)).

Any of the foregoing nucleic acids can also serve as cargo in synthetic binding protein conjugated particles.

3. Other Deliverables

In addition to particles and nucleic acids, the synthetic binding protein can alternatively be conjugated to other deliverables to enhance targeting of therapeutic, nutritional, diagnostic, and prophylactic compounds. These same agents can also serve as cargo for the particles.

In some forms, the deliverable agents or cargo can be, independently, nucleic acids, proteins, peptides, carbohydrates, lipids, polysaccharides, small molecules, or a combination thereof. In a particular embodiments, the agent is a radio active therapeutic or diagnostic.

Exemplary materials include drugs and imaging agents. Therapeutic agents include antibiotics, antivirals, anti-parasites (helminths, protozoans), anti-cancer (referred to herein as "chemotherapeutics", including cytotoxic drugs such as doxorubicin, cyclosporine, mitomycin C, cisplatin and carboplatin, BCNU, 5FU, methotrexate, adriamycin, camptothecin, epothilones A-F, and taxol), antibodies and bioactive fragments thereof (including humanized, single chain, and chimeric antibodies), antigen and vaccine formulations, peptide drugs, anti-inflammatories, nutraceuticals such as vitamins, and oligonucleotide drugs (including DNA, RNAs, antisense, aptamers, ribozymes, external guide sequences for ribonuclease P, and triplex forming agents as discussed above).

Particularly preferred drugs to be delivered include antiangiogenic agents, antiproliferative and chemotherapeutic agents such as rampamycin. Incorporated into microparticles, these agents may be used to treat cancer or eye diseases, or prevent restenosis following administration into the blood vessels.

Representative classes of diagnostic materials include paramagnetic molecules, fluorescent compounds, magnetic molecules, and radionuclides. Biomarkers can also be conjugated for diagnostic applications.

D. Pharmaceutical Compositions

Pharmaceutical compositions containing the particles and/or nucleic acids and/or other deliverables can be formulated for parenteral administration. The formulations are designed according to the route of administration and can be formulated in dosage forms appropriate for each route of administration. The compositions are typically administered by intravenous, or subcutaneous, intramuscular injection or intranasal or pulmonary formulations. They may also be fabricated for oral delivery, if delivered in an enteric capsule.

The formulation can be in the form of a suspension or emulsion. In general, pharmaceutical compositions are provided including effective amounts of the therapeutic, diagnostic, and/or prophylactic agents and optionally include pharmaceutically acceptable diluents, preservatives, solubilizers, emulsifiers, and/or carriers. Such compositions include sterile water, buffered saline of various buffer content (such as, Tris HCl, acetate, phosphate), pH and ionic strength; and optionally, additives such as detergents and solubilizing agents (such as, TWEEN® 20, TWEEN® 80 also referred to as polysorbate 20 or 80), anti-oxidants (such as, ascorbic acid, sodium metabisulfite), and preservatives. Preferably, the suspension or emulsion include water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate. Examples of non-aqueous solvents or vehicles are propylene glycol, polyethylene glycol, vegetable oils, such as olive oil and corn oil, gelatin, and injectable organic esters such as ethyl oleate.

The term aerosol as used herein refers to any preparation of a fine mist of particles or nucleic acids or other deliverables, which can be in emulsion or a suspension, whether or not it is produced using a propellant. Aerosols can be produced using standard techniques, such as ultrasonication or high-pressure treatment.

Carriers for pulmonary formulations can be divided into those for dry powder formulations and for administration as emulsion or suspension. Aerosols for the delivery of therapeutic agents to the respiratory tract are known in the art. For administration via the upper respiratory tract, the formulation can be formulated into an emulsion or a suspension containing an aqueous component, such as, water or isotonic saline, buffered or un-buffered, or as a suspension, for intranasal administration as drops or as a spray. One skilled in the art can readily determine a suitable saline content and pH for an innocuous emulsion or a suspension for nasal and/or upper respiratory administration.

The formulations may be lyophilized and redissolved or resuspended immediately before use. The formulation may be sterilized by, for example, filtration through a bacteria retaining filter, by incorporating sterilizing agents into the compositions, by irradiating the compositions, or by heating the compositions.

III. Methods of Making and Reagents Therefor

Methods of making the particles and nucleic acids and components thereof are also provided.

A. Particles

1. Polymeric Particles

Self-Assembly

In some forms, the particles are formed by self-assembly of amphiphilic block copolymers or a blend of polymers in an aqueous solution. In some forms, the blend contains amphiphilic block copolymers. In an aqueous environment, the amphiphilic block copolymers or blend can spontaneously self-assemble to form particles with a hydrophobic core and a hydrophilic outer shell. In some forms, a solution containing the amphiphilic polymers or blend can be mixed with another solution containing a therapeutic, diagnostic, and/or prophylactic agent to be delivered. In some forms, the amphiphilic polymers or blend and therapeutic, diagnostic, and/or prophylactic agent to be delivered are dissolved in a suitable solvent, such as tetrahydrofuran, DMSO, or methylene chloride. The concentrations of the amphiphilic polymer or blend and therapeutic, diagnostic, and/or prophylactic agent in the solvent can be varied as needed. After forming a solution containing the amphiphilic polymer or blend and optionally the therapeutic, diagnostic, and/or prophylactic agent, the solution can be added continuously to an aqueous solution to induce particle formation (micellization). The particle suspensions can be stirred at room temperature, followed by dialysis or tangential flow filtration, placement in an ultrafiltration centrifuge tube, and centrifuging to obtain the particles.

In the case of a blend, two or more polymers can be mixed at a defined percent weight/weight or molar ratio prior to forming the particles. In these forms, at least one type of polymer in the blend contains or will be employed to conjugate the synthetic binding protein (such as a monobody), and optionally the targeting agent (such as an antibody).

In the experiments below, the particles were formed first from a mixture of polymers (e.g., either terminated with the Maleimide functional group or an inert methoxy terminus), and then synthetic binding proteins (e.g., monobodies) were coupled to the particles.

Other Methods of Forming Particles

The particles described herein can be formed using a variety of techniques known in the art. The technique to be used can depend on a variety of factors including the polymer used to form the particles, the desired size range of the resulting particles, and suitability for the therapeutic, diagnostic, and/or prophylactic agent to be incorporated. Suitable techniques include, but are not Limited to:

i. Solvent Evaporation

In this method the polymer is dissolved in a volatile organic solvent. The drug (either soluble or dispersed as fine particles) is added to the solution, and the mixture is suspended in an aqueous solution that contains a surface active agent such as poly(vinyl alcohol). The resulting emulsion is stirred until most of the organic solvent evaporated, leaving solid nanoparticles. The resulting nanoparticles are washed with water and dried overnight in a lyophilizer. Nanoparticles with different sizes and morphologies can be obtained by this method.

ii. Solvent Removal

In this method, the drug is dispersed or dissolved in a solution of the selected polymer in a volatile organic solvent. This mixture is suspended by stirring in an organic oil (such as silicon oil) to form an emulsion. Unlike solvent evaporation, this method can be used to make nanoparticles from polymers with high melting points and different molecular weights. The external morphology of spheres produced with this technique is highly dependent on the type of polymer used.

iii. Spray-Drying

In this method, the polymer is dissolved in organic solvent. A known amount of the active drug is suspended (insoluble drugs) or co-dissolved (soluble drugs) in the polymer solution. The solution or the dispersion is then spray-dried.

iv. Phase Inversion

Nanospheres can be formed from polymers using a phase inversion method wherein a polymer is dissolved in a "good" solvent, fine particles of a substance to be incorporated, such as a drug, are mixed or dissolved in the polymer solution, and the mixture is poured into a strong non solvent for the polymer, to spontaneously produce, under favorable conditions, polymeric microspheres, wherein the polymer is either coated with the particles or the particles are dispersed in the polymer. The method can be used to produce nanoparticles in a wide range of sizes, including, for example, about 100 nanometers to about 10 microns. Substances which can be incorporated include, for example, imaging agents such as fluorescent dyes, or biologically active molecules such as proteins or nucleic acids. In the process, the polymer is dissolved in an organic solvent and then contacted with a non-solvent, which causes phase inversion of the dissolved polymer to form small spherical particles, with a narrow size distribution optionally incorporating an antigen or other substance.

v. Microfluidics

Methods of making nanoparticles using microfluidics are known in the art. Suitable methods include those described in U.S. Patent Application Publication No. 2010/0022680

A1 by Karnik, et al. In general, the microfluidic device comprises at least two channels that converge into a mixing apparatus. The channels are typically formed by lithography, etching, embossing, or molding of a polymeric surface. A source of fluid is attached to each channel, and the application of pressure to the source causes the flow of the fluid in the channel. The pressure may be applied by a syringe, a pump, and/or gravity. The inlet streams of solutions with polymer, targeting moieties, lipids, drug, payload, etc. converge and mix, and the resulting mixture is combined with a polymer non-solvent solution to form the nanoparticles having the desired size and density of moieties on the surface. By varying the pressure and flow rate in the inlet channels and the nature and composition of the fluid sources nanoparticles can be produced having reproducible size and structure.

vi. Nanoprecipitation

In some forms, the nanoparticles can be prepared via the nanoprecipitation approach. In this method, water-soluble or water-miscible organic solvents are used to dissolve the polymer and form emulsion upon mixing with the aqueous phase preferably under moderate stirring. The quick diffusion of the organic solvent into water leads to the formation of nanoparticles immediately after the mixing. After formation of nanoparticles, the solvents can be removed under low/reduced pressure. Nanoprecipitation can be used to encapsulate hydrophobic or hydrophilic compounds, although the method is typically used to encapsulate hydrophobic compounds.

2. Liposomal Particles

Suitable methods, materials and lipids for making liposomes are known in the art. Liposome delivery vehicles are commercially available from multiple sources. Commercially available liposome preparations such as LIPOFECTIN, LIPOFECTAMINE (GIBCO-BRL, Inc., Gaithersburg, Md.), SUPERFECT (Qiagen, Inc. Hilden, Germany) and TRANSFECTAM (Promega Biotec, Inc., Madison, Wis.), as well as other liposomes developed according to procedures standard in the art are well known. For example, liposomes can be prepared by modified thin lipid film hydration (Szoka, et al., *Annual review of biophysics and bioengineering,* 9:467-508 (1980).

3. Inorganic Particles

The inorganic particles described herein can be manufactured using well-established methods in the art, such as vapor-phase synthesis, liquid-phase synthesis, solid-phase synthesis, or a combination thereof. Some methods are described in Tsuzuki, Int. J. Nanotechnol. 2009, 6(5/6), 567-578, the contents of which are herein incorporated by reference.

B. Synthetic Binding Proteins and Conjugation

Methods of making synthetic binding proteins are known in the art. These methods are described in Sha, et al., Protein Sci. 2017, 26(5), 910-924, Koide, et al., Proc. Natl. Acad. Sci. USA 2002, 99(3), 1253-1258, and Koide, et al., *J Mol Biol.* 2012; 415:393-405. Epub 2011/12/27. doi: 10.1016/j.jmb.2011.12.019. PubMed PMID: 22198408, the contents of which are herein incorporated by reference. In general, synthetic binding proteins are usually generated by introducing one or more mutations in a protein scaffold. Using directed evolution approaches, including those that employ molecular display technologies, a combinatorial phage-display library of mutants can be generated, from which synthetic binding proteins can be isolated with a certain level of affinity for a target molecule of interest. Sha, et al., Protein Sci. 2017, 26(5), 910-924. Exemplary $K_D$'s can be as low as between 1 nM and 100 nM (Sha, et al., Protein Sci. 2017, 26(5), 910-924), or even less, such as 500 μM.

The synthetic binding protein (such as a monobody) can be conjugated to the polymer or other component of the particle, optionally followed by conjugating the targeting agent (such as an antibody) to the synthetic binding protein, prior to or after forming the particle. Preferably, conjugation of the synthetic binding protein (such as a monobody) involves covalent linkage. Preferably, conjugation of the targeting agent (such as an antibody) involves non-covalent linkage.

In some forms, prior to conjugating the synthetic binding protein (such as a monobody) to the polymer or other component of the particle, optionally followed by conjugating the targeting agent (such as an antibody) to the synthetic binding protein, the polymer or other component of the particle to which conjugation will occur has a percent wt/wt ratio between about 10% wt/wt and about 100% wt/wt relative to the polymer or other component not intended for conjugation. Exemplary percent wt/wt ratios include 10%, 20%, 30%, 40%, and 50%.

In some embodiments, synthetic binding proteins can be linked to NPs formulated with surfactants by use of PVA-vinyl sulfone. The Examples below illustrate this with PACE particles (Kauffman, et al., *Biomacromolecules* 2018, 19, 9, 3861; Zhou, et al., *Nat Mater.* 2012 January; 11(1): 82-90), and can also be used for other particles formulated in a similar fashion (e.g., PLGA, etc). The particles are made first with the PVA-vinyl sulfone and then synthetic binding proteins are added afterwards which link to the PVA-vinyl sulfone present on the surface of the particles.

Gold particles terminated with suitable chemistries can also be used.

Synthetic binding proteins can be conjugated to nucleic acids and other deliverables using a similar linker strategy, e.g., using a cysteine.

There are numerous synthetic paths for the preparation of oligonucleotide conjugates, as discussed at length in recent reviews, including 'click' chemistry (Juliano, et al., *Nucleic Acids Research,* 44(14):6518-6548 (2016)) Phelps, et al., ACS Chem. Biol. 2012 7 100109, Juliano, et al., Chem. Res. 2012 45 10671076, Lonnberg, et al., Bioconjug. Chem. 2009 20 10651094, Winkler, et al., Ther. Deliv. 2013 4 791809, Yamada, et al., J. Org. Chem. 2011 76 11981211, Willibald, et al., J. Am. Chem. Soc. 2012 134 1233012333, and Shabanpoor, et al., Nucleic Acids Res. 2015 43 2939). However, the bond formed is not bioreversible. More traditional linkages include disulfide bridges and pH sensitive ester linkages that provide reversibility within the cell.

IV. Methods of Using

This platform technology has a wide range of applications, material choices, and application locations, for delivery of therapeutic agents, diagnostic agents, and/or prophylactic agents to cells and microenvironments in need thereof. It can be particularly useful in the controlled release of these agents in a targeted manner. Because of the unique structural and functional (such as targeting agent binding) features of the synthetic binding proteins, the particles exhibit significantly higher targeting to desired sites compared to particles that do not contain a synthetic binding protein.

The methods of treatment typically include using nucleic acid conjugate active agents, or particles loaded with one or more active agents, or other directly conjugated active agent to deliver the one or more active agents into cells, or to a cell's microenvironment. The methods typically include contacting the active agent-loaded particles or nucleic acid conjugates or other deliverables with one more cells or introducing them into a desired microenvironment. The contacting or introducing can occur in vivo or in vitro or ex vivo.

In some embodiments, particles or nucleic acids or other deliverables including a synthetic binding protein linked to a targeting agent are contacted with cells, administered to a subject, or introduced to microenvironment. In other embodiments, the target agent is first contacted with cells, administered to a subject, or introduced to microenvironment, and particles or nucleic acids or other deliverables including a synthetic binding protein are next contacted with cells, administered to a subject, or introduced to microenvironment. When the synthetic binding protein encounters the target agent it binds thereto and complete the targeting of the particle or nucleic acid conjugate. When the binding protein recognizes a common structure in the target agents such as the Fc region of an antibody targeting agent, multiple different target agents can be administered, and a single species of synthetic binding protein conjugated particles or nucleic acids or other deliverables can bind to all of them. In this way, multiple low-expression receptors can be simultaneously targeted to, e.g., amplify the active agent delivered to a target location.

Administration of a drug or other cargo to cells or a subject using particles can be compared to a control, for example, delivery of the drug or other cargo to cells or a subject using conventional delivery methods such as free cargo/drug delivery, delivery using untargeted particles or nucleic acids or other deliverables, or particles or nucleic acids or other deliverables targeted with antibodies conjugated directly to particles or nucleic acids or other deliverables using traditional methodologies and/or absent a synthetic binding protein such as a monobody. Particles and nucleic acid conjugates and other deliverables can be used to deliver cargo to target cells with increased efficacy compared to conventional delivery methods. In some embodiments less cargo or drug is required when delivered using disclosed particles or nucleic acids or other deliverable compared to conventional delivery methods to achieve the same or greater therapeutic benefit.

In some embodiments toxicity is reduced or absent compared to conventional delivery methods.

In some embodiments, the compositions and methods enhance delivery of agents to endothelial cells, which, as exemplified below, can be targeted using e.g., anti-CD31 or ICAM antibodies as targeting moieties. They are a valuable therapeutic target for multiple severe pathologies such as cancers, strokes, thrombosis, ischemia reperfusion injury and many others. In the context of transplant, efficiently delivering therapeutics to the graft endothelial cells could potentially render organs more resistant to injury, thus improving clinical outcomes and access to transplant by making more organs suitable for clinical use.

A. In vivo Methods

The disclosed compositions can be used in a method of delivering active agents to cells in vivo. In some in vivo approaches, the compositions are administered to a subject in a therapeutically effective amount. As used herein, the term "effective amount" or "therapeutically effective amount" means a dosage sufficient to treat, inhibit, or alleviate one or more symptoms of the disorder being treated or to otherwise provide a desired pharmacologic and/or physiologic effect. The precise dosage will vary according to a variety of factors such as subject-dependent variables (e.g., age, immune system health, etc.), the disease, and the treatment being effected.

In some embodiments, the disclosed compositions exhibit the same or similar ligand binding in vivo as in vitro, have less of a reduction in ligand binding compared to traditionally targeted particles (e.g., direct antibody conjugation), and/or improves one or more other translational issues such as those described in Tietjen, et al., *Trends in Molecular Medicine*, 24(7):598-606 (2018), which is specifically incorporated by reference herein in its entirety.

The compositions can be administered by, for example, intravenous, or subcutaneous, or intramuscular injection or infusion or other routes discussed herein or known in the art. See, e.g., Cheng, et al., *Nature Reviews Drug Discovery* 14, 239-247 (2015), which is specifically incorporated by reference in its entirety.

The administration can be local or system. In some embodiments, the compositions are delivered in specific anatomic locations to enhance the first-pass rapid accumulation in the organ of interest. Endotheilal cells in various organs, such as the heart and the brain, have also been successfully targeted by anti-CD31-therapeutic when administered in this way (Tietjen et al., *Sci. Transl. Med.* 9, eaam6764 (2017), Scherpereel, *J. Pharmacol. Exp. Ther.* 300, 777-786 (2002), Danielyan, et al., *J. Pharmacol. Exp. Ther.* 321, 947-952 (2007).

1. Drug Delivery

The particles can be used to deliver an effective amount of one or more therapeutic, diagnostic, and/or prophylactic agents to an individual in need of such treatment. The amount of agent to be administered can be readily determine by the prescribing physician and is dependent on the age and weight of the patient and the disease or disorder to be treated.

The particles are useful in drug delivery (as used herein "drug" includes therapeutic, nutritional, diagnostic and prophylactic agents), and nucleic acid conjugates and themselves be active, whether injected intravenously, subcutaneously, or intramuscularly, administered to the nasal or pulmonary system, injected into a tumor milieu, administered to a mucosal surface (vaginal, rectal, buccal, sublingual), or encapsulated for oral delivery. The particles and nucleic acids and other deliverables may be administered as a dry powder, as an aqueous suspension (in water, saline, buffered saline, etc), in a hydrogel, organogel, in capsules, tablets, troches, or other standard pharmaceutical excipient The preferred embodiment is a dry powder rehydrated with the capsulant of interest in sterile saline or other pharmaceutically acceptable excipient.

As discussed herein, compositions can be used as delivery vehicles for a number of active agents including small molecules, nucleic acids, proteins, and other bioactive agents. The active agent or agents can be encapsulated within, dispersed within, and/or associated with the surface of the particles. In some embodiments, the particles package two, three, four, or more different active agents for simultaneous delivery to a cell.

The compositions and methods can be used across a range of application and to treat a host of diseases and disorder, as well as improve transplantation outcomes.

For example, in some embodiments the compositions are administered to a subject with cancer. The cargo can be, for example a chemotherapeutic agent, or a vascular normalization agent (see, e.g., Huang, et al., Cancer Res; 73(10); 2943-8 (2013)). In an exemplary embodiment, the cancer is hepatocyte carcinoma, the cargo is a normalization agent or chemotherapeutic agent, and the composition is administered in an anatomic location to enhance the first-pass rapid accumulation of the composition in the cancer.

2. Transfection

The disclosed compositions can be for cell transfection of polynucleotides. The transfection can occur in vitro or in vivo, and can be applied in applications including gene therapy and disease treatment. The compositions can be more efficient, less toxic, or a combination thereof when compared to a control. The polynucleotides can be composed RNA, DNA, synthetic or modified nucleic acids, or a combination thereof.

The particular polynucleotide delivered with or without particles can be selected by one of skill in the art depending on the condition or disease to be treated. The polynucleotide can be, for example, a gene or cDNA of interest, a functional nucleic acid such as an inhibitory RNA, a tRNA, an rRNA, or an expression vector encoding a gene or cDNA of interest, a functional nucleic acid a tRNA, or an rRNA. In another embodiment, siRNA, antisense polynucleotides (including siRNA or antisense polynucleotides) or inhibitory RNA can be transfected into a cell using the compositions described herein. In some embodiments two or more polynucleotides are administered in combination.

In some embodiments, the polynucleotide encodes a protein.

In some embodiments, the polynucleotide is not integrated into the host cell's genome (i.e., remains extrachromosomal). Such embodiments can be useful for transient or regulated expression of the polynucleotide, and reduce the risk of insertional mutagenesis. In some embodiments, the particles are used to deliver mRNA or non-integrating expression vectors that are expressed transiently in the host cell.

In some embodiments, the polynucleotide is integrated into the host cell's genome. For example, gene therapy is a technique for correcting defective genes responsible for disease development. Researchers may use one of several approaches for correcting faulty genes: (a) a normal gene can be inserted into a nonspecific location within the genome to replace a nonfunctional gene. This approach is most common; (b) an abnormal gene can be swapped for a normal gene through homologous recombination; (c) an abnormal gene can be repaired through selective reverse mutation, which returns the gene to its normal function; (d) the regulation (the degree to which a gene is turned on or off) of a particular gene can be altered.

B. In Vitro and Ex Vivo Methods

The disclosed compositions can be used in a method of delivering active agents to cells in vitro and ex vivo. For example, the particles and nucleic acids and other deliverables can be used for in vitro or ex vivo drug delivery to, or transfection of, cells. The method typically involves contacting the cells with particles including an active agent or nucleic acids in an effective amount to introduce the active agent or nucleic acid into the cell's cytoplasm. In some embodiments, the polynucleotide or drug is delivered to the cells in an effective amount to change the genotype or a phenotype of the cell. The cells can be primary cells isolated from a subject, or cells of an established cell line. The cells can be of a homogenous cell type, or can be a heterogeneous mixture of different cells types. The cells can be part of a tissue or organ.

For example, in some embodiments, the disclosed compositions are used to transfect T cells with constructs to prepare CAR-T cells. See, e.g., National Cancer Institute website: "CAR T Cells: Engineering Patients' Immune Cells to Treat Their Cancers", Agarwal, et al., *Oncoimmunology*, 2019 Oct. 10; 8(12):e1671761. doi: 10.1080/ 2162402X.2019.1671761. This could be done outside the body and re-infused (i.e., ex vivo) or in vivo with direct targeting of T cells.

As a non-limiting example, in a static culture (such as in Petri dishes), administration of particles containing synthetic binding protein-targeting agent conjugate or administration of a targeting agent (such as an antibody) followed by administration of particles containing a synthetic binding protein (such as a monobody) showed about 300 and 200 times, respectively, more binding to cells compared to a corresponding particle containing an antibody targeting agent but lacking a synthetic binding protein.

In another non-limiting example, such as culture in flow, targeting agent-synthetic binding protein-particle system showed 20 times enhanced binding than a corresponding targeting agent-particle system. Further, in another culture in flow setting, under microfluidic flow, a targeting agent-synthetic binding protein-particle system showed dramatically improved binding in ex vivo perfusion of mammalian (human) vessels, compared to a corresponding targeting agent-particle system.

Because of the relatively enhanced targeting features possessed by the particles and nucleic acids and other deliverables described herein, this platform technology can be leveraged in static culture in Petri dish settings, culture in flow in ex vivo organ perfusion settings, such as in organ, tissue, and cell transplant technologies, or more generally in in vivo delivery of therapeutic, diagnostic, and/or prophylactic agents.

Any eukaryotic cell or cells can be the target cell or cells. Suitable types of cells include, but are not limited to, undifferentiated or partially differentiated cells including stem cells, totipotent cells, pluripotent cells, embryonic stem cells, inner mass cells, adult stem cells, bone marrow cells, cells from umbilical cord blood, and cells derived from ectoderm, mesoderm, or endoderm. Suitable differentiated cells include somatic cells, neuronal cells, skeletal muscle, smooth muscle, pancreatic cells, liver cells, and cardiac cells. Target cells also include, e.g., endothelial cells, epithelial cells, T cells, B cells, NK cells, NKT cells, Neutrophils, red blood cells (i.e., any circulating cell type).

In vitro or ex vivo treated cells, tissue, organs, etc. can be administered to subject in need thereof in a therapeutically effective amount. For example, target cells can be first isolated from a donor using methods known in the art, contacted with the particles including a drug or polynucleotide, or nucleic acid conjugate. The treated cells can then be administered to a patient in need thereof. Sources or cells include cells harvested directly from the patient or an allographic donor. In preferred embodiments, the target cells to be administered to a subject will be autologous, e.g. derived from the subject, or syngenic. Allogeneic cells can also be isolated from antigenically matched, genetically unrelated donors (identified through a national registry), or by using target cells obtained or derived from a genetically related sibling or parent.

In some embodiments, both ex vivo and in vivo, the composition are used for immunomodulation. In more specific embodiments, the compositions are used for immunosuppression. Exemplary active agents include, but are not limited to, Rapamycin or other immunomodulators and immunosupressants, and/or inhibitors of NfKB pathway (e.g. Bay11), MCC950 (NLRP3 inhibitor) or other cellular signaling pathways relevant in disease. In some embodiments, the compositions and methods are used to inhibit MHCI and or II. See, e.g., Cui, et al., *Nature Communications* volume 8, Article number: 191 (2017). The nucleic acid can be CIITA.

The disclosed compositions and methods can be further understood through the following numbered paragraphs.

1. A particle or nucleic acid comprising one or more synthetic binding proteins, wherein one or more of the synthetic binding proteins comprises:
   (i) a first surface comprising a targeting agent binding site, and
   (ii) a second surface comprising a chemical moiety through which the synthetic binding protein is conjugated to the particle's surface,
   optionally wherein the conjugation does not interfere with the function of the targeting agent binding site, and optionally, wherein the first and second surfaces are separated by a portion of the synthetic binding protein.
2. The particle or nucleic acid of paragraph 1, wherein the targeting agent binding site is capable of binding to an Fc domain of an antibody.
3. The particle or nucleic acid of paragraph 1, further comprising a targeting agent conjugated to the targeting agent binding site.
4. The particle or nucleic acid of paragraph 3, wherein the targeting agent is selected from peptides, nucleic acids, glycoproteins, carbohydrates, lipids, or a combination thereof.
5. The particle or nucleic acid of paragraph 3 or 4, wherein the targeting agent is an antibody, wherein the antibody is conjugated to the targeting agent binding site via an Fc domain of the antibody.
6. The particle or nucleic acid of any one of paragraphs 1 to 5, wherein one or more of the synthetic binding proteins has a molecular weight between 5 kDa and 50 kDa inclusive, 5 kDa and 17.5 kDa, inclusive, between 7.5 kDa and 21 kDa, inclusive, between 7.5 kDa and 17.5 kDa, inclusive, or between 10 kDa and 15 kDa, inclusive.
7. The particle or nucleic acid of any one of paragraphs 1 to 6, wherein one or more of the synthetic binding proteins is based on a fibronectin type III domain.
8. The particle or nucleic acid of any one of paragraphs 1 to 7, wherein one or more of the synthetic binding proteins comprises an immunoglobulin fold and no disulfide bonds.
9. The particle or nucleic acid of any one of paragraphs 1 to 8, wherein one or more of the synthetic binding proteins is a polypeptide monobody.
10. The particle or nucleic acid of any one of paragraphs 1 to 9, wherein conjugation of the synthetic binding protein to the particle's surface comprises a covalent linkage, wherein the covalent linkage comprises the structure:

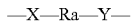   Formula I wherein,
    X and Y, independently, contain between 3 and 90 atoms, inclusive, between 3 and 85 atoms, inclusive, between 3 and 80 atoms, inclusive, between 3 and 70 atoms, inclusive, between 3 and 60 atoms, inclusive, between 3 and 50 atoms, inclusive, between 3 and 40 atoms, inclusive, between 3 and 30 atoms, inclusive, or between 3 and 20 atoms, inclusive, preferably X contains between 3 and 20 atoms, inclusive, and Y contains between 3 and 10 atoms, and
    Ra comprises a 3-thiopyrrolidine-2,5-dione moiety, 3-aminopyrrolidine-2,5-dione moiety, 3-thiomaleimide moiety, 3-aminomaleimide moiety, a triazole moiety, a carbamate, oxime ether, hydrazone, a carbonyl, imine, sulfonamide, azo, dialkyl dialkoxysilane, diaryl dialkoxysilane, orthoester, acetal, aconityl, (3-thiopropionate, phosphoramidate, trityl, vinyl ether, polyketal, or a combination thereof.
11. The particle or nucleic acid of paragraph 10, wherein X and Y, are independently substituted alkyls; substituted alkylenes; unsubstituted alkylenes; polyether, such as poly(ethylene glycol); substituted alkenyls; substituted alkynyls; substituted aryls; substituted heteroaryl; substituted C3-C20 cycloalkyls, substituted $C3-C_{20}$ heterocycyls, or a combination thereof.
12. The particle or nucleic acid of paragraph 10 or 11, wherein X and Y independently contain a substituted alkyl, substituted alkylene, unsubstituted alkylene, or substituted aryl.
13. The particle or nucleic acid of any one of paragraphs 10 to 12, wherein Ra comprises a 3-thiopyrrolidine-2,5-dione moiety.
14. The particle or nucleic acid of any one of paragraphs 1 to 13, wherein the chemical moiety is an amino acid selected from the group consisting of cysteines, lysines, ornithines, arginines, serines, threonines, tyrosines, and combinations thereof.
15. The particle or nucleic acid of any one of paragraphs 1 to 14, wherein the chemical moiety is a cysteine.
16. The particle or nucleic acid of any one of paragraphs 1 to 15, wherein the particle is a polymeric particle, liposome, or inorganic particle.
17. The particle or nucleic acid of paragraph 16, wherein the particle is a polymeric particle comprising one or more amphiphilic polymers comprising a hydrophobic polymer portion and a hydrophilic polymer portion; one or more hydrophobic polymers; one or more hydrophilic polymers; co-polymers; or blends thereof.
18. The particle or nucleic acid of paragraph 16 or 17, wherein the particle comprises one or more amphiphilic polymers comprising a hydrophobic polymer portion and a hydrophilic polymer portion.
19. The particle or nucleic acid of paragraph 17 or 18, wherein the hydrophobic polymer portion or hydrophobic polymer comprises polyesters; poly(anhydride)s; poly(orthoester)s; hydrophobic polypeptides; polyamides; poly(ester-amide)s; poly(beta-amino ester)s; poly(amine-co-ester)s; poly(amine-co-ester-co-ortho ester)s; poly(alkyl acrylate)s (such as poly (methyl acrylate)); poly(alkyl alkacrylate)s (such as poly (methyl methacrylate)); poly(alkyl acrylamide)s (such as poly (N-isopropyl acrylamide)); poly(alkyl alkacrylamide)s (such as poly (N-isopropyl methacrylamide)); alkyl celluloses; cellulose esters; polyurethanes; polyureas; poly(urea ester)s; poly(amide-enamine)s; hydrophobic polyethers (such as polypropylene glycol); or copolymers thereof.
20. The particle or nucleic acid any one of paragraphs 17 to 19, wherein the hydrophobic polymer portion or hydrophobic polymer comprises polyesters, preferably hydrophobic poly(hydroxy acid)s.
21. The particle or nucleic acid of paragraph 20, wherein the polyesters are selected from the group consisting of poly(lactic acid)s, poly(lactic acid-co-glycolic acid)s, poly(glycolic acid)s, and combinations thereof.
22. The particle or nucleic acid of any one of paragraphs 16 to 21, wherein the particle comprises poly(lactic acid)s.

23. The particle or nucleic acid of any of paragraphs 16 to 22, wherein the particle comprises one or more hydrophilic polymers.
24. The particle or nucleic acid of paragraph 23, wherein one or more of the hydrophilic polymers is a polyalkylene glycol.
25. The particle or nucleic acid of any one of paragraphs 16 to 24, wherein the particle comprises polyethylene glycols.
26. The particle or nucleic acid of any one of paragraphs 16 to 25, wherein the particle is a polymeric particle comprising poly(lactic acid)-block-poly(ethylene glycol)s, poly(glycolic acid)-block-poly(ethylene glycol)s, poly(lactide-co-glycolic)-block-poly(ethylene glycol), or a combination thereof.
27. The nanoparticle or nucleic acid of any one of paragraphs 1 to 26, wherein the particle is a nanoparticle or a microparticle.
28. The particle or nucleic acid of any one of paragraphs 1 to 27, wherein the particle comprise therapeutic agents, diagnostic agents, prophylactic agents, or a combination thereof.
29. A pharmaceutical composition comprising the particle or nucleic acid of any one of paragraphs 1 to 28 and a pharmaceutically acceptable carrier.
30. A method of treating a subject in need thereof comprising
(i) administering to the subject, or
(ii) administering to an organ, tissue, or cell to be transplanted to the subject,
an effective amount of the particles or nucleic acid of any one of paragraphs 1 to 28 or the pharmaceutical composition of paragraph 29.
31. The method of paragraph 30, wherein the targeting agent is administered prior to administering the particles or the pharmaceutical composition.
32. The method of paragraph 30, wherein the targeting agent is co-administered with the particles or nucleic acid or the pharmaceutical composition.
33. The method of any one of paragraphs 30 to 32, wherein administration to the organ occurs ex vivo.
34. A method of making the particle or nucleic acid of any one of paragraphs 1 to 28, the method comprising:
(i) reacting the chemical moiety on the second surface with a reactive group on the surface of the particle or nucleic acid.
35. The method of paragraph 34, wherein the chemical moiety or the reactive group comprises a thiol; alkyne; azide; maleimide; alkene; triarylphosphine; aminooxy; carbonyl; hydrazide; sulfonyl chloride; maleimide; aziridine; —CN; acryloyl; acrylamide; sulfone; vinyl sulfone; cyanate; thiocyanate; isocyanate; isothiocyanate; alkoxysilane; dialkyl dialkoxysilane; diaryl dialkoxysilane; trialkyl monoalkoxysilane; vinyl silane; acetohydrazide; acyl azide; acyl halides; epoxide; glycidyl; carbodiimides; amine; hydroxyl; phosphoramidate; vinyl ether; substituted hydrazine; an alkylene glycol bis(diester), such as ethylene glycol bis(succinate); thioester, such as alkyl thioester, α-thiophenylester, allyl thioester (such as allyl thioacetae, allyl thioproprionate); allyl ester (such as allyl acetate, allyl propionate); aryl acetate (such as phenacyl ester); orthoester; sulfonamide, such as 2-N-acyl nitrobenzenesulfonamide; vinyl sulfide; or a combination thereof.
36. The method of paragraph 34 or 35, wherein the chemical moiety comprises a thiol.
37. The method of any one of paragraphs 34 to 36, wherein the reactive group comprises a maleimide.
38. The method of any one of paragraphs 34 to 37, further comprising conjugating a targeting agent to the first surface comprising the targeting agent binding site prior to or after step (i).
39. The method of paragraph 38, wherein conjugating the targeting agent occurs via non-covalent conjugation.
40. The method of paragraph 38 or 39, wherein the targeting agent is selected from peptides, nucleic acids, glycoproteins, carbohydrates, lipids, or a combination thereof.
41. The method of any one of paragraphs 38 to 40, wherein the targeting agent is an antibody, wherein the antibody is conjugated to the targeting agent binding site via an Fc domain of the antibody.
42. Any of the foregoing paragraphs wherein the nucleic acid is (i) single stranded or double stranded, (ii) comprises RNA, DNA, modified nucleic acids, or a combination thereof.
43. Any of the foregoing paragraphs wherein the nucleic acid is selected from mRNA, DNA encoding polypeptides of interest for example an expression construct or vector, inhibitory nucleic acids such as antisense molecules, siRNA, miRNA, aptamers, ribozymes, RNAi, and external guide sequences, and nucleic acids encoding the inhibitory nucleic acid including, for example expression constructs and vectors.
44. A polypeptide comprising the amino acid sequence

```
                                         (SEQ ID NO: 2)
MKHHHHHHSSDYKDDDDKGENLYFQGSVSSVPTKLEVVAATPTSLLISW
DAPAVTVYYYVITYGETGGNSPVQEFTVPGSKSTATISGLKPGVDYTIT
VYAGYGSGGYYSPISINYRTEIDKC;

(SEQ ID NO: 3)
MKHHHHHHSSDYKDDDDKGENLYFQGSVSSVPTKLEVVAATPTSLLISW
DAYPVYVSYYRITYGETGGNSPVQEFTVPGSSSTATISGLSPGVDYTIT
VYAYYKYGHYWSPISINYRTEIDKC;

(SEQ ID NO: 4)
MKHHHHHHSSDYKDDDDKGENLYFQGSVSSVPTKLEVVAATPTSLLISW
DASGISVSYYRITYGETGGNSPVQEFTVPGSSSTATISGLKPGVDYTIT
VYAYYKYGQYYSPISINYRTEIDKC;
``` or a variant or functional fragment of SEQ ID NO:2, 3, or 4 with at least 75%, 80%, 85%, 90%, 95%, or more sequence identity to SEQ ID NO:2, 3, or 4.

45. A polypeptide comprising the amino acid sequence

```
                                         (SEQ ID NO: 2)
MKHHHHHHSSDYKDDDDKGENLYFQGSVSSVPTKLEVVAATPTSLLISW
DAPAVTVYYYVITYGETGGNSPVQEFTVPGSKSTATISGLKPGVDYTIT
VYAGYGSGGYYSPISINYRTEIDKC;

(SEQ ID NO: 3)
MKHHHHHHSSDYKDDDDKGENLYFQGSVSSVPTKLEVVAATPTSLLISW
DAYPVYVSYYRITYGETGGNSPVQEFTVPGSSSTATISGLSPGVDYTIT
VYAYYKYGHYWSPISINYRTEIDKC;

(SEQ ID NO: 4)
MKHHHHHHSSDYKDDDDKGENLYFQGSVSSVPTKLEVVAATPTSLLISW
DASGISVSYYRITYGETGGNSPVQEFTVPGSSSTATISGLKPGVDYTIT
VYAYYKYGQYYSPISINYRTEIDKC;
``` with or without the N-terminal tag, the C-terminal tag, or both, or a variant or functional fragment thereof with at least 75%, 80%, 85%, 90%, 95%, or more sequence identity thereto, wherein the polypeptide comprises a cysteine.

46. The polypeptide of paragraphs 44 and 45, wherein the polypeptide binds to murine IgG1 Fc.

Those skilled in the art will recognize, or be able to ascertain using no more than routine experimentation, many equivalents to the specific embodiments of the invention described herein. Such equivalents are intended to be encompassed by the following claims.

EXAMPLES

Example 1: Synthesis and Development of Monobody Conjugated Nanoparticles

Materials and Methods

Monobody Development

Mouse IgG1 Fc protein with C-terminal Avi-tag and His$_6$ tag was produced using EXPI293 and EXPICHO cells (ThermoFisher) and purified using Ni-affinity chromatography.

The mouse Fc protein was enzymatically biotinylated using purified BirA enzyme. This protein was used to screen monobody phage-display libraries, as described previously (Koide, et al., *J Mol Biol* 415, 393-405 (2012); Sha, et al., *Proc Natl Acad Sci USA* 110, 14924-14929 (2013)). After four rounds of phage selection, the sorted pools were subcloned into a yeast display library following recombination of 5' and 3' fragments to increase library diversity as described previously (Koide, et al., *J Mol Biol* 415, 393-405 (2012) before two further rounds of screening using yeast display. Isolated clones were validated for target binding using yeast display, as described previously (Koide, et al., *J Mol Biol* 415, 393-405 (2012), Sha, et al., *Proc Natl Acad Sci USA* 110, 14924-14929 (2013)). The isolated Monobody clones with an N-terminal tag containing His$_6$, FLAG epitope and a TEV cleavage site and a C-terminal tag containing a Cys residue (see underlining in the sequences) were expressed in *Escherichia coli* and purified, as described previously (Koide et al., 2012; Sha et al., 2013).

Monobody Sequences

The amino acid sequences of Fc-binding monobodies are as follows. The N- and C-terminal tags are underlined.

pHFT1-Mb(FC-S5)-EIDKC
(SEQ ID NO: 2)
<u>MKHHHHHHSSDYKDDDDKGENLYFQG</u>SVSSVPTKLEVVAATPTSLLISW
DAPAVTVYYYVITYGETGGNSPVQEFTVPGSKSTATISGLKPGVDYTIT
VYAGYGSGGYYSPISINYRT<u>EIDKC</u> pHFT1-Mb(FC-LN2)-EIDKC
(SEQ ID NO: 3)
<u>MKHHHHHHSSDYKDDDDKGENLYFQG</u>SVSSVPTKLEVVAATPTSLLISW
DAYPVYVSYYRITYGETGGNSPVQEFTVPGSSSTATISGLSPGVDYTIT
VYAYYKYGHYWSPISINYRT<u>EIDKC</u> pHFT1-Mb(FC-L9)-EIDKC
(SEQ ID NO: 4)
<u>MKHHHHHHSSDYKDDDDKGENLYFQG</u>SVSSVPTKLEVVAATPTSLLISW
DASGISVSYYRITYGETGGNSPVQEFTVPGSSSTATISGLKPGVDYTIT
VYAYYKYGQYYSPISINYRT<u>EIDKC</u>

Surface Plasmon Resonance (SPR) Measurements.

Monobodies were produced with an an N-terminal tag containing His$_6$, FLAG epitope and a TEV cleavage site, biotinylated in *E. coli* BL21(DE3) straining harboring the BirA enzyme and purified, as described previously (Sha, et al., *Proc Natl Acad Sci USA* 110, 14924-14929 (2013)). SPR measurements were performed at 25° C. in sodium phosphate buffer (50 mM) containing NaCl (150 mM) and Tween20 (0.005%) on a Pioneer SPR instrument (ForteBio). Biotinylated Monobodies were immobilized on the sensor surface via streptavidin and antibody samples were flowed using a OneStep gradient injection protocol.

Nanoparticle Synthesis

The organic solvent was removed using a 50 mL amicon filter tube (Amicon® Ultra-15 Centrifugal Filter Unit, MCWO 10000, Sigma Aldrich) for small batches (two spins) or using a tangential flow filtration system (Spectrum® KrosFlo® KR2i TFF System, Repligen) equipped with a Microkros column (Microkros 20 cm 500K MPES 0.5 mm MLL X FLL, C02-E500-05-N, Repligen) for big batches (more than 50 mg)

Maleimide functionalized poly(lactic acid)-poly(ethylene) glycol NPs (Dil-PLA-PEG-mal) were prepared by a nanoprecipitation protocol as follows. A blend of PLA-PEG-methoxy (PLA-PEG-m) and PLA-PEG-malemide (PolySciTech No. AI60) was each dissolved to a concentration of 100 mg/ml in DMSO and then blended at the desired polymer weight ratio. The desired weight ration of Dil dye in DMSO was then added to the blended polymer solution. The polymer solution in DMSO was added dropwise to stirring (1100 RPM) sterile deionized H$_2$O (diH$_2$O). The NPs formed upon mixing. The organic solvent was removed using a 50 mL amicon filter tube (Amicon® Ultra-15 Centrifugal Filter Unit, MCWO 10000, Sigma Aldrich) for small batches (two spins) or using a tangential flow filtration system (Spectrum® KrosFlo® KR2i TFF System, Repligen) equipped with a Microkros column (Microkros 20 cm 500K MPES 0.5 mm MLL X FLL, C02-E500-05-N, Repligen) for big batches (more than 50 mg). NPs were aliquoted and snap-frozen in liquid N$_2$. Size (nm) and surface charge (Zeta-potential) were determined at 160 nm (PDI of ~0.15) and −5 mV respectively.

PACE-PVA-VS were prepared following an emulsion-evaporation method (Kauffman et al—*Biomacromolecules* 2018, 19, 9, 3861-3873). The polymer was dissolved in DCM at 50 mg/mL and mixed with lipophilic fluorescent dye (DiD) at a dye:polymer weight ratio of 0.5%. This organic phase was then added dropwise with a glass pasteur pipette into a PVA-VS solution at 5% (w/w) under vigorous vortexing (organic:aqueous phase volume ratio of 1:2). The resulting emulsion was then transferred into a beaker containing 3 times it volume of PVA solution at 0.3% (w/w) under agitation. After 1 min the organic solvent was evaporated using a rotary evaporator. The excess of PVA and PVA-VS was washed by two centrifugations (18 000 g, 45 min, 4° C.). The pellet was redispersed in DI water, flash frozen in liquid nitrogen and stored at −80° C.

Monobody Conjugation to Maleimide Functionalized Nanoparticles

Monobody conjugation of the maleimide functionalized (Dil-PLA-PEG-mal, PACE-PVA-Vs, and Gold) nanoparticles was performed as follows. To an eppendorf tube containing Dil-PLA-PEG-mal nanoparticles at 5 mg/mL was added MES buffer (1M, pH 5.5) and varying amounts of the Monobody solution (2 mg/mL, pH 7.5). The mixture was incubated at room temperature on an orbital shaker at 250 RPM for varying amounts of time, then centrifuged for 15 minutes at 25,000 g at 17° C. The supernatant was removed and the NPs were resuspended in Phosphate-buffered saline (PBS).

To prepare Mb-conjugated nanoparticles on a larger scale, Dil-PLA-PEG-mal nanoparticles at 5 mg/mL (50% maleimide), MES buffer (1M, pH 5.5) and Monobody (2 mg/mL, pH 7.5) were mixed in a 50 mL conical tube. The mixture was incubated at room temperature on an orbital shaker at 250 RPM for 1 hour, then centrifuged for 15 minutes at 25,000 g at 17° C. The supernatants was removed and the NPs were resuspended in 1×PBS.

PLA-PEG-COOH NPs were conjugated to targeting antibodies (IgG1 mouse anti-hum-CD31 Ab or IgG1 mouse Isotype Ab) as previously described (Tietjen et al—Science Translational Medicine 2017, 9, 418) using 1-ethyl-3-(3-dimethylaminopropyl) carbodiimide hydrochloride (EDC) and N-hydroxysuccinimide (NHS) chemistry resulting in PLA-PEG-Ab-NP (PLA-PEG-CD31-NP and PLA-PEG-Iso-NP).

Cell Culture and NP Binding Efficiency Assay

Human Umbilical Vein Endothelial Cells (HUVEC) were plated on a gelatin-treated 96 well plate at $2.10^4$ cells/well. Upon confluence, the cells were first treated with anti-CD31 antibody (Biolegend, part #94218) or IgG1 isotype control antibody (BD Pharmingen, part #624084) at 33 nM for 1 h then washed and treated with Mb-NPs at 50 ug/mL for 2 h. After treatment the unbound NPs were extensively washed with culture media, then the cells were lifted and their fluorescence was measured by flow cytometry (Stratedigm STD-13/Cytoflex/LSRII).

Flow Cytometry

DiI (42364 Sigma-Aldrich)-loaded particles were detected by flow cytometry.

Results

Studies to characterize the maleimide functionalized NPs (before Mb conjugation) indicated a size of approximately 170 nm, PdI of approximately 0.15 and zeta potential of approximately −5 mV.

Experiments were performed to determine the synthesis conditions that allow optimal targeting of Mb-conjugated nanoparticles. To determine the ability of Mb-conjugated nanoparticles to specifically bind targets on a cell surface in static culture, HUVECs were incubated either with IgG1 isotype control or anti-CD31 antibody. Anti-CD31 Abs conjugated either to NPs or directly to therapeutic molecules have been previously used to target endothelial cells in vivo in animal models, including in the context of organ transplantation. The Mb is designed to recognize the Fc region of the antibody.

Figure 1B:
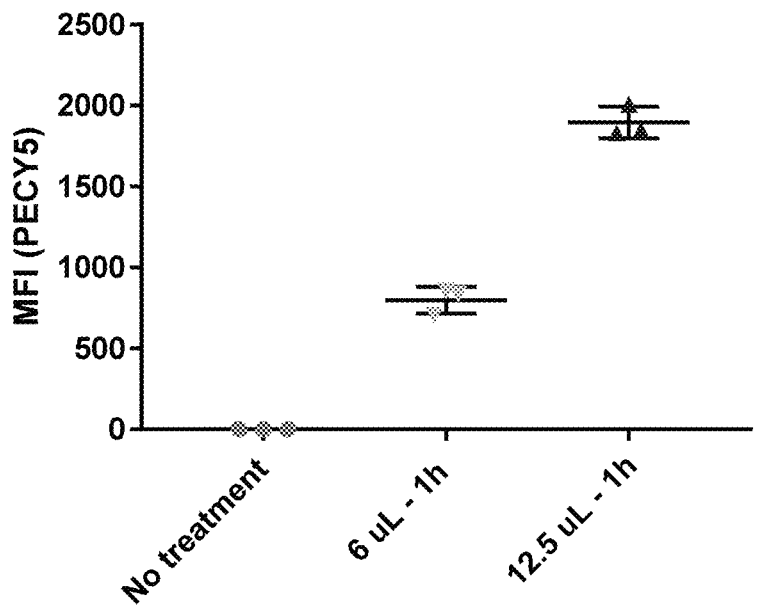
FIG. 1B is a graph showing quantification of the MFI by flow cytometry when HUVECs were exposed to Monobody (Mb) conjugated nanoparticles prepared with varying amounts of Mb relative to nanoparticle during the conjugation reaction.
Figure 1C:
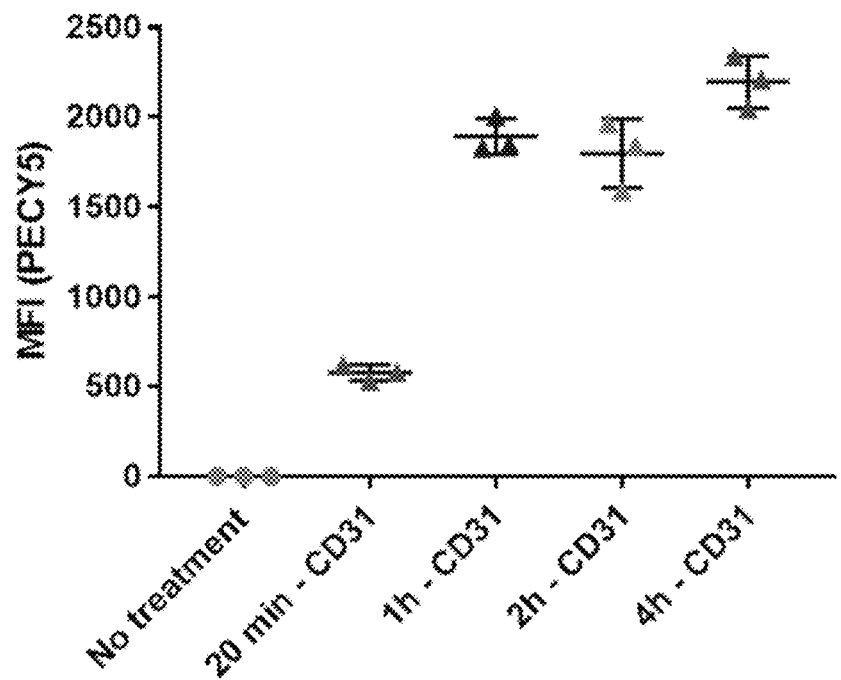
FIG. 1C is a graph showing quantification of the MFI when HUVECs were exposed to Monobody (Mb) conjugated nanoparticles prepared by reacting Mb with maleimide functionalized NPs for varying amounts of time.
Figure 1D:
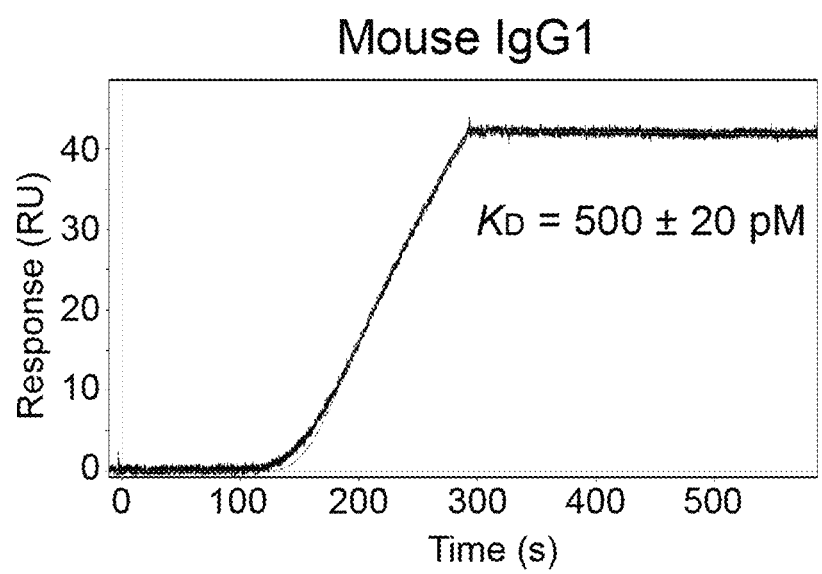
FIG. 1D is a surface plasmon resonance (SPR) sensorgram of mouse IgG1 binding to immobilized Monobody. The measurement was performed at 25° C. on a Pioneer SPR instrument (ForteBio) using a OneStep gradient injection protocol.

As shown in FIG. 1A, the Mb-conjugated NPs showed the highest degree 10 of binding to anti-CD31 Ab-bound HUVECs when prepared with 50% maleimide (w %) (e.g., 50% by weight for each of PLA-PEG-m and PLA-PEG-Mal). In contrast, cells pre-treated with IgG1 isotype control showed no binding to Mb-conjugated NPs. Results also indicated that using 12.5 uL of Monobody for the conjugation reaction yielded more efficient cell targeting compared to 6 uL (FIG. 1B). Comparison of reaction times indicated that incubation of the conjugation reaction on the orbital shaker for 1 hour was optimal, with longer incubation times not showing any significant improvement in cell targeting (FIG. 1C).

Example 2: Antibody-Nanoparticle Conjugation

Materials and Methods

Nanoparticle Synthesis

Conventional poly(lactic acid)-poly(ethylene) glycol (PLA-PEG) nanoparticles (NPs) were prepared as follows. The (DiI-PLA-PEG-COOH) nanoparticles were synthesized by a nanoprecipitation protocol as previously described (Tietjen G T., et al., Sci Transl Med., 9(418), eaam6764 (2017)). Briefly, PLA-PEG copolymer was dissolved at a concentration of 100 mg/ml in DMSO and then diluted to the desired concentration for NP formulation. The polymer solution in DMSO was added dropwise to vigorously stirring sterile deionized $H_2O$ (di$H_2O$). NPs were subsequently filtered through a 1.2-μm cellulose acetate membrane (GE Healthcare Life Sciences) filter to remove any polymer aggregates and then pooled. The NP solutions were then transferred in batches to dialysis cassettes (12-ml volume; molecular weight cutoff, 10,000; Slide-A-Lyzer, Thermo Fisher Scientific) and dialyzed against two exchanges of about 2.2 liters of di$H_2O$ at room temperature to remove excess DMSO. After dialysis, NPs were aliquoted and snap-frozen in liquid $N_2$.

Antibody Conjugation to Mb Functionalized NPs

The DiI-PLA-PEG-COOH and Monobody functionalized (DiI-PLA-PEG-mal-Mb) nanoparticles were synthesized as described in Example 1.

To conjugate antibody to Monobody functionalized NPs (i.e., DiI-PLA-PEG-mal-Mb nanoparticles), varying concentrations of anti-CD31 or IgG1 isotype control antibody (1, 2 and 5 mg/mL) was mixed with DiI-PLA-PEG-mal NPs at 5 mg/mL. The mixture was incubated at room temperature on an orbital shaker at 250 RPM for varying amounts of time, then centrifuged for 15 minutes at 25,000 g at 17° C. The supernatant was removed and the NPs were resuspended in PBS.

To prepare Ab-conjugated Mb-nanoparticles on a larger scale, DiI-PLA-PEG-mal-Mb nanoparticles at 5 mg/mL and antibody at 1 mg/mL were mixed in a 50 mL conical tube. The mixture was incubated at room temperature on an orbital shaker at 250 RPM for 1 hour, then centrifuged for 15 minutes at 25,000 g at 17° C. The supernatant was removed and the NPs were resuspended in 1×PBS.

Antibody Conjugation to Conventional NPs

Ab-conjugated PLA-PEG NPs were generated via EDC (1-ethyl-3-(3-dimethylaminopropyl)carbodiimide)-NHS (N-hydroxysulfoxuccinimide) mediated coupling as previously described (Tietjen G T., et al., Sci Transl Med., 9(418), eaam6764 (2017)).

Briefly, commercial Abs were purchased from BD Biosciences (CD31, clone WM59; Isotype, clone MOPC-21, sodium azide free). For a single batch, 1 mL of NPs at 10 mg/mL was thawed and briefly sonicated to fully resuspend the NPs. 57 uL of 1M MES pH 5.5, 57 uL was added to the NPs followed by 57 uL each of EDC and NHS both at 100 mg/mL. The mixture was then vigorously vortexed for 15 minutes, then split into 2 equal volumes (~570 uL each). The NPs were centrifuged for 15 minutes at 25,000 g at 17° C. followed by aspiration to remove the supernatant. The NP pellets were resuspended in 20 μL of MES in DPBS and pooled into 1 tube. 250 μL antibody at 2 mg/mL and 5 μL of 1M MES pH 5.5 were added to the NP suspension.

The NP/antibody solution was then vigorously vortexed for 1 hr. Following the antibody coupling, the reaction was quenched by addition of 3 μL of 1M Tris pH 8. The mixture was transferred to a clean tube then centrifuged for 15 minutes at 25,000 g at 17° C. and the supernatant aspirated. The final antibody-NP conjugate was resuspended in 100 uL of PBS (1X).

Cell Culture and NP Binding Efficiency Assay

Human Umbilical Vein Endothelial Cells (HUVEC) were plated on a gelatin-treated 96 well plate at $2.10^4$ cells/well. Upon confluence, the cells were treated with Ab-Mb-NPs at 50 ug/mL for 2 h. After treatment the unbound NPs were extensively washed with culture media, then the cells were lifted and their fluorescence was measured by flow cytometry (Stratedigm STD-13/Cytoflex/LSRII).

Results

Figure 2A:
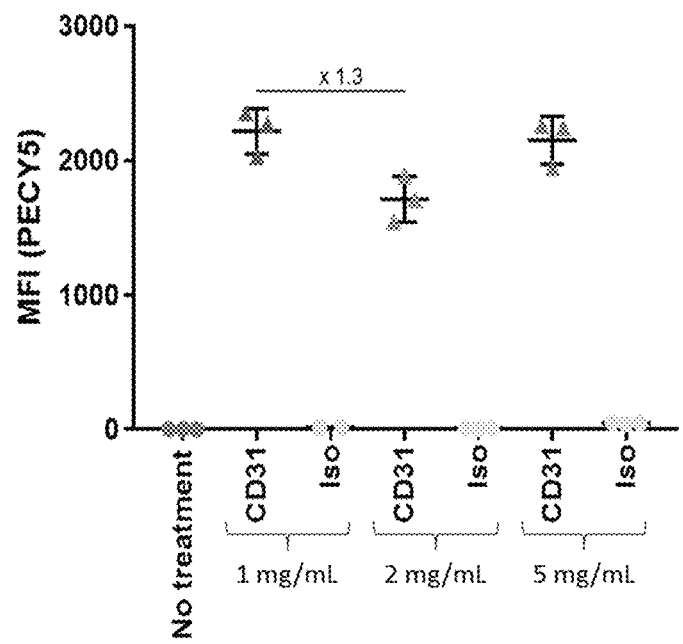
FIG. 2A is a graph showing quantification of the Mean Fluorescence Intensity (MFI) as measured by flow cytometry, when HUVECs were exposed to antibody-Monobody-conjugated nanoparticles prepared by reacting varying amounts of the antibody (anti-CD31 (CD31) or IgG1 isotype control (Iso)) with the Mb-conjugated NPs.
Figure 2B:
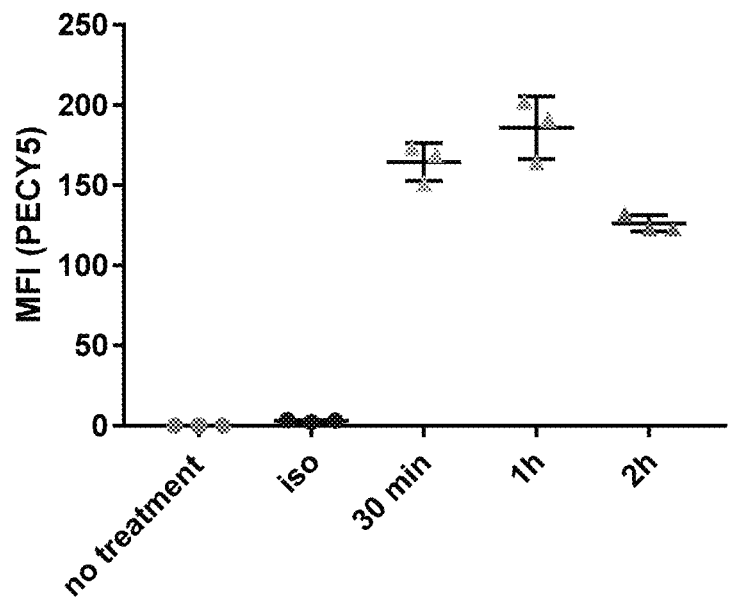
FIG. 2B is a graph showing quantification of the MFI when HUVECs were exposed to antibody-Monobody-conjugated nanoparticles prepared by reacting antibody with Mb-conjugated NPs for varying amounts of time.

Experiments were performed to determine the conditions that allow for optimal conjugation of antibodies to Mb functionalized NPs, and subsequently optimal binding of the NP to cell surface targets. Varying concentrations of anti-CD31 antibody in the coupling reaction indicated that 1 mg/mL of this antibody resulted in high signal intensity when the resulting NPs were tested in static cell culture (FIG. 2A). Higher concentrations of anti-CD31 antibody did not further improve the cell binding (FIG. 2A). Comparison of reaction times indicated that incubation of the conjugation reaction on the orbital shaker for 1 hour was best, with shorter (30 minutes) or longer (2 hours) incubation times not showing any significant improvement in cell binding (FIG. 2B).

A comparison of EDC-NHS verse Mb-linker conjugation approaches is summarized in Table 1.

TABLE 1

Comparison of EDC-NHS conjugation vs. Mb-Linker Approach

| | EDC-NHS approach | Mb-linker approach |
| --- | --- | --- |
| Diameter | 165 ± 20 nm [n = 4] | 168 ± 23 nm [n = 37] |
| PdI | 0.15 ± 0.01 [n = n] | 0.15 ± 0.04 [n = 37] |
| Zeta potential | −17 ± 6 mV [n = 4] | −12 ± 3 mV [n =37] |
| Mass of Ab/mg of NP | 27 ug [n = 1] | 47 ± 3 ug [n = 18] |
| Ab binding to NP efficiency | 53% [n = 1] | 84 ± 6% [n = 18] |

Example 3: Antibody Conjugation Using Monobody Linkers Shows Improved Targeting Efficacy Compared to the Absence of Monobody Linkers Materials and Methods Static cell culture, nanoparticle targeting assays and flow cytometry Static cell culture, nanoparticle targeting assays and flow cytometry were performed as described above. Briefly, HUVECs were plated on a gelatin-treated pate and upon confluence, remained untreated or were treated according to 1 of 3 options: (1) cells were incubated in media containing anti-CD31 or IgG1 isotype control antibody-conjugated NPs, (2) cells were incubated in media containing anti-CD31 or IgG1 isotype control antibody, washed, then incubated in media containing Monobody-conjugated NPs, or (3) cells were incubated in media containing anti-CD31 or IgG1 antibody-Monobody-conjugated NPs. After incubation, the cells were then washed extensively with culture media to remove unbound NPs, harvested via trypsinization, and then analyzed by Flow cytometry.

In vitro cell culture under flow Microfluidic flow experiments were performed at 37° C. using a Bioflux 200 commercial setup made by Fluxion Biosciences combined with a custom-built live cell imaging platform enclosing an inverted Olympus IX71 microscope. HUVECs were seeded at $20.10^6$ cells/mL in bioflux channels coated with fibronectin. After 12 h, the cells were either directly treated with Ab-Mb-NPs at 50 ug/mL flowing at 1 dyne/cm$^2$ for 1 h or first treated with anti-CD31 antibody (Biolegend, part #94218) or IgG1 isotype control antibody (BD Pharmingen, part #624084) at 33 nM flowing at 1 dyne/cm$^2$ for 1 h then washed and treated with Mb-NPs at 50 ug/mL flowing at 1 dyne/cm$^2$ for 1 h. While the NPs were flowing, 1 image was captured every 5 minutes using a 10× objective. After treatment the unbound NPs were washed from the channel and imaging was done along the channel with an Olympus 20× apochromatic air immersion objective (NA=0.95) at both low and high exposures.

Ex Vivo Organ Perfusion of Human Umbilical Arteries

Isolated human umbilical arteries collected less than 4 h after cesarean section was attached to a closed loop, ex vivo perfusion system with a peristaltic pump. Six sections of the same vessel were simultaneously perfused to produce biological replicates, tested side-by-side under identical conditions. The loops were filled with 50 mL of media (M199) and warmed to 37° C. before the injection of 0.5 mg of Ab-Mb-NPs at 0.1 mg/mL. The vessel sections are perfused for 1 h. Then the vessel sections are detached from the loop, the unbound NPs were washed. A piece of the vessel is stained for confocal imaging while the cells of the remaining piece are harvested and analyzed by flow cytometry.

Ex Vivo Organ Perfusion of Kidney

Transplant-declined human kidneys were attached to a closed loop, ex vivo perfusion system as previously described (Tietjen G T., et al., Sci Transl Med., 9(418), eaam6764 (2017)). Briefly, The kidney was perfused with a plasma-free RBC-based perfusate oxygenated and warmed to 36° C. The perfusion parameters (flow, pressure, resistance, urine, perfusate, . . . ) were monitored during the full length of the perfusion. After 1 h of perfusion to assess the health of the kidney, a wedge biopsy was sampled followed by a bolus of 25 mg of Ab-Mb-PLA-PEG NPs containing DiI fluorophore at 5 mg/mL mixt with 25 mg of control untargeted PLA-PEG NPs encapsulating DiO fluorophore were injected into the renal artery line (50 ug/mL of each type of NPs in perfusate). After an additional 4 h, the kidney was removed from the perfusion system, flushed and dissected. Biopsies in different locations were sampled and flash frozen. The frozen biopsies were subsequently sectioned, stained and image using a fluorescence microscope (EVOS).

Results

Figure 3A:
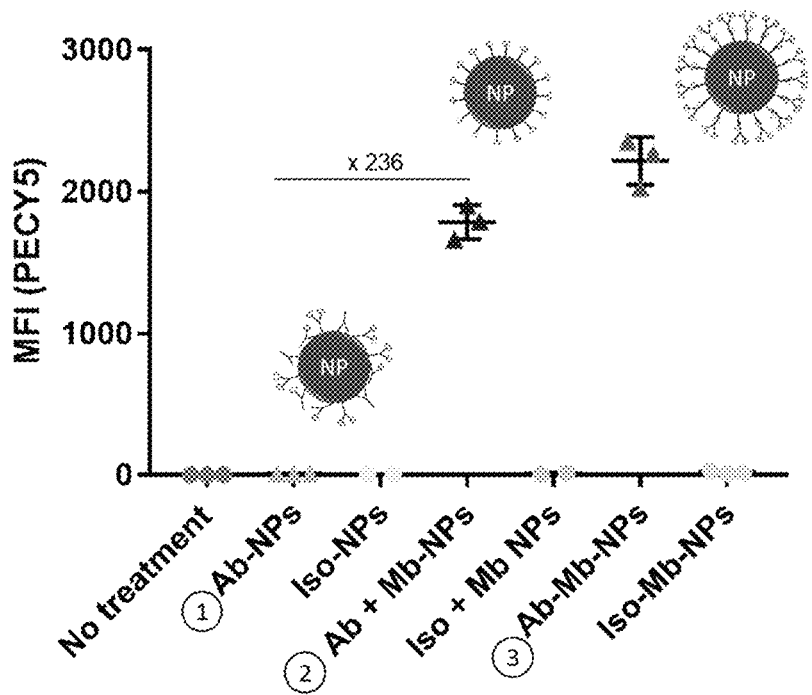
FIG. 3A is a graph showing quantification of the Mean Fluorescence Intensity (MFI) as measured by flow cytometry, when HUVECs, under static culture conditions, were left untreated or treated according to the following legend: (1) exposure to nanoparticles directly conjugated to an anti-CD31 antibody (Ab-NPs) or IgG1 isotype control antibody (Iso-NPs); (2) exposure to anti-CD31 or IgG1 isotype control antibodies followed by exposure to Monobody-conjugated NPs; and (3) exposure to antibody-Monobody-conjugated nanoparticles. This graph is similar to FIG. 3E except that FIG. 3E was measured with a different flow cytometer (Cytoflex) and does not include the Mb-NPs.

Experiments were performed to directly compare the efficiency of targeting when antibodies are directly conjugated to the NP compared to conjugation via a Monobody linker. Under static culture, it was observed that compared to NPs directly conjugated to the Ab (condition 1), use of a Monobody linker yielded between 200 to 300 higher targeting (conditions 2 and 3) (FIG. 3A). In particular, conjugation of the antibody to the NPs via the Mb yielded the highest efficiency of cell targeting which was approximately 24,000 better than the untreated control (FIG. 3A). See also FIG. 3E. Using the exact same core PLA-PEG NPs, the same anti-hum-CD31 Ab and the same concentrations in a classic in vitro binding assay on Human Umbilical Vein Endothelial Cells or HUVECs, the nanoparticles conjugated using the new Ab-Mb-NPs display a dramatic enhancement of binding efficiency compared to standard Ab-NPs. The drastic enhancement in binding may be related to the orientation of the Ab. In the standard conjugation approach the orientation of the Abs is completely random resulting in only part of them able to bind to the cells while in the case of the Mb-linker approach the orientation might be conserved and allow the majority of the Abs to participate to the binding process.

Figure 3B:
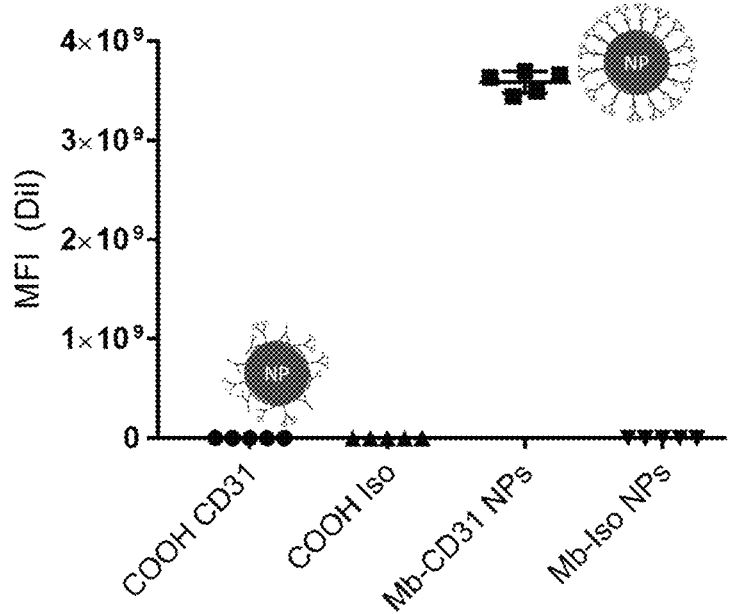
FIG. 3B is a graph showing quantification of the MFI when HUVECs were exposed to NPs under microfluidic flow. In (1) cells were exposed to nanoparticles directly conjugated to an anti-CD31 antibody (COOH CD31) or IgG1 isotype control antibody (COOH Iso) via standard EDC/NHS coupling and (3) cells were exposed to antibody-Monobody-conjugated nanoparticles using either anti-CD31 antibodies or non-binding isotype. MFI was measured by fluorescence microscopy. This graph is similar to FIG. 3F except that FIG. 3F include more replicate of the CD31-Mb-NPs.

This trend was also observed under culture flow conditions. Nanoparticles labeled with anti-CD31 antibody via a Monobody linker showed a markedly higher ability to target cells compared to NPs directly labeled with anti-CD31 antibody (FIG. 3B). See also FIG. 3F. Results indicated the fast and strong binding of the monobody nanoparticles compared to standard nanoparticles (quantitated at a thousand times more binding).

Figure 3C:
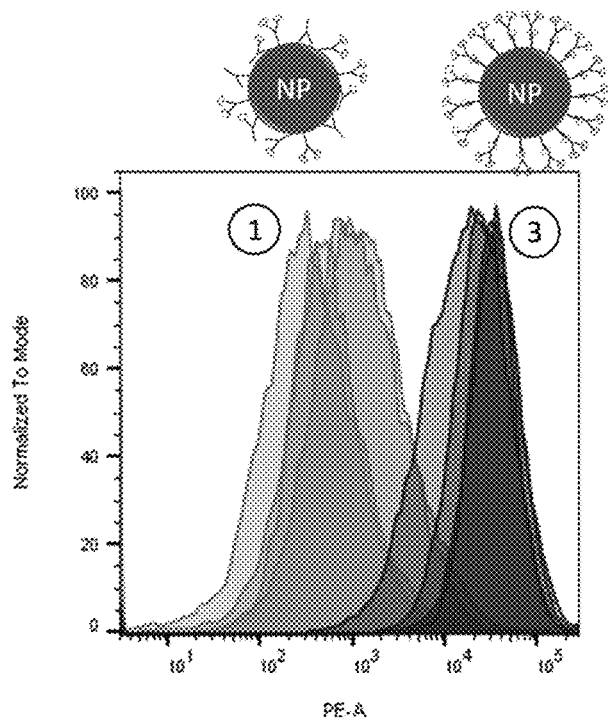
FIG. 3C is a flow cytometry plot showing the distribution of signal intensities for the ex vivo umbilical artery perfusion study, when umbilical arteries were exposed to antibody-conjugated NPs or antibody-Mb-conjugated NPs.
Figure 3D:
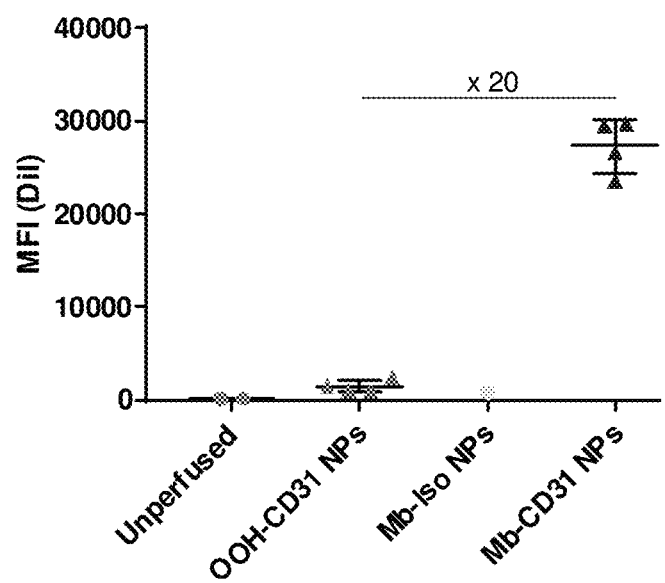
FIG. 3D is a graph showing quantification of the MFI in the ex vivo umbilical artery perfusion study, when umbilical arteries were exposed to anti-CD31 antibody-conjugated NPs or anti-CD31 antibody-Mb-conjugated NPs. This graph is similar to FIG. 3G
Figure 3E:
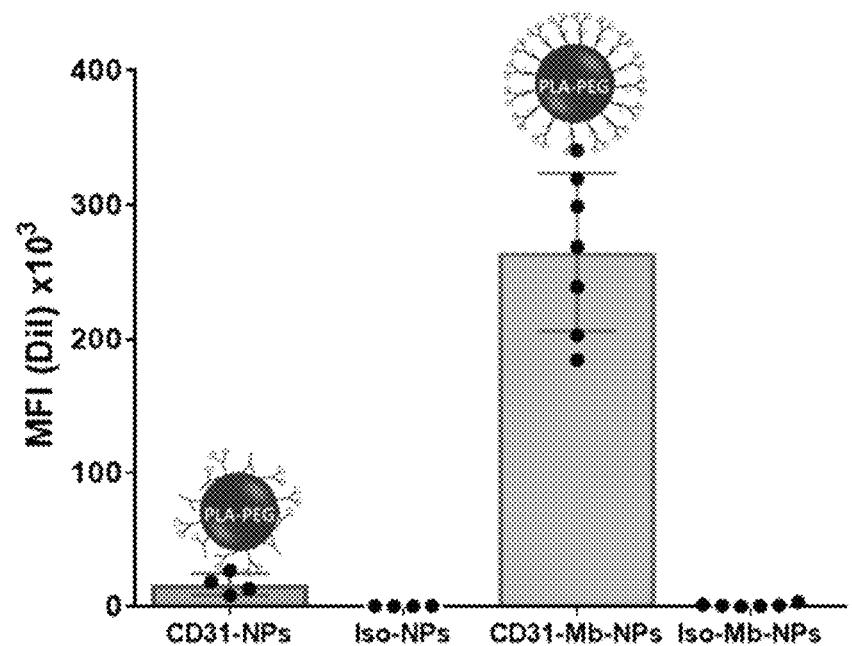
FIG. 3E is a bar graph showing quantification of the Mean Fluorescence Intensity (MFI) as measured by flow cytometry, when HUVECs, under static culture conditions, were treated with nanoparticles (PLGA-PEG) directly conjugated to an anti-CD31 antibody (CD31-NPs) or IgG1 isotype control antibody (Iso-NPs), antibody-Monobody-conjugated nanoparticles (CD31-Mb-NPs), or isotype control antibody-Monobody-conjugated nanoparticles (Iso-Mb-NPs).
Figure 3F:
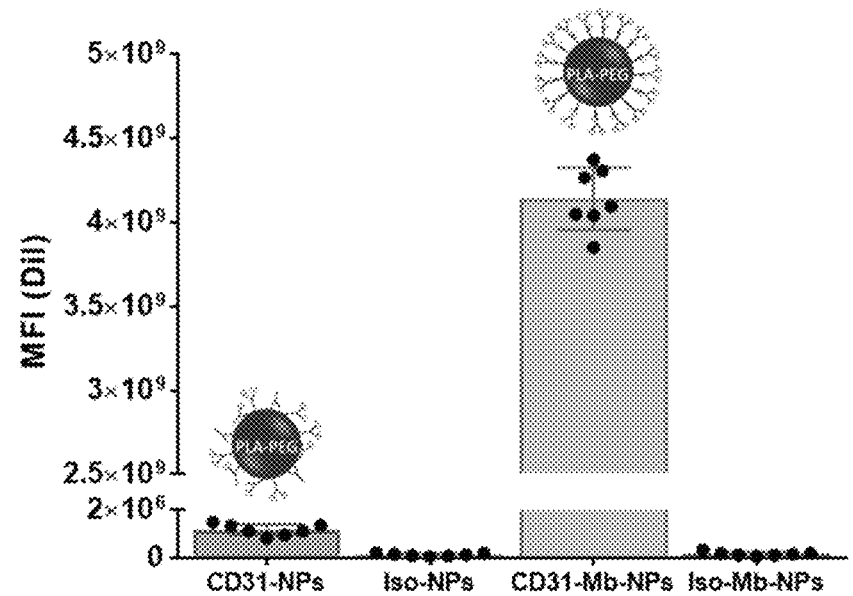
FIG. 3F is a bar graph showing quantification of the MFI as measured by quantitative microscopy, when HUVECs under microfluidic flow were treated with nanoparticles (PLGA-PEG) directly conjugated to an anti-CD31 antibody (CD31-NPs) or IgG1 isotype control antibody (Iso-NPs), CD31 antibody-Monobody-conjugated nanoparticles (CD31-Mb-NPs), or isotype control antibody-Monobody-conjugated nanoparticles (Iso-Mb-NPs).
Figure 3G:
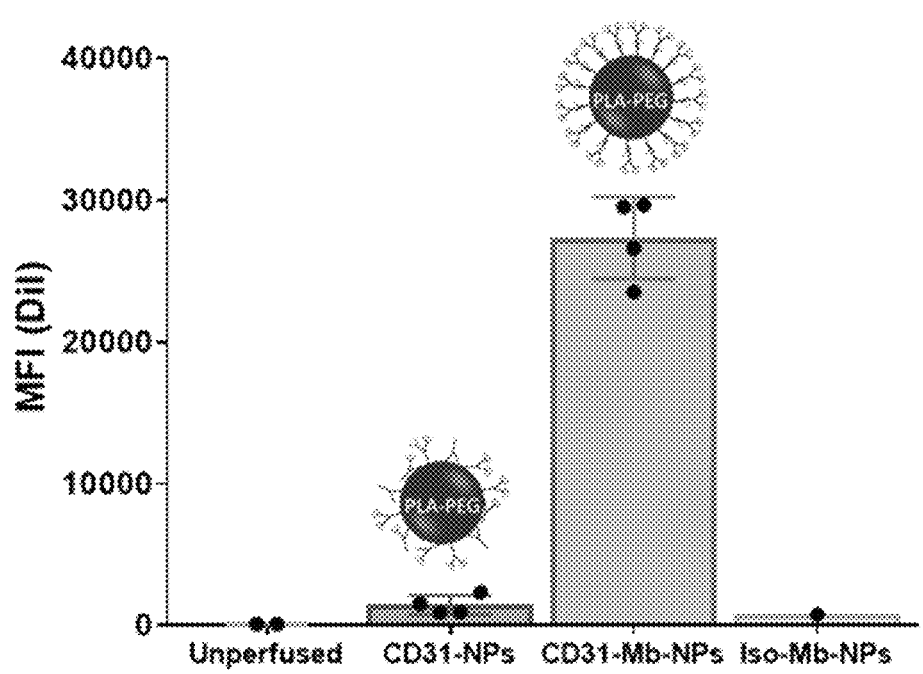
FIG. 3G is a bar graph showing the Mean Fluorescence intensity of the nanoparticles, measured by quantitative microscopy, for the ex vivo umbilical artery perfusion study, when umbilical arteries were exposed to nanoparticles (PLGA-PEG) directly conjugated to an anti-CD31 antibody (CD31-NPs) or IgG1 isotype control antibody (Iso-NPs), CD31 antibody-Monobody-conjugated nanoparticles (CD31-Mb-NPs), or isotype control antibody-Monobody-conjugated nanoparticles (Iso-Mb-NPs).

Finally, the vessel perfusion study indicated that while NPs directly labeled with anti-CD31 antibody did bind to the vessel, NPs labeled with anti-CD31 antibody via a Monobody linker showed about a 20-fold increased ability to accumulate in the vessel (FIGS. 3C-3D). The umbilical artery is an intact vessel used fresh after recovery from c-section, whereas the HUVEC are cultured cells that become less like native endothelium with increasing cell culture time. These results illustrate a similar level of profound binding improvement in a native human vessel that is a less artificial setting than cell culture. See also FIG. 3G. CD31-Mb-NPs bound to the endothelial cells of the human umbilical artery is, once again, much higher than for the standard NPs (quantitated at 20 fold higher). Using confocal microscopy, the CD31-Mb-NPs were found lining with the endothelial cell edge were are located the CD31 antigens.

Figure 4A:
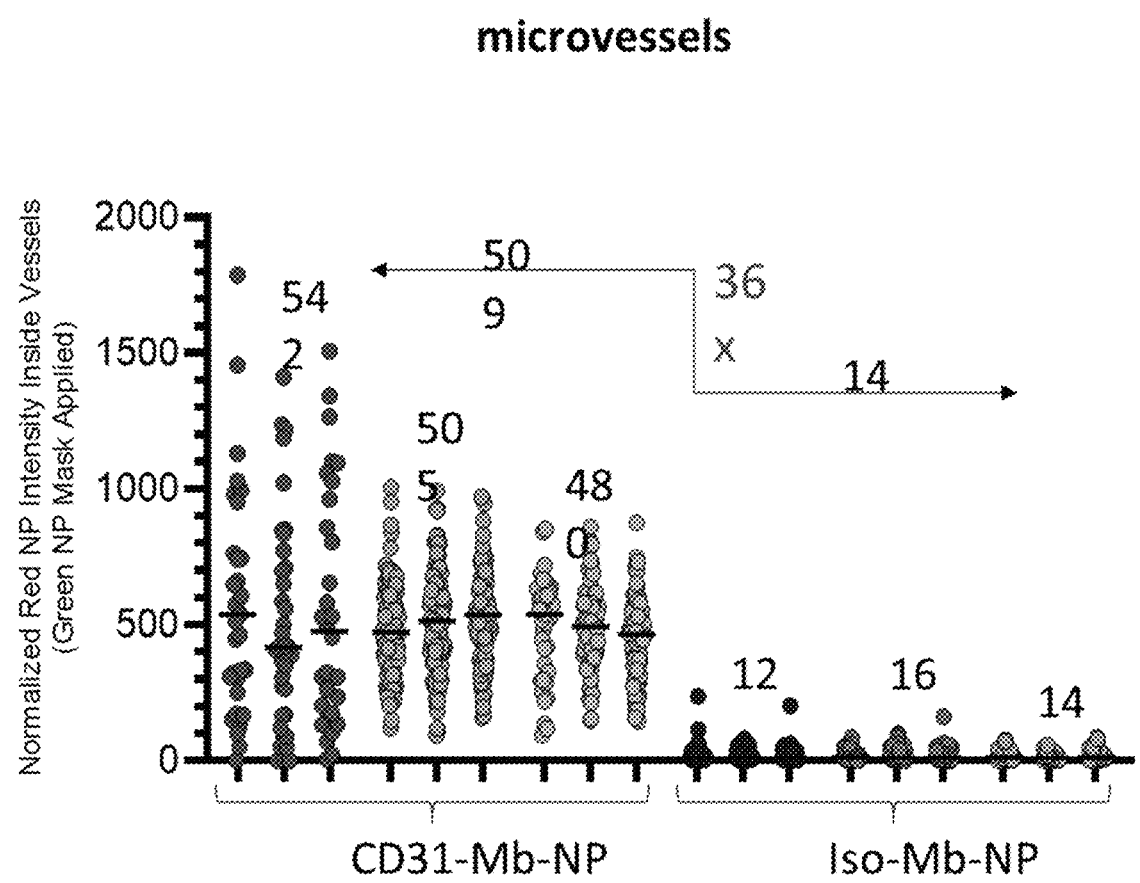
FIG. 4A is a dot plot showing normalized NP intensity of fluorescence (measured by quantitative microscopy) inside vessels (microvessels) exposed to antibody-Monobody-conjugated nanoparticles (CD31-Mb-NPs), or isotype control antibody-Monobody-conjugated nanoparticles (Iso-Mb-NPs) in an ex vivo kidney perfusion assay.
Figure 4B:
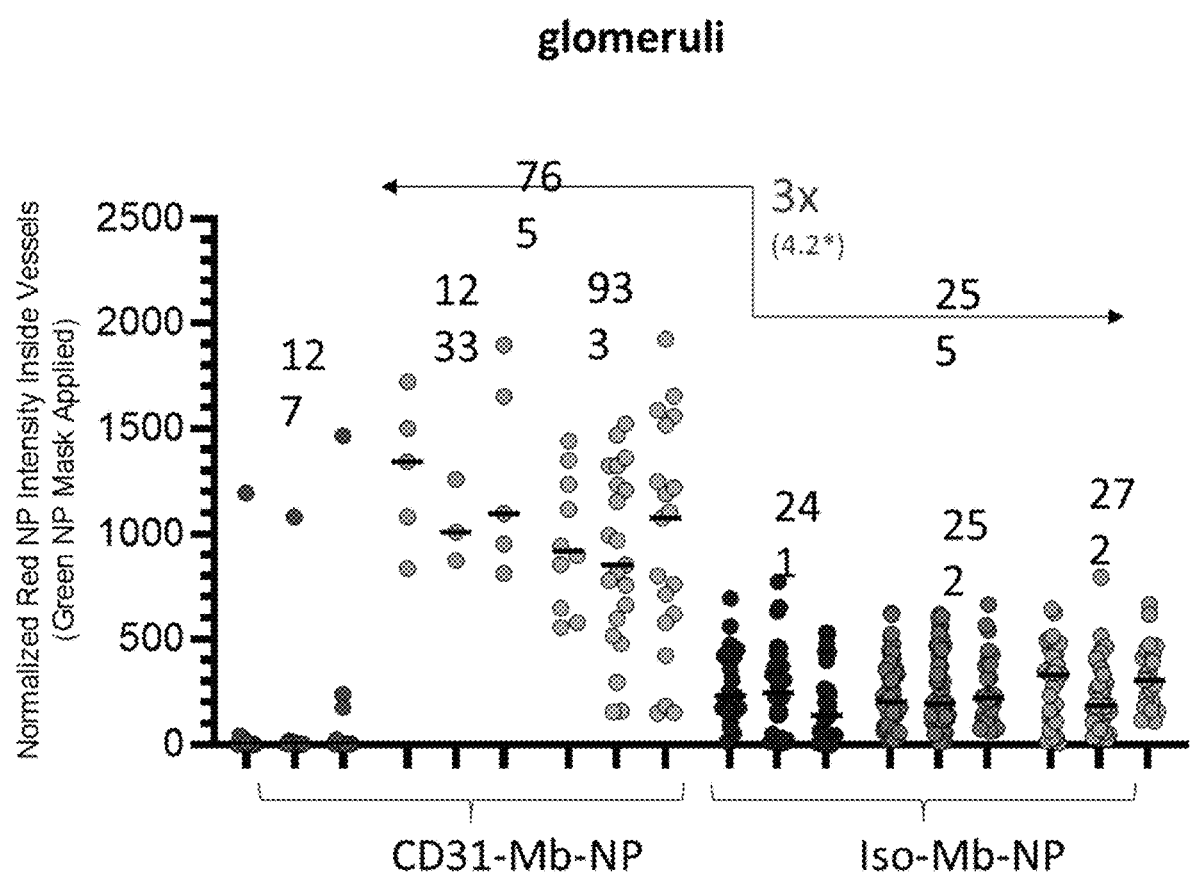
FIG. 4B is a dot plot showing normalized NP intensity of fluorescence (measured by quantitative microscopy) inside vessels (glomeruli) exposed to antibody-Monobody-conjugated nanoparticles (CD31-Mb-NPs), or isotype control antibody-Monobody-conjugated nanoparticles (Iso-Mb-NPs) in an ex vivo kidney perfusion assay.

Ab-Mb-PLA-PEG nanoparticles were also tested in an ex vivo kidney perfusion system. The results are presented in FIGS. 4A and 4B.

Results show the CD31-Mb-NP affinity for the endothelial cell of the kidney vasculature is significantly improved compared to the Isotype control Mb-NP both in the microvessels and in the vasculature of the glomeruli. The area of coverage reach ~70% of the vasculature area in the glomeruli and ~40% in the microvessels.

Altogether, the above-described data demonstrate that targeting NPs via conjugation of Monobody linker to a targeting antibody results in vastly improved targeting.

Example 4: Monobody Mediated Conjugation is Versatile In Addition of an enhanced targeting efficiency the use of a monobody linker allow an enhanced adaptability compared to more complex conjugation method. Indeed, the monobody linker system is readily adaptable to any Abs of the same isotype without re-engineering them allowing to aim for different target. To demonstrate this, a commercially available mouse IgG1 anti-human-ICAM2 Ab was used during the last step of conjugation instead of the previously used mouse IgG1 anti-hum-CD31 Ab.

Figure 5:
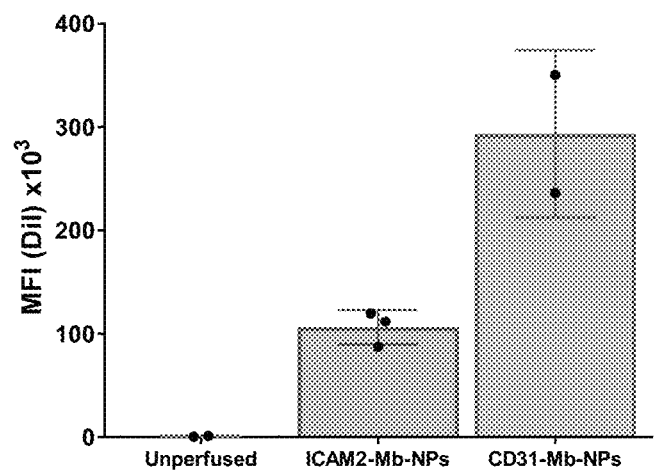
FIG. 5 is a bar showing the Mean Intensity of Fluorescence as measured by flow cytometry for the ex vivo umbilical artery perfusion study, when umbilical arteries were left unperfused or exposed to ICAM2 antibody-Monobody-conjugated nanoparticles or CD31 antibody-Monobody-conjugated nanoparticles.

The binding efficiency was characterized using the ex vivo single vessel perfusion system. Results showed that nanoparticles with ICAM2 Ab bind to the endothelial cells of the vessel. The quantification by flow cytometry showed that the number of ICAM2-Mb-NPs attached to the endothelial cells is twice less than with CD31-Mb-NPs (FIG. 5). This result is consistent with there being twice less ICAM2 antigens on the surface of the endothelial cells than CD31 antigens.

Figure 6:
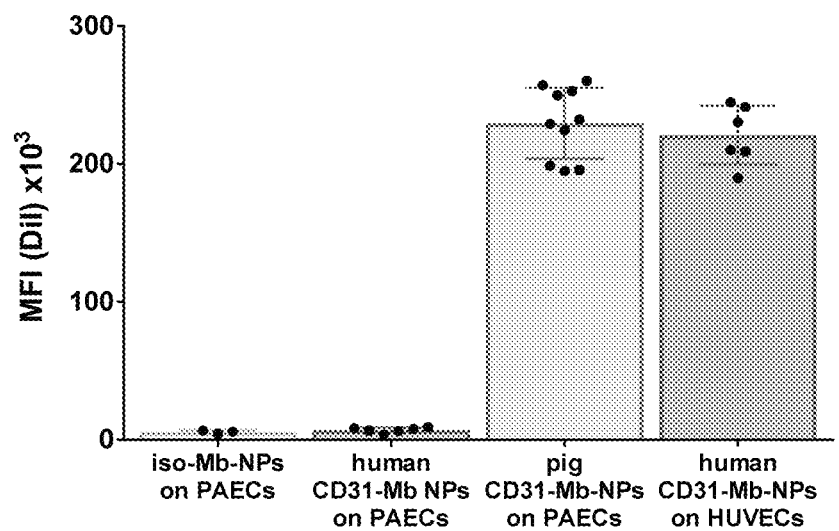
FIG. 6 is a bar graph showing quantification of the Mean Fluorescence Intensity (MFI) as measured by flow cytometry, when pig aorta endothelial cells (PAECs), under static culture conditions, were treated with iso-Mb-NPs, human anti-CD31 antibody-Mb-NPs, pig anti-CD31 antibody-Mb-NPs, compared to HUVECs treated with human anti-CD31 antibody-Mb-NPs.

By using a mouse IgG1 anti-pig-CD31 Ab for the last step of the conjugation process, the ability of a Mb linker to be used to formulate NPs targeting cells of different species was also shown. The binding efficiency was characterized in vitro. The anti-pig-CD31 is binding to pig endothelial cells but not to human endothelial cells. The flow cytometry results show that only the nanoparticles conjugated with the anti-pig CD31 Ab are able to bind to the pig endothelial cells (FIG. 6). The efficiency of binding is equivalent to the one obtained when using nanoparticles with anti-human-CD31 Ab on human endothelial cells (far right bar).

An alternative method of conjugation was also tested. Rather than a maleimide group grafted directly to the polymer constituting the NP, PVA-Vinyl Sulfone was utilized to stabilize NPs prepared by emulsion evaporation therefore allowing the use of the monobody linker to attach anti-CD31 Ab to Poly(amine-co-ester) (PACE) NPs.

Preparation of polyvinyl alcohol—vinyl sulfone from polyvinyl alcohol and divinyl sulfone:

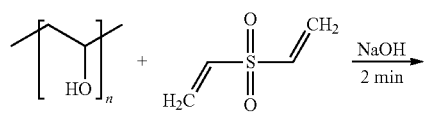

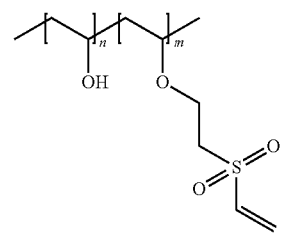

Particle characteristics are illustrated in Table 2.

TABLE 2

Ab conjugation to PACE NPs through Mb-linker

PVA—S(=O)(=O)—CH=CH2

| | PACE-PVA-VS |
|---|---|
| Unconjugated NPs | |
| Diameter | 341 nm [n = 1] |
| PdI | 0.17 [n = 1] |
| Zeta potential | 20 mV [n = 1] |
| Conjugated NPs | |
| Diameter | 373 ± 56 nm [n = 12] |
| PdI | 0.19 ± 0.05 [n = 12] |
| Zeta potential | −21 ± 6 mV [n = 12] |
| Mass of Ab/mg of NP | 25 ± 12 ug [n = 6] |
| Ab binding to NP efficiency | 44 ± 22% [n = 6] |

Figure 7:
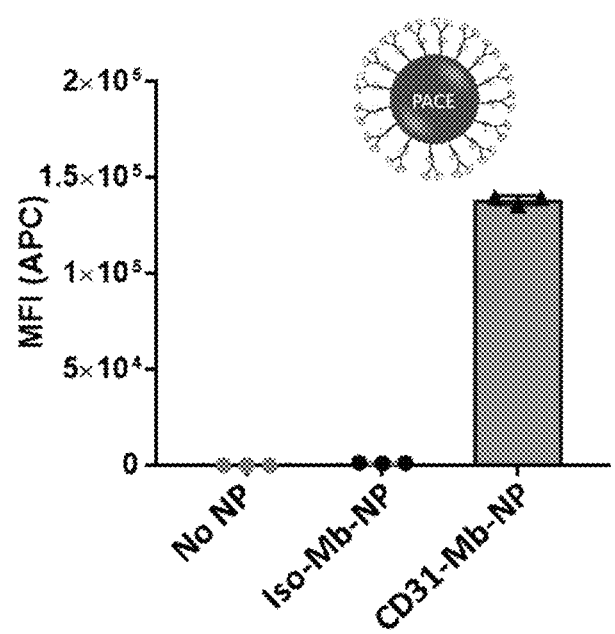
FIG. 7 is a bar graph showing the Mean Fluorescence Intensity (MFI) as measured by flow cytometry, when HUVECs, under static culture conditions, were treated with no NPs, iso-Mb-PACE NPs, or anti-CD31 antibody-Mb-PACE NPs.

The resulting targeted particles were tested in an HUVEC in vitro binding assay. The results are presented in FIG. 7, which shows the drastic increase of binding of the CD31-Mb-NP compared to the control Iso-Mb-NP In summary, a new way to conjugate nanoparticles to antibodies that dramatically improves the efficiency of cell targeting, most likely due to improved orientation of the antibodies is provided. This modular and easy adaptable system gives the opportunity to use any nanoparticles presenting a thiol reactive group on its surface. Any antibody of the same IgG subtype can be conjugated through the Mb-Linker to these NPs without requiring further optimization. Advantages of the disclosed monobody linker system include, but are not limited to, high binding affinity, use any NPs with thiol reactive group on surface, development of the NPs only need to be done once, use any available Ab (same IgG subtype), easy change of target or of species. This system potentially offers new opportunities for treatment and may be particularly useful during normothermic perfusion of human organ in the context of transplantation.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A composition comprising a particle functionalized with one or more monobodies, wherein the one or more monobodies comprises:
   (i) a first surface comprising a targeting agent binding site capable of binding to an Fc domain of an antibody, and
   (ii) a second surface comprising a chemical moiety through which the one or more monobodies is conjugated to the particle's surface,
   wherein the one or more monobodies each comprises a polypeptide comprising the amino acid sequence of SEQ ID NO:2, SEQ ID NO:3, or SEQ ID NO:4, or a variant thereof comprising at least 90% sequence identity to SEQ ID NO:2, SEQ ID NO:3, or SEQ ID NO:4, with or without the N-terminal tag, the C-terminal tag, or both.

2. The composition of claim 1, further comprising an antibody bound to the targeting agent binding site of the one or more monobodies via the Fc domain of the antibody.

3. The composition of claim 1, wherein the one or more monobodies each comprises an immunoglobulin fold and no disulfide bonds.

4. The composition of claim 1, wherein the conjugation of the one or more monobodies to the particle's surface comprises a covalent linkage, wherein the covalent linkage comprises the structure:

—X—Ra—Y—                                   Formula I wherein,

X and Y, independently, contain between 3 and 90 atoms, inclusive, between 3 and 85 atoms, inclusive, between 3 and 80 atoms, inclusive, between 3 and 70 atoms, inclusive, between 3 and 60 atoms, inclusive, between 3 and 50 atoms, inclusive, between 3 and 40 atoms, inclusive, between 3 and 30 atoms, inclusive, or between 3 and 20 atoms, inclusive, and Ra comprises a 3-thiopyrrolidine-2,5-dione moiety, 3-aminopyrrolidine-2,5-dione moiety, 3-thiomaleimide moiety, 3-aminomaleimide moiety, a triazole moiety, a carbamate, oxime ether, hydrazone, a carbonyl, imine, sulfonamide, azo, dialkyl dialkoxysilane, diaryl dialkoxysilane, orthoester, acetal, aconityl, β-thiopropionate, phosphoramidate, trityl, vinyl ether, polyketal, or a combination thereof.

5. The composition of claim 1, wherein the chemical moiety is an amino acid selected from the group consisting of cysteine, lysine, ornithine, arginine, serine, threonine, tyrosine, and a combination thereof.

6. The composition of claim 1, wherein the chemical moiety is a cysteine.

7. The composition of claim 1, wherein the particle is an expression vector.

8. The composition of claim 1, further comprises a pharmaceutically acceptable carrier.

9. A method of delivering a particle to a subject in need thereof comprising
   (i) administering to the subject, or
   (ii) administering to an organ, tissue, or cell to be transplanted to the subject,
   an effective amount of the composition of claim 1 and an antibody.

10. The method of claim 9, wherein the antibody is administered prior to or co-administered with administering the composition.

11. The method of claim 9, wherein administration to the organ occurs ex vivo.

12. The composition claim 1, wherein the polypeptide comprises the amino acid sequence of SEQ ID NO:2, SEQ ID NO:3, or SEQ ID NO:4, with or without the N-terminal tag, the C-terminal tag, or both.

13. The composition of claim 1, wherein the particle is a polymeric particle, a liposome, or an inorganic particle.

14. The composition of claim 1, wherein the particle comprises one or more therapeutic agents, diagnostic agents, prophylactic agents, or a combination thereof.

15. The composition of claim 1, wherein the polypeptide comprises the amino acid sequence of SEQ ID NO:2, SEQ ID NO:3, or SEQ ID NO:4, without the N-terminal tag.

16. The composition of claim 1, wherein the polypeptide comprises the amino acid sequence of SEQ ID NO:2, SEQ ID NO:3, or SEQ ID NO:4.

* * * * *